(12) United States Patent
Schmitt-Willich et al.

(10) Patent No.: US 6,248,306 B1
(45) Date of Patent: *Jun. 19, 2001

(54) CASCADE POLYMER COMPLEXES, PROCESS FOR THEIR PRODUCTION AND PHARMACEUTICAL AGENTS CONTAINING SAID COMPLEXES

(75) Inventors: Heribert Schmitt-Willich; Johannes Platzek; Ulrich Niedballa; Bernd Raduchel, all of Berlin; Andreas Muhler, Neuenhagen; Thomas Frenzel, Berlin; Wolfgang Ebert, Berlin, all of (DE)

(73) Assignee: Schering Aktiengesellschaft, Berlin and Bergkamen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/485,558

(22) Filed: Jun. 6, 1995

(30) Foreign Application Priority Data

Jul. 7, 1994 (DE) ................................................. 44 25 857

(51) Int. Cl.[7] .......................... A61K 51/00; A61B 5/055; C07F 5/00; C07D 225/00; C08F 283/00
(52) U.S. Cl. ..................... 424/1.65; 424/9.36; 424/9.364; 424/9.365; 424/DIG. 16; 534/10; 534/14; 534/15; 534/16; 540/465; 540/473; 540/474
(58) Field of Search .......................... 424/1.65, 9.322, 424/9.34, 9.341, 9.36, 9.364, 9.365, DIG. 16; 534/10, 14, 15, 16; 540/465, 473, 474; 564/191, 198; 528/288, 328, 332, 310, 363

(56) References Cited

U.S. PATENT DOCUMENTS

| | | | |
|---|---|---|---|
| 4,587,329 | * | 5/1986 | Tomalia et al. ........................ 528/363 |
| 4,863,717 | * | 9/1989 | Keana ....................................... 424/9 |
| 5,135,737 | * | 8/1992 | Keana ....................................... 424/9 |
| 5,281,704 | * | 1/1994 | Love et al. ............................ 540/465 |
| 5,364,613 | * | 11/1994 | Sieving et al. ............................ 424/9 |
| 5,364,614 | * | 11/1994 | Platzek et al. ............................ 424/9 |
| 5,405,601 | * | 4/1995 | Dunn et al. ............................... 424/9 |
| 5,446,145 | * | 8/1995 | Love et al. ............................ 540/465 |
| 5,449,761 | * | 9/1995 | Belinka, Jr. et al. .................. 534/10 |
| 5,517,993 | * | 5/1996 | Unger et al. ........................ 128/653.4 |
| 5,527,524 | * | 6/1996 | Tomalia et al. ....................... 424/1.33 |
| 5,556,968 | * | 9/1996 | Carvalho et al. ..................... 540/460 |
| 5,593,660 | * | 1/1997 | Krause et al. ...................... 424/9.451 |
| 5,820,849 | * | 10/1998 | Schmitt-Willich et al. .......... 424/9.36 |
| 5,874,061 | * | 2/1999 | Schmitt-Willich et al. ....... 424/9.363 |

FOREIGN PATENT DOCUMENTS

| | | |
|---|---|---|
| 43 44 460 | 6/1995 | (DE) . |
| WO 93/06868 | 4/1993 | (WO) . |

OTHER PUBLICATIONS

Wiener et al., *Magnetic Resonance in Medicine*, vol 31 (1): pp. 1–8, Jan 1, 1994.*
G. Adam et al., Magnetic Resonance in Medicine, vol. 32d, No. 5, Nov. 1994, pp. 622–628.

* cited by examiner

*Primary Examiner*—Michael G. Hartley
(74) *Attorney, Agent, or Firm*—Millen, White, Zelano, & Branigan

(57) ABSTRACT

Cascade polymer complexes containing a) complexing ligands of general formula I

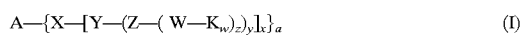

$$A-\{X-[Y-(Z-(W-K_w)_z)_y]_x\}_a \quad (I)$$

in which
A stands for a nitrogen-containing cascade nucleus of base multiplicity a,
X and Y, independently of one another, stand for a direct bond or a cascade reproduction unit of reproduction multiplicity x or y,
Z and W, independently of one another, stand for a cascade reproduction unit of reproduction multiplicity z or w,
K stands for the radical of a complexing agent,
a stands for numbers 2 to 12,
x, y, z and w, independently of one another, stand for numbers 1 to 4, provided that at least two reproduction units are different and that $$16 \leq a \cdot x \cdot y \cdot z \cdot w \leq 64$$

holds true for the product of the multiplicities, b) at least 16 ions of an element of atomic numbers 20 to 29, 39, 42, 44 or 57–83 and c) optionally cations of inorganic and/or organic bases, amino acids or amino acid amides are valuable compounds for diagnosis and therapy.

14 Claims, 1 Drawing Sheet

CASCADE POLYMER COMPLEXES, PROCESS FOR THEIR PRODUCTION AND PHARMACEUTICAL AGENTS CONTAINING SAID COMPLEXES

The invention relates to new cascade polymer complexes, agents containing these compounds, the use of the complexes in diagnosis and therapy, and a process for the production of these compounds and agents.

The contrast media that are now used in clinical practice for the modern imaging processes of nuclear spin tomography (MRI [magnetic resonance imaging]) and computer tomography (CT) [Magnevist®, Pro Hance®, Ultravist® and Omniscan®] are dispersed in the entire extracellular space of the body, i.e., in the intravascular space and interstitium. This distribution space comprises about 20% of the volume of the body.

In clinical practice, extracellular MRI contrast media were first used successfully in the diagnosis of cerebral and spinal disease processes since therein a quite special situation exists with respect to the regional distribution space. In the brain and spinal cord, extracellular contrast media in healthy tissue do not leave the intravascular space because of the blood-brain barrier. In the case of pathological processes with disruption of the blood-brain barrier (e.g., malignant tumors, inflammations, demyelinating diseases, etc.), regions with elevated blood-vessel permeability develop inside the brain for these extracellular contrast media (Schmiedl et al., MRI of blood-brain barrier permeability in astrocytic gliomas: application of small and large molecular weight contrast media, Magn. Reson. Med. 22: 288, 1991). Affected tissue can be identified with high contrast relative to healthy tissue by exploiting this disruption of vascular permeability.

Outside of the brain and the spinal cord, however, no such permeability barrier exists for the above-mentioned contrast media (Canty et al., First-pass entry of nonionic contrast agent into the myocardial extravascular space. Effects on radiographic estimate of transit time and blood volume. Circulation 84: 2071, 1991). Thus, the concentration of the contrast medium is no longer dependent on vascular permeability, but only on the size of the extracellular space in the corresponding tissue. Delimitation of the vessels relative to the surrounding interstitial space using such contrast medium is thus not possible.

A contrast medium that is dispersed exclusively in the vascular space would be desirable, particularly for the visualization of vessels. The purpose of such a blood-pool agent would be to make it possible, with the aid of nuclear spin tomography, to delimit tissue with sufficient blood supply from tissue with insufficient blood supply, and thus to diagnose an ischemia. Infarcted tissue could also be delimited, based on its anemia, from surrounding healthy or ischemic tissue if a vasal contrast medium is used. This is of special importance if the point is to distinguish a myocardial infarction from an ischemia.

To date, most of the patients in whom there is suspicion of cardiovascular disease (this disease is the most frequent cause of death in Western industrialized countries) have to undergo invasive diagnostic tests. In angiography, at present, diagnostic radiology with the aid of iodine-containing contrast media is used in particular. These tests suffer from various drawbacks: they are associated with the risk of radiation exposure, as well as with difficulties and stresses, which therefore particularly have the effect that the iodine-containing contrast media, as compared with NMR contrast media, have to be used in much higher concentrations.

There is therefore a need for NMR contrast media which can mark the vascular space (blood-pool agents). These compounds would desirably be distinguished by good compatibility and by high effectiveness (high increase of signal intensity with MRI).

Thus far, the attempt to solve at least a part of this problem by using complexing agents that are bound to macromolecules or biomolecules has been successful only to a limited extent.

Thus, for example, the number of paramagnetic centers in the complexes that are described in European Patent Applications No. 0 088 695 and No. 0 150 844 is not sufficient for satisfactory imaging.

If the number of metal ions required is increased by repeated introduction of complexing units into a macromolecular biomolecule, this is associated with an intolerable impairment of the affinity and/or specificity of this biomolecule [J. Nucl. Med. 24, 1158 (1983)].

Macromolecules can generally be suitable as contrast media for angiography. But 24 hours after intravenous injection in rats, albumin-GdDTPA (Radiology 1987; 162: 205), for example, shows a concentration in the liver tissue that constitutes almost 30% of the dose. In addition, only 20% of the dose is eliminated in 24 hours.

The macromolecule polylysine-GdDTPA (European Patent Application, Publication No. 0 233 619) has also proved suitable as blood-pool agent. Because of production, however, this compound consists of a mixture of molecules of different sizes. In excretion tests in rats, it was shown that this macromolecule is excreted unchanged by glomerular filtration through the kidneys. Due to factors related to synthesis, however, polylysine-GdDTPA may also contain macromolecules that are so large that they cannot pass through the capillaries of the kidneys in the case of glomerular filtration and thus remain in the body.

Also, macromolecular contrast media based on carbohydrates, e.g., dextran, have been described (European Patent Application, Publication No. 0 326 226). The drawback of these compounds lies in the fact that the latter generally carry only about 5% of the signal-enhancing paramagnetic cation.

The polymers described in European Patent Application No. 0 430 863 already represent a step toward blood-pool agents since they no longer exhibit the size and molecular weight relative to heterogeneity that are characteristic of the previously mentioned polymers. They leave something to be desired, however, as regards complete elimination, compatibility, and/or effectiveness.

An object of the invention was therefore to make available new diagnostic tools particularly to identify and locate vascular diseases that do not have the above-mentioned drawbacks. This object is achieved by this invention. Upon further study of the specification and appended claims, further objects and advantages of this invention will become apparent to those skilled in the art.

It has been found that complexes which consist of nitrogen-containing cascade polymers and which are provided with complexing ligands, at least 16 ions of an element of atomic numbers 20–29, 39, 42, 44 or 57–83, and optionally cations of inorganic and/or organic bases, amino acids or amino acid amides, and optionally acylated amino groups are surprisingly very well suited for the production of NMR [nuclear magnetic resonance] and x-ray diagnostic agents without exhibiting the mentioned drawbacks.

The complexing cascade polymers according to the invention can be described by general formula I $$A\text{—}\{X\text{—}[Y\text{—}(Z\text{—}(W\text{—}K_w)_z)_y]_x\}_a \qquad (I),$$

in which
- A stands for a nitrogen-containing cascade nucleus of base multiplicity a,
- X and Y, independently of one another, stand for a direct bond or a cascade reproduction unit of reproduction multiplicity x or y,
- Z and W, independently of one another, stand for a cascade reproduction unit of reproduction multiplicity z or w,
- K stands for the radical of a complexing agent,
- a stands for numbers 2 to 12,
- x, y, z and w, independently of one another, stand for numbers 1 to 4, provided that at least two reproduction units are different and that $$16 \leq a \cdot x \cdot y \cdot z \cdot w \leq 64$$

holds true for the product of the multiplicities.

As cascade nucleus A, the following are suitable examples: a nitrogen atom,

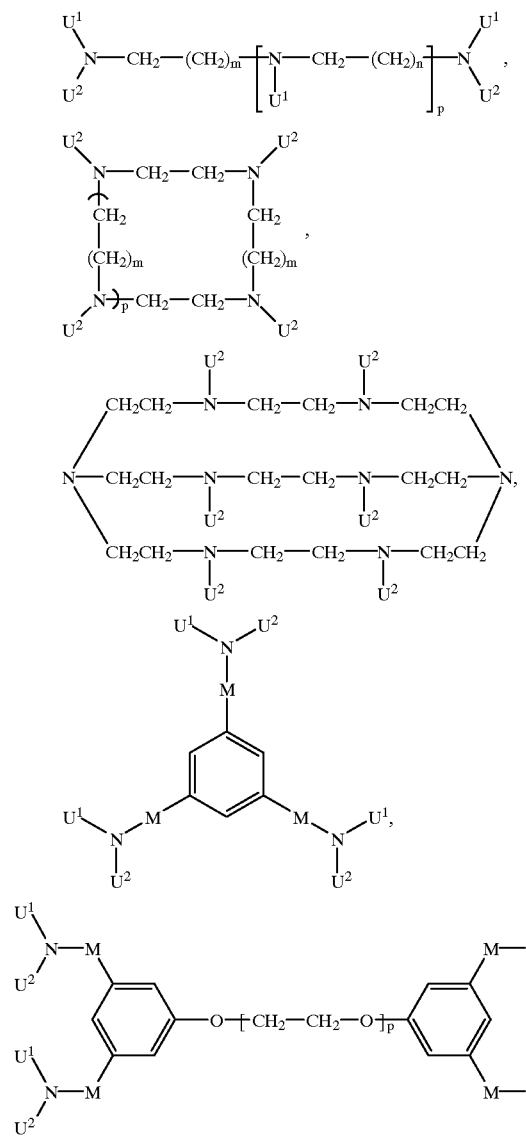

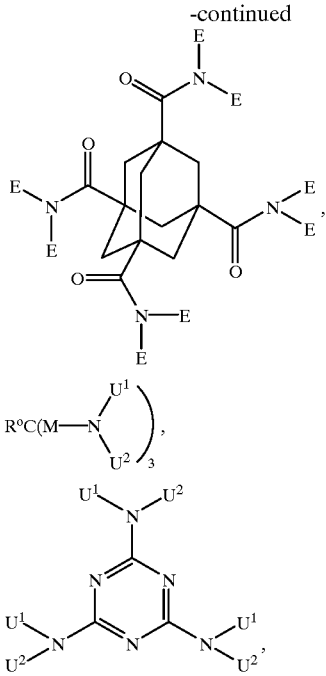

in which
- m and n stand for numbers 1 to 10,
- p stands for numbers 0 to 10,
- $U^1$ stands for $Q^1$ or E,
- $U^2$ stands for $Q^2$ or E with
- E meaning the group

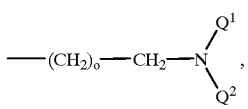

in which
- o stands for numbers 1 to 6,
- $Q^1$ stands for a hydrogen atom or $Q^2$ and
- $Q^2$ stands for a direct bond, i.e., to one of the reproduction units,
- M stands for a $C_1$–$C_{10}$ alkylene chain which optionally is interrupted by 1 to 3 oxygen atoms and/or optionally is substituted with 1 to 2 oxo groups,
- $R^o$ stands for a branched or unbranched $C_1$–$C_{10}$ alkyl radical, a nitro, amino, carboxylic acid group or for

in which the number of $Q^2$ groups corresponds to base multiplicity a.

The nitrogen atom, whose three bonds (base multiplicity a=3) in a first "inner layer" (generation 1) are occupied by three reproduction units X or Y (if X stands for a direct bond and thus x=a) or Z (if X and Y together stand for a direct bond), represents the simplest case of a cascade nucleus; in other words: the three hydrogen atoms of the basic cascade starter ammonia $A(H)_a=NH_3$ have been substituted by three reproduction units X or Y or Z. In this case, the number of $Q^2$ groups contained in cascade nucleus A represents base multiplicity a.

Reproduction units X, Y, Z and W contain —$NQ^1Q^2$ groups, in which $Q^1$ means a hydrogen atom or $Q^2$ and $Q^2$ means a direct bond. The number of $Q^2$ groups contained in the respective reproduction unit (e.g., X) corresponds to the reproduction multiplicity of this unit (e.g., x in the case of X). The product of all multiplicities a·x·y·z·w indicates the number of complexing agent radicals K bound in the cascade polymers. The polymers according to the invention contain at least 16 and at most 64 radicals K in the molecule, which in each case can bond one to a maximum of three (in the case of divalent ions), preferably one, ions of an element of the above-mentioned atomic numbers.

The last generation, i.e., reproduction unit W bound to complexing agent radical K, is bound to K with NH groups (—$NQ^1Q^2$ with $Q^1$ meaning a hydrogen atom and $Q^2$=direct bond), while the preceding reproduction units can be linked together both by $NHQ^2$ groups (e.g., by acylation reactions) and by $NQ^2Q^2$ groups (e.g., by alkylation reactions).

The cascade polymer complexes according to the invention exhibit a maximum of 10 generations (i.e., more than just one of reproduction units X, Y and Z can also be present in the molecule in each case), but preferably 2 to 4 generations, in which at least two of the reproduction units in the molecule are different.

As preferred cascade nuclei A, those are indicated which fall under the above-mentioned general formulas if m stands for numbers 1–3, especially preferably for number 1, n stands for numbers 1–3, especially preferably for number 1, p stands for numbers 0–3, especially preferably for number 1, o stands for number 1, M stands for a —$CH_2$—, —CO— or —$CH_2CO$— group and $R^o$ stands for a —$CH_2NU^1U^2$, $CH_3$ or $NO_2$ group.

As further preferred cascade starters $A(H)_a$, there can be listed, e.g.:

(In the parentheses, base multiplicity a is indicated for the case where subsequent mono- or disubstitution is used in building the next generation)

| | |
|---|---|
| Tris (aminoethyl) amine | (a = 6 or 3); |
| tris (aminopropyl) amine | (a = 6 or 3); |
| diethylenetriamine | (a = 5 or 3); |
| triethylenetetramine | (a = 6 or 4); |
| tetraethylenepentamine | (a = 7 or 5); |
| 1,3,5-tris(aminomethyl)benzene | (a = 6 or 3); |
| trimesic acid triamide | (a = 6 or 3); |
| 1,4,7-triazacyclononane | (a = 3); |
| 1,4,7,10-tetraazacyclododecane | (a = 4); |
| 1,4,7,10,13-pentaazacyclopentadecane | (a = 5); |
| 1,4,8,11-tetraazacyclotetradecane | (a = 4); |
| 1,4,7,10,13,16-hexaazacyclooctadecane | (a = 6); |
| 1,4,7,10,13,16,19,22,25,28-decaazacyclotriacontane | (a = 10); |
| tetrakis(aminomethyl)methane | (a = 8 or 4); |
| 1,1,1-tris(aminomethyl)ethane | (a = 6 or 3); |
| tris(aminopropyl)-nitromethane | (a = 6 or 3); |
| 2,4,6-triamino-1,3,5-triazine | (a = 6 or 3); |
| 1,3,5,7-adamantanetetracarboxylic acid amide | (a = 8 or 4); |
| 3,3',5,5'-diphenylether-tetracarboxylic acid amide | (a = 8 or 4); |
| 1,2-bis[phenoxyethane]-3',3'',5',5''-tetracarboxylic acid amide 1,4,7,10,13,16,21,24-octaazabicyclo-[8.8.8]hexacosan | (a = 8 or 4); (a = 6) |

It can be pointed out that the definition as cascade nucleus A and thus the separation of cascade nucleus and first reproduction unit can be selected by purely formal means and thus independently of the actual synthesis of the desired cascade polymer complexes. Thus, e.g., the tris(aminoethyl) amine used in Example 4 can be considered as cascade nucleus A itself (compare the general formula, indicated first for A, with m=n=p=1, $U^1$=E with o meaning number 1 and $U^1$=$U^2$=$Q^2$) but also as a nitrogen atom (=cascade nucleus A), which as a first generation exhibits three reproduction units

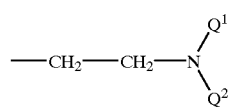

(compare the definition of E).

Cascade reproduction units X, Y, Z and W are preferably defined independently of one another, by E,

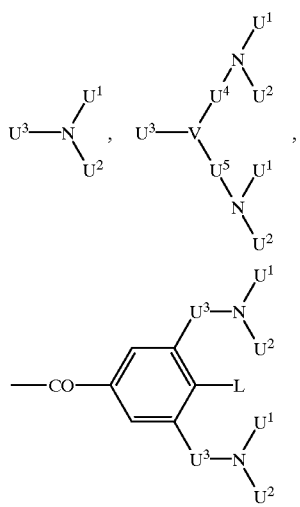

in which $U^1$ stands for $Q^1$ or E, $U^2$ stands for $Q^2$ or E with E meaning the group

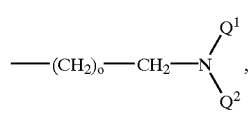

in which o stands for numbers 1 to 6, $Q^1$ stands for a hydrogen atom or $Q^2$, $Q^2$ stands for a direct bond, $U^3$ stands for a $C_1$–$C_{20}$ alkylene chain which optionally is interrupted by 1 to 10 oxygen atoms and/or 1 to 2 —$NR^2$—$(CO)_q$— group, 1 to 2 phenylene radicals and/or 1 to 2 phenylenoxy radicals and/or optionally is substituted by 1 to 2 oxo, thioxo, carboxy, $C_1$–$C_5$ alkylcarboxy, $C_1$–$C_5$ alkoxy, hydroxy or $C_1$–$C_5$ alkyl groups, in which q stands for numbers 0 or 1 and $R^2$ stands for a hydrogen atom or a methyl or an ethyl radical, which optionally is substituted with 1–2 hydroxy or 1 carboxy group(s), L stands for a hydrogen atom or the group

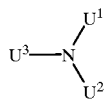

V stands for methine group

if at the same time $U^4$ means a direct bond or group M and $U^5$ has one of the meanings of $U^3$ or V stands for group

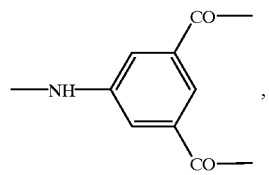

if at the same time $U^4$ and $U^5$ are identical and mean the direct bond or group M.

Preferred cascade reproduction units X, Y, Z and W are those in which in the above-mentioned general formulae, radical $U^3$ stands or —CO—, —COCH$_2$OCH$_2$CO—, —COCH$_2$—, —CH$_2$CH$_2$—, —CONHC$_6$H$_4$—, —COCH$_2$CH$_2$CO—, —COCH$_2$—CH$_2$CH$_2$CO—, —COCH$_2$CH$_2$CH$_2$CH$_2$CO—, radical $U^4$ stands for a direct bond, —CH$_2$CO—, radical $U^5$ stands for a direct bond, for —(CH$_2$)$_4$—, —CH$_2$CO—, —CH(COOH)—, CH$_2$OCH$_2$CH$_2$—, —CH$_2$C$_6$H$_4$— or CH$_2$—C$_6$H$_4$OCH$_2$CH$_2$—, and radical E stands for a group

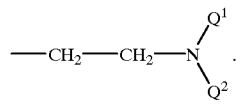

The following can be cited as examples of cascade reproduction units X, Y, Z and W:

—CH$_2$CH$_2$NH—; —CH$_2$CH$_2$N<;
—COCH(NH—)(CH$_2$)$_4$NH—; —COCH(N<)(CH$_2$)$_4$N<;
—COCH$_2$OCH$_2$CON(CH$_2$CH$_2$NH—)$_2$;
—COCH$_2$OCH$_2$CON(CH$_2$CH$_2$N<)$_2$;
—COCH$_2$N(CH$_2$CH$_2$NH—)$_2$; —COCH$_2$N(CH$_2$CH$_2$N<)$_2$;
—COCH$_2$NH—; —COCH$_2$N<;
—COCH$_2$CH$_2$CON(CH$_2$CH$_2$NH—)$_2$;
—COCH$_2$CH$_2$CON(CH$_2$CH$_2$N<)$_2$;
—COCH$_2$OCH$_2$CONH—C$_6$H$_4$—CH[CH$_2$CON(CH$_2$CH$_2$NH—)$_2$]$_2$;
—COCH$_2$OCH$_2$CONH—C$_6$H$_4$—CH[CH$_2$CON(CH$_2$CH$_2$N<)$_2$]$_2$;
—COCH$_2$CH$_2$CO—NH—C$_6$H$_4$—CH[CH$_2$CON(CH$_2$CH$_2$NH—)$_2$]$_2$;
—COCH$_2$CH$_2$CO—NH—C$_6$H$_4$—CH[CH$_2$CON(CH$_2$CH$_2$N<)$_2$]$_2$;
—CONH—C$_6$H$_4$—CH[CH$_2$CON(CH$_2$CH$_2$NH—)$_2$]$_2$;
—CONH—C$_6$H$_4$—CH[CH$_2$CON(CH$_2$CH$_2$N<)$_2$]$_2$;
—COCH(NH—)CH(COOH)NH—; —COCH(N<)CH(COOH)N<;

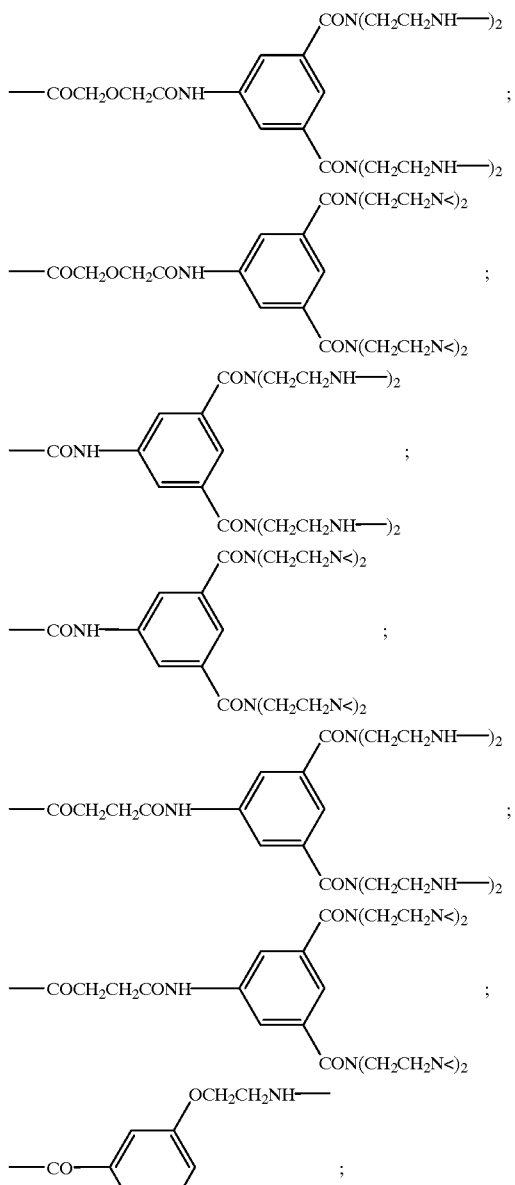

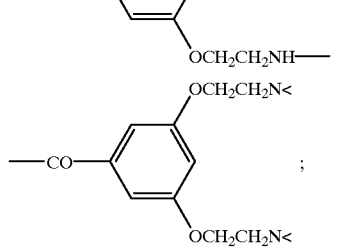

-continued

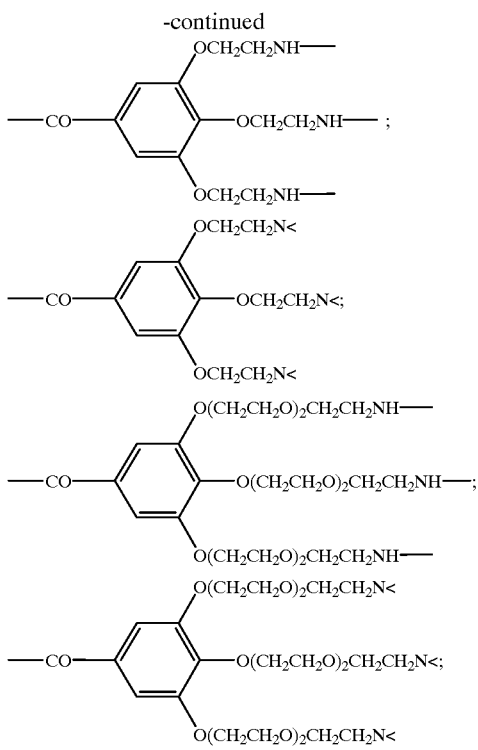

Complexing agent radicals K are described by general formulae IA and IB:

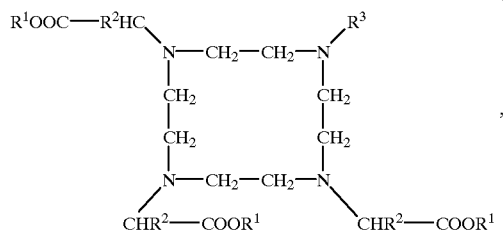

in which

R$^1$ independently of one another, stand for a hydrogen atom or a metal ion equivalent of atomic numbers 20–29, 39, 42–44 or 57–83, R$^2$ stands for a hydrogen atom or a methyl or an ethyl radical which optionally is substituted with 1–2 hydroxy or 1 carboxy group(s), R$^3$ stands for a —CH$_2$—CH(OH)—U$^6$—T or —CH$_2$—CO—U$^7$ group, U$^6$ stands for a straight-chain, branched, saturated or unsaturated C$_1$-C$_{20}$ alkylene group optionally containing 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups; 1–10 oxygen, 1–5 sulfur and/or 1–5 nitrogen atom(s) and/or optionally substituted by 1–5 hydroxy, 1–2 mercapto, 1–5 oxo, 1–5 thioxo, 1–3 carboxy, 1–5 carboxyalkyl, 1–5 ester and/or 1–3 amino group(s), and the phenylene groups that optionally can be contained, can be substituted by 1–2 carboxy, 1–2 sulfo or 1–2 hydroxy groups, U$^7$ stands for a direct bond or radical —NR$^2$—U$^6$—T, T stands for a —CO—α, —NHCO—α or —NHCS—α group, α stands for the bonding site to the terminal nitrogen atoms of the last generation, of reproduction unit W and r stands for numbers 0, 1, 2 or 3.

As preferred complexing agent radicals K, those can be mentioned in which in above-indicated formula IA, the C$_1$-C$_{20}$, and preferably C$_1$-C$_{12}$ alkylene chain that stands for U$^6$ contains a group —CH$_2$—, —CH$_2$NHCO, —NHCOCH$_2$O, —NHCOCH$_2$OC$_6$H$_4$, —N(CH$_2$CO$_2$H), —NHCOCH$_2$C$_6$H$_4$, —NHCSNHC$_6$H$_4$, —CH$_2$OC$_6$H$_4$, —CH$_2$CH$_2$O and/or is substituted by a group —COOH or —CH$_2$COOH.

As examples for U$^6$, the following groups can be cited:

—CH$_2$—, —CH$_2$CH$_2$—, —CH$_2$CH$_2$CH$_2$—, —C$_6$H$_4$—, —C$_6$H$_{10}$—, —CH$_2$C$_6$H$_5$—,

—CH$_2$NHCOCH$_2$CH(CH$_2$CO$_2$H)—C$_6$H$_4$—,

—CH$_2$NHCOCH$_2$OCH$_2$—,

—CH$_2$NHCOCH$_2$C$_6$H$_4$—,

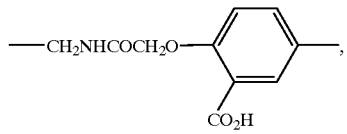

—CH$_2$NHCSNH—C$_6$H$_4$—CH(CH$_2$COOH)CH$_2$—,

—CH$_2$OC$_6$H$_4$—N(CH$_2$COOH)CH$_2$—,

—CH$_2$NHCOCH$_2$O(CH$_2$CH$_2$O)$_4$—C$_6$H$_4$—,

—CH$_2$O—C$_6$H$_4$—,

—CH$_2$CH$_2$—O—CH$_2$CH$_2$—, —CH$_2$CH$_2$—O—CH$_2$CH$_2$—O—CH$_2$CH$_2$—,

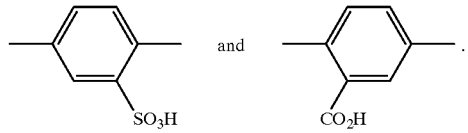

If the agent according to the invention is intended for use in NMR diagnosis, the central ion of the complex salt must be paramagnetic. These are especially the divalent and trivalent ions of the elements of atomic numbers 21–29, 42, 44, and 58–70. Preferred such ions are, for example, the chromium(III), iron(II), cobalt(II), nickel(II), copper(II), praseodymium(III), neodymium(III), samarium(III), and ytterbium(III) ions. Because of their very strong magnetic moment, the gadolinium(III), terbium(III), dysprosium(III), holmium(III), erbium(III), manganese(II), and iron(III) ions are especially preferred.

If the agent according to the invention is intended for use in diagnostic radiology, the central ion has to be derived from an element of higher atomic number in order to achieve sufficient absorption of the x rays. It has been found that for this purpose, diagnostic agents. which contain a physiologically compatible complex salt with central ions of elements of atomic numbers 21–29, 39, 42, 44, and 57–83 are suitable; these are, for example, the lanthanum(III) ion and the above-mentioned ions of the lanthanide series.

The cascade polymer complexes according to the invention contain at least 16 ions of an element of the above-mentioned atomic numbers.

The remaining acid hydrogen atoms, i.e., those which are not substituted by the central ion optionally may be replaced completely or partially by cations of inorganic and/or organic bases, amino acids, or amino acid amides.

Suitable inorganic cations are, for example, the lithium ion, the potassium ion, the calcium ion, the magnesium ion, and especially the sodium ion. Suitable cations of organic bases are, i.a., those of primary, secondary, or tertiary amines, such as, for example, ethanolamine, diethanolamine, morpholine, glucamine, N,N-dimethylglucamine, and especially N-methylglucamine. Suitable cations of amino acids are, for example, those of lysine, arginine, and ornithine, as well as the amides of otherwise acidic or neutral amino acids.

The compounds according to the invention, which have a molecular weight preferably of about 10,000–80,000 D, more preferably 15,000–40,000 D, exhibit the desired properties described above. They contain a large number, required for their use, of metal ions bound in a stable manner in the complex.

They accumulate in regions with high vascular permeability, such as, e.g., in tumors, and thus, they make it possible to make diagnosis regarding the perfusion of tissues, and they provide the possibility of determining the blood volume in tissues, of shortening selectively the relaxation times or densities of the blood, and of graphically representing the permeability of blood vessels. Such physiological data cannot be obtained through the use of conventional extracellular contrast media, such as, e.g., Gd-DTPA [Magnevist®]. From these standpoints, there also follow the use of these agents in the modern imaging processes of nuclear spin tomography and computer tomography: more specific diagnoses of malignant tumors, early therapy monitoring in cases where cytostatic, antiphlogistic, or vasodilative therapy is used, early identification of underperfused regions (e.g., in the myocardium), angiography in vascular diseases, and identification and diagnosis of (sterile or infectious) inflammations.

As further advantages relative to extracellular contrast media, such as, e.g., Gd-DTPA [Magnevist®], the greater effectiveness of the compounds of the invention as contrast media for nuclear spin tomography (higher relaxivity) must be emphasized; this allows a marked reduction of the diagnostically required dose. At the same time, the contrast media according to the invention can be formulated as solutions in an iso-osmotic manner in the blood and thus reduce the osmotic stress of the body, which is reflected in a reduced toxicity on the part of the substance (higher toxic threshold). Smaller doses and higher toxic thresholds result in a significant increase of the reliability of contrast medium use in modern imaging processes.

In comparison with macromolecular contrast media based on carbohydrates, e.g., dextran (European Patent Application, Publication No. 0 326 226), which carry—as mentioned—generally only about 5% of the signal-enhancing paramagnetic cation, the polymer complexes according to the invention exhibit a content of the paramagnetic cation of generally about 20%. Thus, the macromolecules according to the invention produce much better signal enhancement per molecule, which simultaneously has the effect that the dose necessary for nuclear spin tomography is considerably smaller relative to macromolecular contrast media based on carbohydrates.

With the polymer complexes according to the invention, it has been possible to design and produce macromolecules in such a way that the latter have a uniformly defined molecular weight. It is thus possible, surprisingly enough, to control the size of the macromolecules in such a way that the latter are large enough to be able to leave the vascular space only slowly, but at the same time small enough to be able to pass through the capillaries of the kidneys, which are 300–800 Å in size.

In comparison to the other mentioned polymer compounds of the prior art, the cascade polymer complexes according to the invention are distinguished by improved excretion behavior, greater effectiveness, greater stability, and/or better compatibility.

Another advantage of this invention lies in the fact that now complexes with hydrophilic or lipophilic, macrocyclic or open-chain, low-molecular, or high-molecular ligands have become accessible. As a result, the possibility exists for controlling the compatibility and pharmacokinetics of these polymer complexes by chemical substitution.

The production of the cascade polymer complexes according to the invention takes place in that a compound of general formula I'

in which

A stands for a nitrogen-containing cascade nucleus of base multiplicity a,

X and Y, independently of one another, stand for a direct bond or a cascade reproduction unit of reproduction multiplicity x or y, Z and W, independently of one another, stand for a cascade reproduction unit of reproduction multiplicity z or w, a stands for numbers 2 to 12, x, y, z and w, independently of one another, stand for numbers 1 to 4 and β stands for the bonding site of the terminal NH groups of the last generation, of reproduction unit W provided that at least two reproduction units are different and that for the product of multiplicities, $$16 < a \cdot x \cdot y \cdot z \cdot w \leq 64,$$

holds true, is reacted with a complex or a complexing agent K' of general formula I'A or I'B

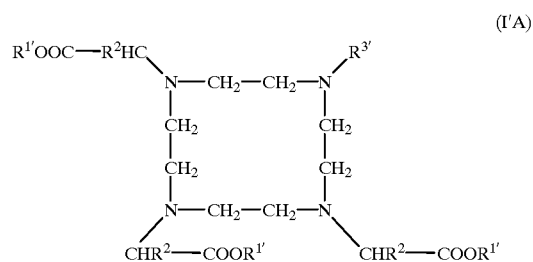

-continued

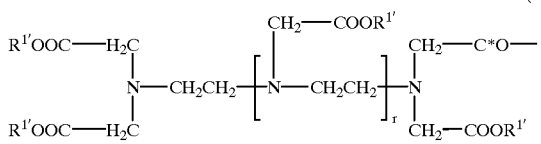
(I'B)

in which
R$^{1'}$ independently of one another, stand for a hydrogen atom, a metal ion equivalent of atomic numbers 20–29, 39, 42–44, or 57–83 or an acid protective group, R$^2$ stands for a hydrogen atom or a methyl or an ethyl radical which optionally is substituted with 1–2 hydroxy or 1 carboxy group(s), R$^{3'}$ stands for a —CH$_2$—CH(OH)—U$^6$—T' or —CH$_2$—CO—U$^{7'}$ group, U$^6$ stands for a straight-chain, branched, saturated or unsaturated C$_1$–C$_{20}$ alkylene group which may optionally contain 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups; 1–10 oxygen, 1–5 sulfur and/or 1–5 nitrogen atom(s) and/or optionally substituted by 1–5 hydroxy, 1–2 mercapto, 1–5 oxo, 1–5 thioxo, 1–3 carboxy, 1–5 carboxyalkyl, 1–5 ester and/or 1–3 amino group(s), and the phenylene groups that may optionally be contained can be substituted by 1–2 carboxy, 1–2 sulfo or 1–2 hydroxy groups, U$^{7'}$ stands for a direct bond or radical —NR$^2$—U$^6$—T', T' stands for a —C*O, —COOH, —N=C=O or —N=C=S group, C*O stands for an activated carboxyl group and r stands for numbers 0, 1, 2 or 3 provided that in the case K stands for a complex at least two (in the case of divalent metals) or at least three (in the case of trivalent metals) of substituents R$^1$ stand for a metal ion equivalent of the above-mentioned elements and that, if desired, other carboxyl groups are present in the form of their salts with inorganic and/or organic bases, amino acids or amino acid amides, are reacted, optionally present protective groups are cleaved, the thus obtained cascade polymers—if K' stands for a complexing agent—are reacted in a way known in the art with at least one metal oxide or metal salt of an element of atomic number 20–29, 39, 42, 44, or 57–83 and then optionally in the cascade polymer complexes thus obtained, acid hydrogen atoms that are still present are completely or partially substituted by cations of inorganic and/or organic bases, amino acids, or amino acid amides.

As an example of an activated carbonyl group C*O in complexes or complexing agents K', anhydride, p-nitrophenyl ester, N-hydroxysuccinimide ester, pentafluorophenyl ester, and acid chloride can be mentioned.

The addition or acylation reaction that is carried out to introduce the complex or complexing agent units is performed with substrates that contain desired substituents K (optionally bound to a leaving group) or from which the desired substituent is generated by the reaction.

As examples of addition reactions, the reaction of isocyanates and isothiocyanates can be mentioned, in which the reaction of isocyanates is preferably performed in aprotic solvents, such as, e.g., THF, dioxane, DMF, DMSO, methylene chloride at temperatures preferably of about 0–100° C., more preferably of 0–50° C., optionally with the addition of an organic base such as triethylamine, pyridine, lutidine, N-ethyldiisopropylamine, N-methylmorpholine. The reaction with isothiocyanates is generally performed in solvents, such as, e.g., water or lower alcohols, such as, e.g., methanol, ethanol, isopropanol or their mixtures, DMF or mixtures of DMF and water at temperatures preferably of about 0–100° C., more preferably of 0–50° C., optionally with the addition of an organic or inorganic base, such as, e.g., triethylamine, pyridine, lutidine, N-ethyldiisopropylamine, N-methylmorpholine, or alkaline earth hydroxides, alkali hydroxides, such as, e.g., lithium, sodium, potassium, calcium hydroxide, or their carbonates, such as, e.g, magnesium carbonate.

As examples of acylation reactions, the reaction of free carboxylic acids according to the methods known to one skilled in the art [e.g., J. P. Greenstein, M. Winitz, Chemistry of the Amino Acids, John Wiley & Sons, N.Y. (1961), pp. 943–945) can be mentioned. It has proven advantageous, however, to convert the carboxylic acid group before the acylation reaction to an activated form, such as, e.g., anhydride, active ester or acid chloride [e.g., E. Gross, J. Meienhofer, The Peptides, Academic Press, N.Y. (1979), Vol. 1, pp. 65–314; N. F. Albertson, Org. React. 12, 157 (1962)].

As examples of the reaction of anhydrides, the reaction of monoanhydride N$^3$-(2,6-dioxomorpholinoethyl)-N$^6$-(ethoxycarbonylmethyl)-3,6-diazaoctanedioic acid with the cascade polymers which are desired in each case and which contain terminal amino groups, in water, in polar solvents, such as, e.g., dioxane, THF, DMF, DMSO, or acetonitrile or their mixtures at basic pH, preferably 8–10, i.e., with the addition of bases, such as, e.g., sodium hydroxide, potassium hydroxide, triethylamine, or pyridine, at temperatures preferably of about 0–50° C., more preferably at room temperature, can be mentioned. For complete reaction in water, the operation is preferably performed with, e.g., a 2- to 3-fold excess of monoanhydride.

In the case of reaction with active ester, the literature known to one skilled in the art [e.g., Houben-Weyl, Methoden der organischen Chemie [Methods of Organic Chemistry], Georg Thieme Verlag, Stuttgart, Volume E 5 (1985), 633] can be cited. This reaction can be performed under the conditions indicated above for the anhydride reaction. However, aprotic solvents, such as, e.g., methylene chloride, chloroform, can also be used.

In the case of acid chloride reactions, only aprotic solvents, such as, e.g., methylene chloride, chloroform, toluene or THF, at temperatures between –20 to 50° C., preferably between 0 to 30° C., are used. Further, literature known to one skilled in the art [e.g., Houben-Weyl, Methoden der Organischen Chemie, Georg-Thieme-Verlag, Stuttgart, (1974), Volume 15/2, pp. 355–364] can be cited.

If R$^{1'}$ stands for an acid protective group, lower alkyl, aryl and aralkyl groups, for example, the methyl, ethyl, propyl, butyl, phenyl, benzyl, diphenylmethyl, triphenylmethyl, bis-(p-nitrophenyl)-methyl groups, as well as trialkylsilyl groups, are suitable.

The optionally desired cleavage of the protective groups takes place according to the processes known to one skilled in the art, for example by hydrolysis, hydrogenolysis, alkaline saponification of esters with alkali in aqueous-alcoholic solution at temperatures preferably of about 0° C. to 50° C. or in the case of tert-butyl esters with the aid of trifluoroacetic acid.

Terminal amino groups, optionally incompletely acylated with ligands or complexes, can, if desired, be converted to amides or partial amides, for example, by reaction with acetic anhydride, succinic anhydride or diglycolic anhydride.

The introduction of the desired metal ions takes place in the way in which it was disclosed in German laid-open specification 34 01 052, by the metal oxide or a metal salt (for example, the nitrate, acetate, carbonate, chloride or sulfate) of the element of atomic numbers 20–29, 42, 44, 57–83 being dissolved or suspended in water and/or a lower alcohol (such as methanol, ethanol or isopropanol) and being reacted with the solution or suspension of the equivalent amount of complexing ligand and then, if desired, existing acid hydrogen atoms of the acid groups being substituted by cations of inorganic and/or organic bases, amino acids or amino acid amides.

The introduction of the desired metal ions can take place both in the stage of complexing agent I'A or I'B, i.e., before the coupling to the cascade polymers, or after coupling of unmetalated ligands I'A or I'B.

The neutralization takes place with the aid-of inorganic bases (for example, hydroxides, carbonates or bicarbonates) of, for example, sodium, potassium, lithium, magnesium or calcium and/or organic bases, such as, i.a., primary, secondary and tertiary amines, such as, for example, ethanolamine, morpholine, glucamine, N-methyl and N,N-dimethylglucamine, as well as basic amino acids, such as, for example, lysine, arginine and ornithine or of amides of originally neutral or acid amino acids, such as, for example, hippuric acid, glycine acetamide.

For the production of neutral complex compounds, enough of the desired bases can be added, for example, to the acid complex salts in aqueous solution or suspension that the neutral point is reached. The obtained solution can then be evaporated to dryness in a vacuum. Often, it is advantageous to precipitate the formed neutral salts by adding water-miscible solvents, such as, for example, lower alcohols (methanol, ethanol, isopropanol and others), lower ketones (acetone and others), polar ethers (tetrahydrofuran, dioxane, 1,2-dimethoxyethane and others) and thus to obtain easily isolated and readily purified crystallizates. It has proven especially advantageous to add the desired bases as early as during the complexing of the reaction mixture to thus save a process step.

If the acid complex compounds contain several free acid groups, it is often suitable to produce neutral mixed salts, which contain both inorganic and organic cations.

This can happen, for example, by reacting the complexing ligands in aqueous suspension or solution being reacted with the oxide or salt of the element yielding the central ion and half of the amount of an organic base required for neutralization, the formed complex salt being isolated, optionally purified and then mixed with the required amount of inorganic base for complete neutralization. The sequence of the addition of base can also be reversed.

The purification of the thus obtained cascade polymer complexes takes place, optionally after adjusting the pH to 6 or 8, preferably about 7, by adding an acid or base, preferably by ultrafiltration with membranes of suitable pore size (e.g., Amicon®XM30, Amicon®YM10, Amicon®YM3) or gel filtration on, e.g., suitable Sephadex® gels.

The production of the cascade polymers carrying terminal amino groups required for the coupling to complexing agents K' (or else the corresponding metal-containing complexes) generally proceeds from nitrogen-containing cascade starters $A(H)_a$ that can be produced by commercially available methods or according to or analogously to methods known in the literature. The introduction of generations X, Y, Z and W takes place according to methods known in the literature [e.g., J. March, Advanced Organic Chemistry, 3rd ed.; John Wiley & Sons, (1985), 364–381] by acylation or alkylation reactions with protected amines exhibiting the desired structures, which contain functional groups capable of bonding to the cascade nuclei, such as, e.g., carboxylic acids, isocyanates, isothiocyanates or activated carboxylic acids (such as, e.g., anhydrides, active esters, acid chlorides) or halides (such as, e.g., chlorides, bromides, iodides), aziridine, mesylates, tosylates or other leaving groups known to one skilled in the art.

It can be stressed, however, that the differentiation between cascade nucleus A and reproduction units is purely formal. It can be advantageous synthetically that a formal cascade starter $A(H)_a$ is not used, but rather the nitrogen atoms forming part of the cascade nucleus by definition are introduced first together with the first generation. Thus, e.g., for synthesis of the compound described in Example 1b), it is more advantageous not to alkylate the formal cascade nucleus trimesic acid triamide with e.g., benzyloxycarbonylaziridine (six-fold), but to react trimesic acid trichloride with bis[2-(benzyloxycarbonylamino)-ethyl]-amine (three-fold).

As amino protective groups, the benzyloxycarbonyl, tert-butoxycarbonyl, trifluoroacetyl, fluorenylmethoxycarbonyl, benzyl and formyl groups familiar to one skilled in the art [Th. W. Greene, P. G. M. Wuts, Protective Groups in Organic Syntheses, 2nd ed, John Wiley and Sons (1991), pp. 309–385], can be mentioned. After cleavage of these protective groups, which also can take place according to methods known in the literature, the next desired generation can be introduced into the molecule. In addition to this synthesis of a generation consisting of two reaction stages in each case (alkylation or acylation and protective group cleavage), the simultaneous introduction of two, e.g., $X-[Y]_x$, or several generations, e.g., $X-[Y-(Z)_y]_x$, is also possible with only two reaction stages. The synthesis of these multi-generation units takes place by alkylation or acylation of unprotected amines ("reproduction amine"), exhibiting the structures of the desired reproduction units, with a second reproduction amine, whose amine groups are present in protected form.

The compounds of general formula $A(H)_a$ required as cascade starters are commercially available or can be produced according to or analogously to methods known in the literature [e.g., Houben-Weyl, Methoden der Org. Chemie, Georg-Thieme-Verlag, Stuttgart (1957), Vol. 11/1; M. Micheloni et al., Inorg. Chem. (1985), 24, 3702; T. J. Atkins et al., Org. Synth., Vol. 58 (1978), 86–98; The Chemistry of Heterocyclic Compounds: J. S. Bradshaw et al., Aza-Crown-Macrocycles, John Wiley & Sons, N.Y. (1993)]. As examples, there can be cited:

Tris(aminoethyl)amine [e.g., Fluka Chemie [Fluka Chemistry] AG, Switzerland; Aldrich-Chemie [Aldrich Chemistry], Germany];

tris(aminopropyl)amine [e.g., C. Woerner et al., Angew. Chem. [Applied Chem.] Int. Ed. Engl. (1993), 32, 1306];

diethylenetriamine [e.g., Fluka; Aldrich];

triethylenetetramine [e.g., Fluka; Aldrich];

tetraethylenepentamine [e.g., Fluka; Aldrich];

1,3,5-tris(aminomethyl)benzene [e.g., T. M. Garrett et al., J. Am. Chem. Soc. (1991), 113, 2965];

trimesic acid triamide [e.g., H. Kurihara; Jpn. Kokai Tokyo Koho JP 04077481; CA 117, 162453];

1,4,7-triazacyclononane [e.g., Fluka; Aldrich];

1,4,7,10,13-pentaazacyclopentadecane [e.g., K. W. Aston, Eur. Pat. Appl. 0 524 161, CA 120, 44580];

1,4,8,11-tetraazacyclotetradecane [e.g., Fluka; Aldrich];

1,4,7,10,13,16,19,22,25,28-Decaazacyclotriacontane [e.g., A. Andres et al., J. Chem. Soc. Dalton Trans. (1993), 3507];

1,1,1-tris(aminomethyl)ethane [e.g., R. J. Geue et al., Aust. J. Chem. (1983), 36, 927];

tris(aminopropyl)-nitromethane [e.g., G. R. Newkome et al., Angew. Chem. 103, 1205 (1991) analogously to R. C. Larock, Comprehensive Organic Transformations, VCH Publishers, N.Y. (1989), 419–420]

1,3,5,7-adamantanetetracarboxylic acid amide [e.g., H. Stetter et al., Tetr. Lett. 1967, 1841];

1,2-bis[phenoxyethane]-3',3",5',5"-tetracarboxylic acid amide [e.g., J. P. Collman et al.; J. Am. Chem. Soc. (1988), 110, 3477–86 analogously to the instructions for Example 1b)];

1,4,7,10,13,16,21,24-octaazabicyclo[8.8.8]hexacosane [e.g., P. H. Smith et al., J. Org. Chem. (1993), 58, 7939].

The production of the reproduction amines containing the above-mentioned functional groups required for the synthesis of generations takes place according to or analogously to the instructions described in the experimental part or according to processes known in the literature.

As examples, there can be mentioned:

$N^{\alpha},N^{\varepsilon}$—Di—CO—O—CH$_2$C$_6$H$_5$-lysine-p-nitrophenyl ester [see instructions for Example 1c)];

HOOC—CH$_2$OCH$_2$CO—N(CH$_2$CH$_2$NH—CO—O—CH$_2$C$_6$H$_5$)$_2$ [see instructions for Example 7a)];

HOOC—CH$_2$N(CH$_2$CH$_2$NH—CO—O—CH$_2$C$_6$H$_5$)$_2$ [see instructions for Example 9e)];

HOOC—CH$_2$CH$_2$CO—N(CH$_2$CH$_2$NH—COCF$_3$)$_2$ [to be produced according to instructions for Example 7a), by starting from bis(trifluoroacetylaminoethyl)amine instead of bis(benzyloxycarbonylaminoethyl)amine and from succinic anhydride instead of diglycolic anhydride];

HOOC—CH$_2$OCH$_2$CONH—C$_6$H$_4$—CH[CH$_2$CON(CH$_2$CH$_2$NH—CO—O—CH$_2$C$_6$H$_5$)$_2$]$_2$ [to be produced according to instructions for Example 7a), by starting from the amine described in Example 9b) instead of bis(benzyloxycarbonylaminoethyl)amine];

O=C=N—C$_6$H$_4$—CH[CH$_2$CON(CH$_2$CH$_2$NH—CO—O—CH$_2$C$_6$H$_5$)$_2$]$_2$ [see instructions for Example 9c)]

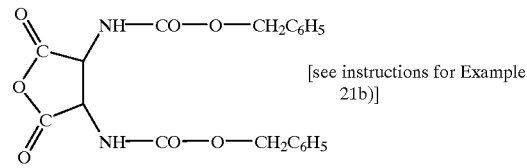

[see instructions for Example 21b)]

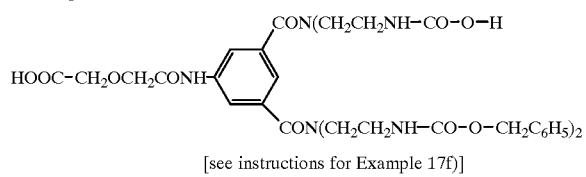

[see instructions for Example 17f)]

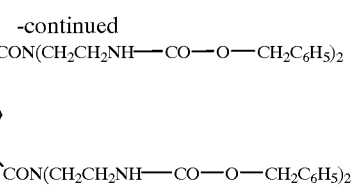

to be produced according to instructions for Example 17f), by being reacted with triphosgene, instead of diglycolic anhydride, analogously to the instructions for Example 9c)

N-benzyloxycarbonyl-aziridine see instructions for example 15a)

N-benzyloxycarbonyl-glycine commercially available in, e.g., Bachem, Calif.

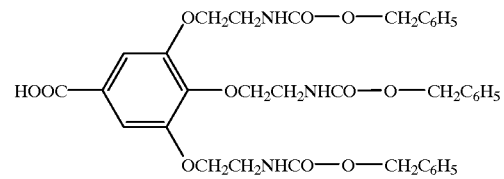

to be produced according to C. J. Cavallito et al., J. Amer. Chem. Soc. 1943, 65, 2140, by starting from N—CO—O—CH$_2$C$_6$H$_5$—(2-bromoethyl) amine instead of benzyl chloride [A. R. Jacobson et al., J. Med. Chem. (1991), 34, 2816].

The production of the complexes and complexing agents of general formula I'A and I'B takes place according to or analogously to the instructions described in the experimental part or according to methods known in the literature (see, e.g., European Patent Applications Nos. 0 512 661, 0 430 863, 0 255 471 and 0 565 930.

The production of the pharmaceutical agents according to the invention takes place also in a way known in the art, by the complex compounds according to the invention—optionally with the addition of the additives usual in galenicals—being suspended or dissolved in aqueous medium and then the suspension or solution optionally being sterilized. Suitable additives are, for example, physiologically harmless buffers (such as, for example, tromethamine), additives of complexing agents or weak complexes (such as, for example, diethylenetriamine-pentaacetic acid or the corresponding Ca-cascade polymer complexes) or—if necessary—electrolytes, such as, for example, sodium chloride or—if necessary—antioxidants, such as, for example, ascorbic acid.

If suspensions or solutions of the agents according to the invention in water or physiological salt solution are desired for enteral administration or other purposes, they are mixed with one or more adjuvant(s) usual in galenicals [for example, methylcellulose, lactose, mannitol] and/or surfactant(s) [for example, lecithins, Tween®, Myrj®] and/or flavoring substance(s) for taste correction [for example, ethereal oils].

In principle, it is also possible to produce the pharmaceutical agents according to the invention even without isolating the complex salts. In any case, special care must be used to undertake the chelation so that the salts and salt solutions according to the invention are practically free of noncomplexed metal ions having a toxic effect.

This can be assured, for example, with the aid of color indicators such as xylenol orange by control titrations during the production process. The invention therefore also relates to processes for the production of complex compounds and their salts. As a last precaution, there is a purification of the isolated complex salt.

The pharmaceutical agents according to the invention contain preferably about 1 μmol-1 mol/l of the complex salt and are preferably dosed in amounts of about 0.0001–5 mmol/kg. They are intended for enteral and parenteral administration. The complex compounds according to the invention are used 1. for NMR diagnosis and diagnostic radiology in the form of their complexes with the ions of elements with atomic numbers 21–29, 39, 42, 44 and 57–83;
2. for radiodiagnosis and radiotherapy in the form of their complexes with radioisotopes of the elements with atomic numbers 27, 29, 31, 32, 37–39, 43, 49, 62, 64, 70, 75 and 77.

The agents according to the invention meet the varied requirements for suitability as contrast media for nuclear spin tomography. Thus, they are very well suited, after oral or parenteral administration, for improving the image, obtained with the aid of nuclear spin tomographs, in its informative value by increasing the signal intensity. Further, they show the great effectiveness which is necessary to load the body with the fewest possible amounts of foreign substances, and the good compatibility which is necessary to maintain the noninvasive nature of the studies.

The good water solubility and low osmolality of the agents according to the invention makes it possible to produce highly concentrated solutions, so that the volume load of the circulatory system can be held within reasonable limits and to compare the dilution through the bodily fluid, i.e., NMR diagnostic agents must be 100- to 1000-fold better water-soluble than for NMR spectroscopy. Further, the agents according to the invention exhibit not only a high stability in vitro, but also a surprisingly high stability in vivo, so that a release or an exchange of the ions—toxic in themselves—not covalently bound in the complexes, in which the new contrast media are again completely excreted, takes place only extremely slowly.

In general, the agents according to the invention for use as NMR diagnostic agents are dosed in amounts of 0.0001–5 mmol/kg, preferably 0.005–0.5 mmol/kg. Details of use are discussed, for example, in H. -J. Weinmann et al., Am. J. of Roentgenology 142, 619 (1984).

Especially low dosages (under 1 mg/kg of body weight) of organ-specific NMR diagnostic agents can be used, for example, to detect tumors and myocardial infarction.

Further, the complex compounds according to the invention are used advantageously as susceptibility reagents and as shift reagents for in vivo NMR spectroscopy.

The agents according to the invention are also suitable as radiodiagnostic agents because of their advantageous radioactive properties and the good stability of the complex compounds contained in them. Details of their use and dosage are described, e.g., in "Radiotracers for Medical Applications," CRC Press, Boca Raton, Fla.

Another imaging method with radioisotopes is positron emission tomography, the positron-emitting isotopes, such as, e.g., $^{43}$Sc, $^{44}$Sc, $^{52}$Fe, $^{55}$Co and $^{68}$Ga (Heiss, W. D.; Phelps, M. E.; Positron Emission Tomography of the Brain, Springer Verlag Berlin, Heidelberg, N.Y. 1983).

Since the substances according to the invention are concentrated in malignant tumors (no diffusion in healthy tissue, but high permeability of tumor vessels), they can also assist in the radiation therapy of malignant tumors. The latter is distinguished from the corresponding diagnosis only by the amount and type of the isotope used. The object, in this case, is the destruction of tumor cells by high-energy shortwave radiation with a smallest possible range of action. For this purpose, interactions of the metals contained in the complexes (such as, e.g., iron or gadolinium) are used with ionizing radiations (e.g., x rays) or with neutron rays. By this effect, the local radiation dose is significantly increased on the spot where the metal complex is found (e.g., in tumors). To produce the same radiation dose in the malignant tissue, the radiation exposure for healthy tissue can be considerably reduced with the use of such metal complexes and thus side effects that are stressful to the patients are avoided. The metal complex conjugates according to the invention are therefore suitable as radiosensitizing substances in radiation therapy of malignant tumors (e.g., use of Mössbauer effects or in neutron capture therapy). Suitable β-emitting ions are, for example, $^{46}$Sc, $^{47}$Sc, $^{48}$Sc, $^{72}$Ga, $^{73}$Ga and $^{90}$Y. Suitable α-emitting ions exhibiting small half-lives are, for example, $^{211}$Bi, $^{212}$Bi, $^{213}$Bi and $^{214}$Bi, and $^{212}$Bi is preferred. A suitable photon- and electron-emitting ion is $^{158}$Gd, which can be obtained from $^{157}$Gd by neutron capture.

If the agent according to the invention is intended for use in the variant of radiation therapy proposed by R. L. Mills et al. (Nature Vol. 336, (1988), p. 787), the central ion must be derived from a Mössbauer isotope, such as, for example, $^{57}$Fe or $^{151}$Eu.

In the in vivo administration of the therapeutic agents according to the invention, the latter can be administered together with a suitable vehicle, such as, for example, serum, or physiological common salt solution and together with another protein, such as, for example, human serum albumin. In this case, the dosage depends on the type of cellular disorder, the metal ion used and the type of imaging method.

The therapeutic agents according to the invention are administered parenterally, preferably i.v.

Details of use of radiotherapeutic agents are discussed, e.g., in R. W. Kozak et al. TIBTEC, October 1986, 262.

The agents according to the invention are very well suited as x-ray contrast media, and it is especially to be emphasized that no signs of the anaphylaxis-like reactions, known from the iodine-containing contrast media, can be detected in biochemical-pharmacological studies. They are especially valuable because of the advantageous absorption properties in the areas of higher tube voltages for digital subtraction techniques.

In general, the agents according to the invention are dosed for use as x-ray contrast media analogously to, for example, meglumine-diatrizoate in amounts preferably of about 0.1–5 mmol/kg, more preferably 0.25–1 mmol/kg.

Details of use of x-ray contrast media are discussed, for example, in Barke, Röntgenkontrastmittel [X-Ray Contrast Media], G. Thieme, Leipzig (1970) and P. Thurn, E. B ücheler "Einführung in die Röntgendiagnostik [Introduction to Diagnostic Radiology]," G. Thieme, Stuttgart, N.Y. (1977).

In general, it has been possible to synthesize new complexing agents, metal complexes and metal complex salts, which open up new possibilities in diagnostic and therapeutic medicine.

In the foregoing and in the following examples, all temperatures are set forth uncorrected in degrees Celsius; and, unless otherwise indicated, all parts and percentages are be weight.

The entire disclosure of all applications, patents and publications, cited above and below, and of corresponding German application No. P 44 225 857.7, filed Jul. 7, 1994, is hereby incorporated by reference.

EXAMPLES

The following examples are used for a more detailed explanation of the object of the invention and the invention is not limited thereto:

Example 1 a) Bis[2-(benzyloxycarbonylamino)-ethyl]-amine 51.5 g (500 mmol) of diethylenetriamine and 139 ml (1 mol) of triethylamine are dissolved in dichloromethane and mixed at −20° C. with 161 g of benzyl cyanoformate (Fluka) in dichloromethane and then stirred overnight at room temperature. After completion of the reaction, concentration by evaporation is performed during draw-off, the residue is taken up in diethyl ether, the organic phase is washed with sodium carbonate solution and dried with sodium sulfate. The filtrate is mixed with hexane, the precipitate is filtered off and dried.

Yield: 163.4 g (88% of theory)
Elementary analysis:
Cld: C, 64.67; H, 6.78; N, 11.31.
Fnd: C, 64.58; H, 6.83; N, 11.28.

b) N,N,N',N',N",N"-Hexakis[2-(benzyloxycarbonylamino)-ethyl]-trimesic acid triamide 13.27 g (50 mmol) of trimesic acid trichloride (Aldrich) and 34.7 ml (250 mmol) of triethylamine are dissolved in dimethylformamide (DMF) and mixed at 0° C. with 65.0 g (175 mmol) of the amine described in Example 1a and then stirred overnight at room temperature. The solution is concentrated by evaporation in a vacuum, and the residue is chromatographed with ethyl acetate on silica gel.

Yield: 39.4 g (62% of theory)
Elementary analysis:
Cld: C, 65.24; H, 5.95; N, 9.92.
Fnd: C, 65.54; H, 5.95; N, 9.87.

c) $N^{\alpha}, N^{\epsilon}$-Bis(N,N'-dibenzyloxycarbonyl-lysyl)-lysine, protected "trilysine"

3.6 g (20 mmol) of lysine-hydrochloride and 6.95 ml (50 mmol) of triethylamine are dissolved in DMF, mixed with 26.8 g (50 mmol) of $N^{\alpha},N^{\epsilon}$-dibenzyloxycarbonyl-lysine-p-nitrophenylester (Bachem) and stirred for 2 days at room temperature. After completion of the reaction, it is concentrated by evaporation in a vacuum, the residue is taken up in ethyl acetate and shaken out with diluted hydrochloric acid. The organic phase is dried with sodium sulfate, the solvent is concentrated by evaporation and the residue is chromatographed with ethyl acetate/ethanol in a step gradient.

Yield: 10.7 g (57% of theory)
Elementary analysis:
Cld: C, 63.95; H, 6.65; N, 8.95.
Fnd: C, 63.63; H, 6.69; N, 8.93.

d) Completely protected benzyloxycarbonyl-24-polyamine based on N,N,N',N',N",N"-hexakis[2-(trilysyl-amino)-ethyl]-trimesic acid triamide 1.27 g (1 mmol) of the hexa-benzyloxycarbonylamine described in Example 1b is dissolved in glacial acetic acid and mixed with stirring with 33% hydrogen bromide in glacial acetic acid. After 60 minutes, the incipient precipitation is completed with diethyl ether, the hexa-amine-hydrobromide produced is washed with ether, dried in a vacuum and used without further purification in the reaction further described below.

Yield: 0.95 g (quantitative)

7.0 g (7.5 mmol) of the protected "trilysine" described in Example 1c, 1.2 g (7.5 mmol) of 1-hydroxybenzotriazole and 2.4 g (7.5 mmol) of 2-(1H-benzotriazol-1-yl)-1,1,3,3-tetramethyluronium tetrafluoroborate (TBTU; Peboc Limited, UK) are dissolved in DMF and stirred for 15 minutes. This solution is then mixed with 5.16 ml (30 mmol) of N-ethyldiisopropylamine and with 0.95 g (1 mmol) of the above-described hexa-amine-hydrobromide and stirred overnight at room temperature. After completion of the reaction, it is concentrated by evaporation in a vacuum and the residue is chromatographed with ethyl acetate/ethanol (2:1) on silica gel.

Yield: 4.55 g (76% of theory)
Elementary analysis:
Cld: C, 64.35; H, 6.71; N, 10.52.
Fnd: C, 64.08; H, 6.57; N, 10.29.

e) 24-Gadolinium-DTPA-monoamide based on N,N,N',N',N",N"-hexakis[2-trilysylamino)-ethyl]-trimesic acid triamide 1.20 g (0.2 mmol) of the poly-benzyloxycarbonylamine described in Example 1d is dissolved in glacial acetic acid and mixed with stirring with 33% hydrogen bromide in glacial acetic acid. After 3 hours, the incipient precipitation is completed with diethyl ether, the 24-amine-hydrobromide produced is washed with ether and dried in a vacuum. The residue is then taken up in water and adjusted to pH 9.5 by adding 1 N sodium hydroxide solution. 5.8 g (14.4 mmol) of $N^3$-(2,6-dioxomorpholinoethyl)-$N^6$-(ethoxycarbonylmethyl)-3,6-diazaoctanedioic acid (Example 13a of EP 0331 616) is added in solid form in this solution, and the pH is kept constant at 9.5 by further addition of sodium hydroxide solution. After completion of the addition, it is adjusted with 5 N sodium hydroxyide solution to pH>13 for saponification of the DTPA-ethyl ester, and it is stirred overnight at room temperature. Then, it is adjusted to pH 5 with concentrated hydrochloric acid, mixed with 2.61 g (7.2 mmol) of $Gd_2O_3$, stirred for 30 minutes at 80° C., adjusted to pH 7 after the cooling and desalinated with a YM3 AMICON-ultrafiltration membrane. The retentate is finally membrane-filtered and freeze-dried.

Yield: 3.31 g (94.6% of theory)
$H_2O$ content (Karl Fischer): 8.5%
Gd-determination (AAS): 22.9%
Elementary analysis (relative to anhydrous substance):
Cld: C, 34.89; H, 4.17; Gd, 23.57; N, 10.24; Na, 3.45.
Fnd: C, 35.26; H, 4.32; Gd, 22.82; N, 10.56; Na, 3.14.

The ytterbium complex is analogously obtained with $Yb_2O_3$:

Elementary analysis (relative to anhydrous substance):
Cld: C, 34.08; H, 4.08; Yb, 25.34; N, 10.00; Na, 3.37.
Fnd: C, 33.90; H, 4.22; Yb, 25.06; N, 9.83; Na, 3.13.

Example 2 a) 10-[5-(2-Carboxyphenyl)-2-hydroxy-5-oxo-4-azapentyl]-1,4,7-tris(carboxymethyl)-1,4,7,10-tetraazacyclododecane 50 g (144.3 mmol) of 1,4,7-tris(carboxymethyl)-1,4,7,10-tetraazacyclododecane (D03A) is dissolved in 250 ml of water and the pH is adjusted to 13 with 5 N sodium hydroxide solution. Then, a solution of 38.12 g (187.6 mmol) of N(2,3-epoxypropyl)-phthalamide in 100 ml of dioxane is instilled within one hour, stirred for 24 hours at 50° C. and the pH is kept at 13 by adding 5 N sodium hydroxide solution. The solution is adjusted to pH 2 with 10% hydrochloric acid and evaporated to dryness in a vacuum. The residue is dissolved in some water and purified on an ion-exchange column (Reillex®=poly-(4-vinyl)-pyridine (it is eluted with water). The main fractions are concentrated by evaporation in a vacuum and the residue is given a final purification by chromatography on RP-18 (LiChroPrep®/mobile solvent: gradient of tetrahydrofuran/methanol/water). After concentration by evaporation of the main fractions, 63.57 g (71% of theory) of an amorphous solid is obtained.

Water content: 8.5%

Analysis (relative to anhydrous substance):

Cld: C, 52.90; H, 6.57; N, 12.34.

Fnd: C, 52.65; H, 6.68; N, 12.15.

b) 10-(3-Amino-2-hydroxy-propyl)-1,4,7-tris(carboxymethyl)-1,4,7,10-tetraazacyclododecane 50 g (88.1 mmol) of the title compound of Example 2a is refluxed in 300 ml of concentrated hydrochloric acid for 24 hours. It is evaporated to dryness, the residue is dissolved in some water and purified on an ion-exchange column (Reillex®=poly-(4-vinyl)pyridine (it is eluted with water). The main fractions are evaporated to dryness.

Yield: 39.0 g (95% of theory) of a vitreous solid

Water content: 10.3%

Elementary analysis (relative to anhydrous substance):

Cld: C, 48.68; H, 7.93; N, 16.70.

Fnd: C, 48.47; H, 8.09; N, 16.55.

c) Gadolinium complex of 10-(3-amino-2-hydroxypropyl)-1,4,7-tris(carboxymethyl)-1,4,7,10-tetraazacyclododecane 38 g (90.6 mmol) of the title compound of Example 2b is dissolved in 300 ml of water and 16.42 g (45.3 mmol) of gadolinium oxide is added. It is heated for 3 hours to 90° C. The cooled solution is stirred with 5 ml each of acid ion exchanger (IR-120/H$^+$form) and 5 ml of basic exchanger (IRA-410/OH$^-$form) for one hour at room temperature. It is filtered off from the exchanger. Freeze drying of the filtrate yields 57.23 g (98% of theory) of an amorphous solid.

Water content: 11.3%

Analysis (relative to anhydrous substance):

Cld: C, 35.59; H, 5.27; Gd, 27.41; N, 12.21.

Fnd: C, 35.32; H, 5.38; Gd, 27.20; N, 12.31.

d) Gadolinium complex of 10-[7-(4-nitrophenyl)-2-hydroxy-5-oxo-7-(carboxymethyl)-4-aza-heptyl]-1,4,7-tris(carboxymethyl)-1,4,7,10-tetraazacyclododecane 9.84 g (41.8 mmol) of 3-(4-nitrophenyl)-glutaric anhydride is added to 20 g (34.86 mmol) of the title compound of example 2c in 200 ml of dimethylformamide/20 ml of triethylamine (Journal of Org. Chem., Vol. 26, 3856 (1961)) and stirred overnight at room temperature. It is evaporated to dryness in a vacuum. The residue is recrystallized from isopropanol/acetic acid 95:5.

Yield: 27.46 g (94% of theory) of a yellowish solid

Water content: 3.4%

Analysis (relative to anhydrous substance):

Cld: C, 41.58; H, 4.86; Gd, 19.44; N, 10.39.

Fnd: C, 41.38; H, 4.97; Gd, 19.28; N, 10.17.

e) Gadolinium complex of 10-[7-(4-aminophenyl)-2-hydroxy-5-oxo-7-(carboxymethyl)-4-aza-heptyl]-1,4,7-tris(carboxymethyl)-1,4,7,10-tetraazacyclododecane 25 g (30.9 mmol) of the title compound of Example 2d is dissolved in 250 ml of methanol and 5 g of palladium catalyst (10% Pd on C) is added. It is hydrogenated overnight at room temperature. The catalyst is filtered off and the filtrate is evaporated to dryness in a vacuum.

Yield: 24.07 g (97% of theory) of a cream-colored solid

Water content: 3.0%

Analysis (relative to anhydrous substance):

Cld: C, 43.18; H, 5.31; Gd, 20.19; N, 10.79.

Fnd: C, 43.27; H, 5.48; Gd, 20.02; N, 10.61.

f) Gadolinium complex of 10-[7-(4-isothiocyanatophenyl)-2-hydroxy-5-oxo-7-(carboxymethyl)-4-aza-heptyl]-1,4,7-tris(carboxymethyl)-1,4,7,10-tetraazacyclododecane 15 g (19.26 mmol) of the title compound of Example 2e is dissolved in 100 ml of water and 6.64 g (57.8 mmol) of thiophosgene in 50 ml of chloroform is added. It is stirred for 1 hour at 50° C. It is cooled to room temperature, the organic phase is separated and the aqueous phase is shaken out twice with 100 ml of chloroform. The aqueous phase is evaporated to dryness, and the residue is absorptively precipitated in 100 ml of isopropanol at room temperature. The solid is filtered off and washed with ether. After drying overnight in a vacuum (40° C.), 15.9 g (98% of theory) of a cream-colored solid is obtained.

Water content: 3.5%

Analysis (relative to anhydrous substance):

Cld: C, 42.43; H, 4.79; Gd, 19.15; N, 10.24; S, 3.91.

Fnd: C, 42.23; H, 4.90; Gd, 19.01; N, 10.05; S, 3.96.

g) 24-Thiourea conjugate of the Gd complex of 10-[7-(4-isothiocyanatophenyl)-2-hydroxy-5-oxo-7-(carboxymethyl)-4-aza-heptyl]-1,4,7-tris(carboxymethyl)-1,4,7,10-tetraazacyclododecane with the 24-amine N,N,N',N',N'',N''-hexakis[2-(trilysylamino)-ethyl]-trimesic acid triamide 1.20 g (0.2 mmol) of the 24-benzyloxycarbonylamine described in Example 1d is dissolved in glacial acetic acid and mixed with stirring with 33% hydrogen bromide in glacial acetic acid. After 3 hours, the incipient precipitation is completed with diethyl ether, the 24-amine-hydrobromide produced is washed with ether and dried in a vacuum.

The residue is then taken up in water and adjusted to pH 9.5 by adding 1 N sodium hydroxide solution. 6.08 g (7.2 mmol) of the isothiocyanate, described in Example 2f above, in solid form is added in portions to this solution, and the pH is kept constant at 9.5 by further addition of sodium hydroxide solution. After completion of the addition, it is stirred overnight at room temperature and then neutralized with diluted hydrochloric acid. The solution is ultrafiltered (Amicon YM3) and the retentate is freeze-dried.

Yield: 4.16 g (83% of theory)

H$_2$O content (Karl Fischer): 8.2%

Gd determination (AAS): 14.7%

Elementary analysis (relative to anhydrous substance):

Cld: C, 43.08; H, 5.11; Gd, 16.41; N, 11.51; Na, 2.40; S.

Fnd: C, 43.47; H, 5.32; Gd, 16.19; N, 11.23; Na, 2.04; S, 3.07.

The N-methyl-D-glucamine salt is obtained analogously with N-methyl-D-glucamine instead of sodium hydroxide solution:

Cld: C, 43.91; H, 5.93; Gd, 13.89; N, 10.98; S, 2.83.

Fnd: C, 43.73; H, 6.19; Gd, 13.56; N, 11.22; S, 2.60.

Example 3 a) Gadolinium complex of 10-(8-carboxy-2-hydroxy-5-oxo-4-aza-7-oxa-octyl)-1,4,7-tris(carboxymethyl)-1,4,7,10-tetraazacyclododecane 10 g (17.43 mmol) of the title compound of Example 2c is dissolved in 100 ml of water and 20 ml of triethylamine is added. 5.80 g (50 mmol) of diglycolic anhydride is added at 0° C. and stirred for 3 hours at this temperature. It is evaporated to dryness in a vacuum and the residue is chromatographed on silica gel (mobile solvent: methanol/ammonia (25% aqu.) 20:1). The product-containing fractions are evaporated to dryness, taken up with 100 ml of water and the pH of the solution is adjusted to pH 2.46 by adding acid ion exchanger (IR 120 H$^+$). It is filtered off from the exchanger, flushed twice with a little water and evaporated to dryness. The residue is recrystallized from methanol/acetone. After drying in a vacuum (125° C./overnight), 7.57 g (63% of theory) of a colorless crystalline solid is obtained.

Water content: 3.1%

Elementary analysis (relative to anhydrous substance):

Cld: C, 36.57; H, 4.97; Gd, 22.80; N, 10.15.

Fnd: C, 36.43; H, 5.06; Gd, 22.70; N, 10.01.

b) 24-Amide conjugate of the Gd complex of 10-[8-carboxy-2-hydroxy-5-oxo-4-aza-7-oxaoctyl]-1,4,7-tris(carboxymethyl)-1,4,7,10-tetraazacyclododecane with the 24-amine N,N,N',N',N'',N''-hexakis[2-(trilysyl-amino)-ethyl]-trimesic acid triamide 1.20 g (0.2 mmol) of the 24-benzyloxycarbonylamine described in Example 1d is dissolved in glacial acetic acid and mixed with stirring with 33% hydrogen bromide in glacial acetic acid. After 3 hours, the incipient precipitation is completed with diethyl ether, the 24-amine-hydrobromide produced is washed with diethyl ether, dried in a vacuum and used without further purification in the reaction further described below.

Yield: 0.95 g (quantitative)

4.14 g (6 mmol) of the complex acid described in Example 3a, 0.96 g (6 mmol) of 1-hydroxybenzotriazole (HOBt) and 1.92 g (6 mmol) of 2-(1H-benzotriazol-1-yl)-1,1,3,3-tetramethyl-uronium tetrafluoroborate (TBTU; Peboc Limited, UK) are dissolved in DMF and stirred for 15 minutes. This solution is then mixed with 4.13 ml (24 mmol) of N-ethyldiisopropylamine and with 0.95 g (0.2 mmol) of the above-described 24-amine-hydrobromide and stirred overnight at room temperature. After completion of the reaction, 0.23 g (2 mmol) of diglycolic anhydride is added and stirred for one more hour. Then, it is concentrated by evaporation in a vacuum, the residue is taken up in water and purified with an AMICON YM10-ultrafiltration membrane. The retentate is, if necessary, adjusted to pH 7, membrane-filtered and finally freeze-dried.

Yield: 3.62 g (88% of theory)

H$_2$O content (Karl Fischer): 8.1%

Gd determination (AAS): 18.7%

Elementary analysis (relative to anhydrous substance):

Cld: C, 40.24; H, 5.46; Gd, 19.97; N, 12.23.

Fnd: C, 40.07; H, 5.63; Gd, 20.20; N, 12.17.

Example 4 a) N,N,N-Tris[2-(N$^\alpha$,N$^\epsilon$-dibenzyloxycarbonyl-lysylamino)-ethyl]amine 1.46 g (10 mmol) of tris(2-aminoethyl)amine and 21.4 g (40 mmol) of N$^\alpha$,N$^\epsilon$-dibenzyloxycarbonyl-lysine-p-nitrophenylester are dissolved in DMF and stirred overnight at room temperature. After completion of the reaction, it is concentrated by evaporation in a vacuum, the residue is stirred up with diethyl ether, the precipitate is suctioned off and recrystallized from ethyl acetate.

Yield: 12.55 g (94% of theory)

Elementary analysis:

Cld: C, 64.75; H, 6.79; N, 10.49.

Fnd: C, 64.48; H, 6.88; N, 10.26.

b) Completely protected benzyloxycarbonyl-24-polyamine based on N,N,N-tris[2-(N$^\alpha$,N$^\epsilon$-bis{trilysyl}lysylamino)-ethyl]amine 1.33 g (1 mmol) of the hexa-benzyloxycarbonylamine described in Example 4a is dissolved in glacial acetic acid and mixed with stirring with 33% hydrogen bromide in glacial acetic acid. After 60 minutes, the incipient precipitation is completed with diethyl ether, the hexa-amine-hydrobromide produced is washed with ether, dried in a vacuum and used without further purification in the reaction further described below.

Yield: 1.02 g (quantitative)

7.0 g (7.5 mmol) of the N$^\alpha$,N$^\epsilon$-bis(N,N'-dibenzyloxycarbonyllysyl)-lysine (protected "trilysine") described in Example 1c) is activated analogously to Example 1d with TBTU and N-hydroxybenzotriazole and reacted analogously with 1.02 g (1 mmol) of the above-described N,N,N-tris[2-(lysylamino)ethyl]-amine-hexahydrobromide and 5.16 ml (30 mmol) of N-ethyldiisopropylamine and the operation is performed in the same way as described there.

Yield: 4.42 g (73% of theory)

Elementary analysis:

Cld: C, 64.25; H, 6.89; N, 10.64.

Fnd: C, 64.06; H, 7.04; N, 10.69.

c) 24-Gadolinium-DTPA-monoamide based on the 24-amine N,N,N-tris[2-(N$^\alpha$,N$^\epsilon$-bis{trilysyl-lysylamino)-ethyl]amine 1.21 g (0.2 mmol) of the 24-benzyloxycarbonylamine described in Example 4b is dissolved in glacial acetic acid and mixed with stirring with 33% hydrogen bromide in glacial acetic acid. After 3 hours, the incipient precipitation is completed with diethyl ether, the 24-amine-hydrdbromide produced is washed with diethyl ether and dried in a vacuum. The residue is acylated analogously to the instructions given in Example 1e) with 5.8 g (14.4 mmol) of N$^3$-(2,6-dioxomorpholinoethyl)-N$^6$-

(ethoxycarbonylmethyl)-3,6-diazaoctanedioic acid and complexed with 2.61 g (7.2 mmol) of $Gd_2O_3$.

3.30 g (92% of theory) of colorless lyophilizate is obtained.

$H_2O$ content (Karl Fischer): 10.3%

Gd determination (AAS): 20.7%

Elementary analysis (relative to anhydrous substance):

Cld: C, 34.97; H, 4.25; Gd, 23.48; N, 10.28; Na, 3.43.

Fnd: C, 34.69; H, 4.31; Gd, 23.20; N, 10.37; Na, 3.05.

The dysprosium complex is obtained analogously with $DY_2O_3$:

Elementary analysis (relative to anhydrous substance):

Cld: C, 34.70; H, 4.22; Dy, 24.07; N, 10.20; Na, 3.41.

Fnd: C, 34.50; H, 4.42; Dy, 23.81; N, 10.06; Na, 3.02.

Example 5 a) 24-Thiourea conjugate of the Gd complex of 10-[7-(4-isothiocyanatophenyl)-2-hydroxy-5-oxo-7-(carboxymethyl)-4-aza-heptyl]-1,4,7-tris (carboxymethyl)-1,4,7,10-tetraazacyclododecane with the 24-amine condensed from N,N,N-tris[2-(lysylamino)ethyl]amine with $N^\alpha,N^\epsilon$-bis(lysyl) lysine ("trilysine")

1.21 g (0.2 mmol) of the 24-benzyloxycarbonylamine described in Example 1d is dissolved in glacial acetic acid and mixed with stirring with 33% hydrogen bromide in glacial acetic acid. After 3 hours, the incipient precipitation is completed with diethyl ether, the 24-amine-hydrobromide produced is washed with diethyl ether and dried in a vacuum. The residue is then taken up in water and, analogously to the instructions given in Example 2g, it is reacted at pH 9.5 with 6.08 g (7.2 mmol) of the gadolinium complex of 10[7-(4-isothiocyanatophenyl)-2-hydroxy-5-oxo-7-(carboxymethyl)-4-azaheptyl]-1,4,7-tris(carboxymethyl)-1,4,7,10-tetraazacyclododecane and freeze-dried after ultrafiltration.

Yield: 4.31 g (87% of theory)

$H_2O$ content (Karl Fischer): 6.9%

Gd determination (AAS): 15.0%

Elementary analysis (relative to anhydrous substance):

Cld: C, 43.11; H, 5.16; Gd, 16.36; N, 11.54; Na, 2.39; S, 3.34.

Fnd: C, 42.89; H, 5.35; Gd, 16.09; N, 11.67; Na, 2.18; S, 3.23.

Example 6 a) 24-Amide conjugate of the Gd complex of 10-[8-carboxy-2-hydroxy-5-oxo-4-aza-7-oxaoctyl]-1,4,7-tris(carboxymethyl)-1,4,7,10-tetraazacyclododecane with the 24-amine condensed from N,N,N-tris[2-(lysylamino)ethyl] amine with $N^\alpha,N^\epsilon$-bis(lysyl)lysine ("trilysine")

1.21 g (0.2 mmol) of the 24-benzyloxycarbonylamine described in Example 4b is dissolved in glacial acetic acid and mixed with stirring with 33% hydrogen bromide in glacial acetic acid. After 3 hours, the incipient precipitation is completed with diethyl ether, the 24-amine-hydrobromide produced is washed with diethyl ether, dried in a vacuum and used without further purification in the reaction further described below.

Yield: 0.96 g (quantitative)

4.14 g (6 mmol) of the gadolinium complex acid described in Example 3a is activated analogously to the instructions given for Example 3b with TBTU and HOBt in DMF and coupled with the above-described 24-amine-hydrobromide while adding a base and analogously worked up.

Yield: 3.83 g (92% of theory)

$H_2O$ content (Karl Fischer): 8.8%

Gd determination (AAS): 18.5%

Elementary analysis (relative to anhydrous substance):

Cld: C, 40.29; H, 5.52; Gd, 19.90; N, 12.26.

Fnd: C, 39.97; H, 5.71; Gd, 19.55; N, 12.21.

Example 7 a) N,N'-Bis(benzyloxycarbonyl)-3-[carboxymethoxyacetyl]-3-azapentane-1,5-diamine 37.14 g (100 mmol) of the bis (benzyloxycarbonylaminoethyl)-amine described in Example 1a is dissolved in DMF, mixed in an ice bath with 17.4 g (150 mmol) of diglycolic anhydride (Janssen Chimica) and 21 ml (150 mmol) of triethylamine and then stirred overnight at room temperature. The solution is concentrated by evaporation in a vacuum, the residue is taken up in ethyl acetate and shaken out with diluted hydrochloric acid. The organic phase is dried with sodium sulfate and after filtration from drying agent, it is crystallized by adding hexane.

Yield: 41.4 g (85% of theory)

Elementary analysis:

Cld: C, 59.13; H, 6.00; N, 8.62.

Fnd: C, 58.99; H, 5.93; N, 8.70.

b) N,N',N'',N'''-Tetrakis{8-(benzyloxycarbonylamino)-6-[2-(benzyloxycarbonylaminoethyl]-5-oxo-3-oxaoctanoyl}cyclene 345 mg (2 mmol) of 1,4,7,10-tetraazacyclododecane (cyclene; Fluka) is dehydrated azeotropically with toluene. A solution of 4.88 g (10 mmol) of N,N'-bis (benzyloxycarbonyl)-3-[carboxymethoxyacetyl]-3-azapentane-1,5-diamine (Example 7a) in tetrahydrofuran (THF) as well as 2.47 g (10 mmol) of 2-ethoxy-1-ethoxycarbonyl-1,2-dihydroquinoline (EEDQ; Fluka) are added to the cooled solution of cyclene in toluene at room temperature and stirred overnight. After completion of the reaction, the product is precipitated by adding hexane, decanted from solvent and reprecipitated once more from THF/hexane and then from THF/toluene. After drying in a vacuum, 2.78 g (68% of theory) of a pale yellow solid is obtained.

Elementary analysis:

Cld: C, 60.93; H, 6.29; N, 10.93.

Fnd: C, 60.68; H, 6.40; N, 10.97.

c) Completely protected benzyloxycarbonyl-32-polyamine based on the 32-amine condensed from N,N',N'',N'''-tetrakis{8-benzyloxycarbonylamino)-6-[2-(benzyloxycarbonylamino)-ethyl]-5-oxo-3-oxaoctanoyl}cyclene with $N^\alpha,N^\epsilon$-bis(lysyl)-lysine ("trilysine")

2.05 g (1 mmol) of the octa-benzyloxycarbonylamine described in Example 7b is dissolved in glacial acetic acid and mixed with stirring with 33% hydrogen bromide in glacial acetic acid. After 90 minutes, the incipient precipitate is completed with diethyl ether, the octa-amine-hydrobromide produced is washed with ether, dried in a vacuum and used without further purification in the reaction further described below.

Yield: 1.6 g (quantitative)

9.4 g (10 mmol) of the protected "trilysine" described in Example 1c), 1.5 g (10 mmol) of 1-hydroxybenzotriazole and 3.2 g (10 mmol) of 2-(1H-benzotriazol-1-yl)-1,1,3,3-tetramethyluronium tetrafluoroborate (TBTU; Peboc Limited, UK) are dissolved in DMF and stirred for 15 minutes. This solution is then mixed with 5.16 ml (30 mmol) of N-ethyldiisopropylamine and with 1.6 g (1 mmol) of the above-described octa-amine-hydrobromide and stirred overnight at room temperature. After completion of the reaction, it is concentrated by evaporation in a vacuum and the residue is chromatographed on silica gel with dichloromethane/methanol (10:1).

Yield: 6.0 g (72% of theory)
Elementary analysis:
Cld: C, 63.32; H, 6.76; N, 10.74.
Fnd: C, 62.98; H, 6.91; N, 10.43.

d) 32-Gadolinium-DTPA-monoamide based on the unblocked 32-amine of Example 7c 1.67 g (0.2 mmol) of the poly-benzyloxycarbonylamine described in Example 7c is dissolved in glacial acetic acid and mixed with stirring with 33% hydrogen bromide in glacial acetic acid. After 3 hours, the incipient precipitation is completed with diethyl ether, the 32-amine-hydrobromide produced is washed with ether and dried in a vacuum. The residue is then taken up in water and adjusted to pH 9.5 by adding 1 N sodium hydroxide solution. 7.7 g (19.2 mmol) of $N^3$-(2,6-dioxomorpholinoethyl)-$N^6$-(ethoxycarbonylmethyl)-3,6-diazaoctanedioic acid (Example 13a of EP 0331 616) in solid form is added to this solution, and the pH is kept constant at 9.5 by further addition of sodium hydroxide solution. After completion of the addition, it is adjusted with 5 N sodium hydroxide solution to pH>13 for saponification of the DTPA-ethyl ester, and it is stirred overnight at room temperature. Then, it is adjusted to pH 5 with concentrated hydrochloric acid, mixed with 3.48 g (9.6 mmol) of $Gd_2O_3$, stirred for 30 minutes at 80° C., adjusted to pH 7 after cooling and desalinated with a YM3 AMICON-ultrafiltration membrane. The retentate is finally membrane-filtered and freeze-dried.

Yield: 4.27 g (91% of theory)
$H^2O$ content (Karl Fischer): 7.5%
Gd determination (AAS): 22.6%
Elementary analysis (relative to anhydrous substance):
Cld: C, 34.98; H, 4.24; Gd, 23.19; N, 10.33; Na, 3.39.
Fnd: C, 34.67; H, 4.15; Gd, 22.86; N, 10.25; Na, 3.14.

The europium complex is obtained analogously with $Eu_2O_3$:
Elementary analysis (relative to anhydrous substance):
Cld: C, 35.25; H, 4.27; Eu, 22.58; N, 10.41; Na, 3.42.
Fnd: C, 35.08; H, 4.17; Eu, 22.16; N, 10.53; Na, 3.22.

Example 8 a) 32-Thiourea conjugate of the Gd complex of 10-[7-(4-isothiocyanatophenyl)-2-hydroxy-5-oxo-7-(carboxymethyl)-4-aza-heptyl]-1,4,7-tris(carboxymethyl)-1,4,7,10-tetraazacyclododecane with the unblocked 32-amine of Example 7c 1.67 g (0.2 mmol) of the 32-benzyloxycarbonylamine described in Example 7c is dissolved in glacial acetic acid and mixed with stirring with 33% hydrogen bromide in glacial acetic acid. After 3 hours, the incipient precipitation is completed with ether, the 32-amine-hydrobromide produced is washed with diethyl ether and dried in a vacuum. The residue is then taken up in water and adjusted to pH 9.5 by adding 1 N sodium hydroxide solution. 8.1 g (9.6 mmol) of the isothiocyanate described in Example 2f in solid form is added in portions to this solution, and the pH is kept constant at 9.5 by further addition of sodium hydroxide solution. After completion of the addition, it is stirred overnight at room temperature and then neutralized with diluted hydrochloric acid. The solution is ultrafiltered (Amicon YM3) and the retentate is freeze-dried.

Yield: 5.8 g (85% of theory)
$H_2O$ content (Karl Fischer): 9.1%
Gd determination (AAS): 15.2%
Elementary analysis (relative to anhydrous substance):
Cld: C, 43.05; H, 5.15; Gd, 16.22; N, 11.56; Na, 2.37; S, 3.31.
Fnd: C, 42.84; H, 5.36; Gd, 16.00; N, 11.84; Na, 2.10; S, 2.97.

Example 9 a) 1,11-Bis(benzyloxycarbonylamino)-3,9-bis[2-(benzyloxycarbonylamino)ethyl]-4,8-dioxo-6-(4-nitrophenyl)-3,9-diazaundecane 6.33 g (25 mmol) of 3-(4-nitrophenyl)-glutaric acid (J. Org. Chem. 26, 3856 (1961)), 6.33 g (55 mmol) of N-hydroxysuccinimide and 20.43 g (55 mmol) of the bis(benzyloxycarbonyl-aminoethyl)amine described in Example 1a are dissolved in DMF and, after adding 11.35 g (55 mmol) of dicyclohexylcarbodiimide, it is stirred for 3 days at room temperature. Then, it is filtered off from precipitated cyclohexylurea, the filtrate is evaporated to dryness in a vacuum and chromatographically purified on silica gel with ethyl acetate as mobile solvent.

Yield: 17.3 g (72% of theory)
Elementary analysis:
Cld: C, 63.81; H, 5.98; N, 10.21.
Fnd: C, 63.94; H, 5.77; N, 10.26.

b) 1,11-Bis(benzyloxycarbonylamino)-3,9-bis-[2-(benzyloxycarbonylamino)ethyl]-4,8-dioxo-6-(4-aminophenyl)-3,9-diazaundecane 15.57 g (56 mmol) of $FeSO_4 \times 7\ H_2O$ is dissolved in water and combined with 7.68 g (8 mmol) of the nitro compound, described in Example 9a, in the same volume of ethanol and heated to boiling. 24 ml of concentrated ammonia is slowly instilled at this temperature, and a black precipitate forms. The suspension is allowed to cool off slowly with stirring, then it is filtered, the precipitate is rewashed with ethyl acetate and the combined filtrates are evaporated to dryness in a vacuum. The residue is chromatographed on silica gel with ethyl acetate/ethanol (98:2).

Yield: 4.84 g (65% of theory)
Elementary analysis:
Cld: C, 65.86; H, 6.39; N, 10.54.
Fnd: C, 65.68; H, 6.31; N, 10.62.

c) N,N',N",N'"-Cyclene-tetra-ureido conjugate of 1,4,7,10-tetraazacyclododecane with 1,11-bis(benzyloxycarbonylamino)-3,9-bis[2-(benzyloxycarbonylamino)ethyl]-4,8-dioxo-6-(4-isocyanatophenyl)-3,9-diazaundecane 4.65 g (5 mmol) of the phenylamine described in Example 9b is dissolved in toluene, evaporated to dryness twice for dehydration and again taken up with fresh toluene in each case. The solution of amine in toluene, dried in this way, is mixed at 10° C. with 0.54 g (1.8 mmol) of triphosgene, stirred for one hour at 10° C. and overnight at room temperature. 0.17 g (1 mmol) of anhydrous 1,4,7,10-tetraazacyclododecane (cyclene) (Aldrich) in toluene/pyridine (10:1) is added to this suspension and stirred overnight at room temperature. Then, it is evaporated to dryness in a vacuum and the residue is chromatographed on silica gel in ethyl acetate.

Yield: 3.55 g (89% of theory)
Elementary analysis:
Cld: C, 64.98; H, 6.16; N, 11.23.
Fnd: C, 64.70; H, 6.29; N, 11.04.

d) N,N-Bis[2-(benzyloxycarbonylamino)-,ethyl]-glycine-tert-butyl ester 18.6 g (50 mmol) of the bis[2-(benzyloxycarbonylamino)-ethyl]-amine in tetrahydrofuran/water (25:1) described in Example 1a is mixed with 4.2 g (30 mmol) of potassium carbonate. 11.7 g (60 mmol) of tert-butyl-bromoacetate is instilled at room temperature in this suspension and then stirred overnight at this temperature. It is filtered off from the undissolved, the filtrate is evaporated to dryness and chromatographed on silica gel (diethyl ether/diisopropyl ether 1:1).

Yield: 20.4 g (84% of theory)
Elementary analysis:
Cld: C, 64.31; H, 7.26; N, 8.65.
Fnd: C, 64.35; H, 7.00; N, 8.58.

e) N,N-Bis[2-(benzyloxycarbonylamino)-(ethyl]-glycine 19.4 g (40 mmol) of the t-butyl ester described in Example 9d is mixed with 150 ml of trifluoroacetic acid and stirred for 20 minutes at room temperature. Then, the product is precipitated by adding diethyl ether and absorptively precipitated once more each with ether and finally with water. The precipitate is filtered off and dried.

Yield: 13.4 g (78% of theory)
Elementary analysis:
Cld: C, 61.52; H, 6.34; N, 9.79.
Fnd: C, 61.64; H, 6.20; N, 9.94.

f) Completely protected benzyloxycarbonyl-32-polyamine from the N,N',N",N'"-cyclene-tetra-ureido conjugate of Example 9c condensed with N,N-bis[2-(benzyloxycarbonylamino)-ethyl]-glycine 3.99 g (1 mmol) of the hexadeca-benzyloxycarbonylamine described in Example 9c is dissolved in glacial acetic acid and mixed with stirring with 33% hydrogen bromide in glacial acetic acid. After 90 minutes, the incipient precipitation is completed with diethyl ether, the hexadeca-amine-hydrobromide produced is washed with ether, dried in a vacuum and used without further purification in the reaction further described below.

Yield: 3.2 g (quantitative)

8.6 g (20 mmol) of the N,N-bis[2-(benzyloxycarbonylamino)-ethyl]-glycine described in Example 9e, 3.2 g (20 mmol) of 1-hydroxybenzotriazole and 6.4 g (20 mmol) of 2-(1H-benzotriazol-1-yl)-1,1,3,3-tetramethyluronium tetrafluoroborate (TBTU; Peboc Limited, UK) are dissolved in DMF and stirred for 15 minutes. This solution is then mixed with 13.76 ml (80 mmol) of N-ethyldiisopropylamine and with 3.2 g (1 mmol) of the above-described hexadeca-amine-hydrobromide and stirred overnight at room temperature. After completion of the reaction, it is concentrated by evaporation in a vacuum, and the residue is chromatographed with dichloromethane/methanol (9:1) on silica gel.

Yield: 7.3 g (87% of theory)
Elementary analysis:
Cld: C, 62.69; H, 6.55; N, 13.29.
Fnd: C, 62.37; H, 6.72; N, 13.38.

g) 32-Gadolinium-DTPA-monoamide based on the unblocked 32-amine of Example 9f 1.69 g (0.2 mmol) of the poly-benzyloxycarbonylamine described in Example 9f is dissolved in glacial acetic acid and mixed with stirring with 33% hydrogen bromide in glacial acetic acid. After 3 hours, the incipient precipitation is completed with diethyl ether, the 32-amine-hydrobromide produced is washed with ether and dried in a vacuum. The residue is then taken up in water and adjusted to pH 9.5 by adding 1 N sodium hydroxide solution. 7.3 g (19.2 mmol) of $N^3$-(2,6-dioxomorpholinoethyl)-$N^6$-(ethoxycarbonylmethyl)-3,6-diazaoctanedioic acid (Example 13a of EP 0331 616) in solid form is added to this solution, and the pH is kept constant at 9.5 by further addition of sodium hydroxide solution. After completion of the addition, it is adjusted to pH>13 with 5 N sodium hydroxide solution for saponification of the DTPA-ethyl ester, and it is stirred overnight at room temperature. Then, it is adjusted to pH 5 with concentrated hydrochloric acid, mixed with 3.48 g (9.6 mmol) of $Gd_2O_3$, stirred for 30 minutes at 80° C., adjusted to pH 7 after cooling and desalinated with a YM3 AMICON-ultrafiltration membrane. The retentate is finally membrane-filtered and freeze-dried.

Yield: 4.29 g (91% of theory)
$H_2O$ content (Karl Fischer): 9.1%
Gd determination (AAS): 22.7%
Elementary analysis (relative to anhydrous substance):
Cld: C, 35.41; H, 4.31; Gd, 23.48; N, 11.50; Na, 1.72.
Fnd: C, 35.39; H, 4.20; Gd, 23.22; N, 11.69; Na, 1.59.

Example 10 a) 32-Thiourea conjugate of the Gd complex of 10-[7-(4-isothiocyanatophenyl)-2-hydroxy-5-oxo-7(carboxymethyl)-4-aza-heptyl]-1,4,7-tris(carboxymethyl)-1,4,7,10-tetraazacyclododecane with the unblocked 32-amine of Example 9f 1.69 g (0.2 mmol) of the 32-benzyloxycarbonylamine described in Example 9f is dissolved in glacial acetic acid and mixed with stirring with 33% hydrogen bromide in glacial acetic acid. After 3 hours, the incipient precipitation is completed with ether, the 32-amine-hydrobromide produced is washed with diethyl ether and dried in a vacuum. The residue is then taken up in water and adjusted to pH 9.5 by adding 1 N sodium hydroxide solution. 8.1 g (9.6 mmol) of the isothiocyanate, described in Example 2f, in solid form is added in portions to this solution, and the pH is kept constant at 9.5 by further addition of sodium hydroxide solution. After completion of the addition, it is stirred overnight at room temperature and then neutralized with diluted hydrochloric acid. The solution is ultrafiltered (Amicon YM3) and the retentate is freeze-dried.

Yield: 5.7 g (85% of theory)

H2O content (Karl Fischer): 8.7%

Gd determination (AAS): 15.3%

Elementary analysis (relative to anhydrous substance):

Cld: C, 43.47; H, 5.10; Gd, 16.38; N, 12.40; Na, 1.20; S, 3.34.

Fnd: C, 43.25; H, 5.27; Gd, 16.11; N, 12.46; Na, 1.05; S, 3.62.

Example 11 a) N,N',N'',N'''-Tetrakis{N,N-bis[2-(benzyloxycarbonylamino)-ethyl]-glycyl}-cyclene 345 mg (2 mmol) of 1,4,7,10-tetraazacyclododecane (cyclene; Fluka) is azeotropically dehydrated with toluene. A solution of 4.29 g (10 mmol) of the N,N-bis[2-(benzyloxycarbonylamino)-ethyl]-glycine in tetrahydrofuran (THF) described in Example 9e as well as 2.47 g (10 mmol) of 2-ethoxy-1-ethoxycarbonyl-1,2-dihydroquinoline (EEDQ; Fluka) are added to the cooled solution of cyclene in toluene at room temperature and stirred overnight. The solution is evaporated to dryness in a vacuum and chromatographed in ethyl acetate/methanol (10:1) on silica gel.

Yield: 2.69 g (74% of theory)

Elementary analysis:

Cld: C, 63.42; H, 6.65; N, 12.33.

Fnd: C, 63.17; H, 6.80; N, 12.28.

b) Completely protected benzyloxycarbonyl-32-polyamine based on N,N',N'',N'''-tetrakis{N,N-bis[2-(trilysylamino)-ethyl]-glycyl}-cyclene 1.82 g (1 mmol) of the octa-benzyloxycarbonylamine described in Example 11a is dissolved in glacial acetic acid and mixed with stirring with 33% hydrogen bromide in glacial acetic acid. After 90 minutes, the incipient precipitation is completed with diethyl ether, the octa-amine-hydrobromide produced is washed with ether, dried in a vacuum and reacted without further purification in the reaction further described below.

Yield: 1.39 g (quantitative)

9.4 g (10 mmol) of the protected "trilysine" described in Example 1c, 1.5 g (10 mmol) of 1-hydroxybenzotriazole and 3.2 g (10 mmol) of 2-(1H-benzotriazol-1-yl)-1,1,3,3-tetramethyluronium tetrafluoroborate (TBTU; Peboc Limited, UK) are dissolved in DMF and stirred for 15 minutes. This solution is then mixed with 5.16 ml (30 mmol) of N-ethyldiisopropylamine and with 1.39 g (1 mmol) of the above-described octa-amine-hydrobromide and stirred overnight at room temperature. After completion of the reaction, it is concentrated by evaporation in a vacuum and the residue is chromatographed with dichloromethane/methanol (10:1) on silica gel.

Yield: 6.0 g (74% of theory)

Elementary analysis:

Cld: C, 63.95; H, 6.86; N, 11.05.

Fnd: C, 64.23; H, 7.01; N, 10.92.

c) 32-Gadolinium-DTPA-monoamide based on the unblocked 32-amine of Example 11b 1.62 g (0.2 mmol) of the poly-benzyloxycarbonylamine described in Example 11b is dissolved in glacial acetic acid and mixed with stirring with 33% hydrogen bromide in glacial acetic acid. After 3 hours, the incipient precipitation is completed with diethyl ether, the 32-amine-hydrobromide produced is washed with ether and dried in a vacuum. The residue is then taken up in water and adjusted to pH 9.5 by adding 1 N sodium hydroxide solution. 7.7 g (19.2 mmol) of $N^3$-(2,6-dioxomorpholinoethyl)-$N^6$-(ethoxycarbonylmethyl)-3,6-diazaoctanedioic acid (Example 13a of EP 0331 616) in solid form is added to this solution, and the pH is kept constant at 9.5 by further addition of sodium hydroxide solution. After completion of the addition, it is adjusted to pH>13 with 5 N sodium hydroxide solution for saponification of the DTPA-ethyl ester, and it is stirred overnight at room temperature. Then, it is adjusted to pH 5 with concentrated hydrochloric acid, mixed with 3.48 g (9.6 mmol) of $Gd_2O_3$, stirred for 30 minutes at: 80° C., adjusted to pH 7 after the cooling and desalinated with a YM3 AMICON-ultrafiltration membrane. The retentate is finally membrane-filtered and freeze-dried.

Yield: 4.0 g (89% of theory)

$H_2O$ content (Karl Fischer): 4.9%

Gd determination (AAS): 22.1%

Elementary analysis (relative to anhydrous substance):

Cld: C, 35.05; H, 4.28; Gd, 23.58; N, 10.48; Na, 3.01.

Fnd: C, 34.82; H, 4.40; Gd, 23.19; N, 10.46; Na, 2.79.

Example 12 a) 32-Thiourea conjugate of the Gd complex of 10-[7-(4-isothiocyanatophenyl)-2-hydroxy-5-oxo-7-(carboxymethyl)-4-aza-heptyl]-1,4,7-tris(carboxymethyl)-1,4,7,10-tetraazacyclododecane with the unblocked 32-amine of Example 11b 1.62 g (0.2 mmol) of the 32-benzyloxycarbonylamine described in Example 11b is dissolved in glacial acetic acid and mixed with stirring with 33% hydrogen bromide in glacial acetic acid. After 3 hours, the incipient precipitation is completed with ether, the 32-amine-hydrobromide produced is washed with diethyl ether and dried in a vacuum. The residue is then taken up in water and adjusted to pH 9.5 by adding 1 N sodium hydroxide solution. 8.1 g (9.6 mmol) of the isothiocyanate described in Example 2f in solid form is added in portions to this solution, and the pH is kept constant at 9.5 by further addition of sodium hydroxide solution. After completion of the addition, it is stirred overnight at room temperature and then neutralized with diluted hydrochloric acid. The solution is ultrafiltered (Amicon YM3) and the retentate is freeze-dried.

Yield: 5.6 g (88% of theory)

$H_2O$ content (Karl Fischer): 3.5%

Gd determination (AAS): 15.9%

Elementary analysis (relative to anhydrous substance):

Cld: C, 43.18; H, 5.19; Gd, 16.39; N, 11.68; Na, 2.10; S, 3.34.

Fnd: C, 42.95; H, 5.33; Gd, 16.02; N, 11.90; Na, 1.71; S, 2.98.

Example 13 a) N,N,N',N',N'',N''-Hexakis{2-[N,N-bis(2-benzyloxycarbonylamino-ethyl)amino]ethyl}-trimesic acid triamide 1.27 g (1 mmol) of the hexa-benzyloxycarbonylamine described in Example 1b is dissolved in glacial acetic acid and mixed with stirring with 33% of hydrogen bromide in glacial acetic acid. After 60 minutes, the incipient precipitation is completed with diethyl ether, the hexa-amine-hydrobromide produced is washed with ether, dried in a vacuum and used without further purification in the reaction further described below.

Yield: 0.95 g (quantitative)

0.95 g (1 mmol) of the thus produced hydrobromide is suspended in 50 ml of acetonitrile and 3 ml of triethylamine is added. Then, 3.54 g (20 mmol) of N-benzyloxycarbonylaziridine (produced according to J. Chem. Soc. Perkin Trans. 1, 21–26, 1993) is added and refluxed for 5 days under nitrogen. It is evaporated to dryness, taken up with 100 ml of methylene chloride and washed twice with 100 ml each of 5% potassium carbonate solution. The methylene chloride phase is dried on magnesium sulfate and concentrated by evaporation. The residue is chromatographed on silica gel (mobile solvent: methylene chloride/methanol/triethylamine 20:1:0.1).

Yield: 2.31 g (89% of theory) of a pale yellow viscous oil

Elementary analysis:

Cld: C, 65.34; H, 6.65; N, 11.35.

Fnd: C, 65.12; H, 6.80; N, 11.19.

b) N,N,N',N',N",N"-Hexakis{2-[N,N-bis(2-aminoethyl)amino]ethyl}-trimesic acid triamide 2.2 g (0.85 mmol) of the title compound of Example 13a is dissolved in 100 ml of methanol and 3 g of Pearlman's catalyst (palladium hydroxide on activated carbon; Fluka) is added. It is hydrogenated for 10 hours at 5 bars (room temperature). It is filtered off from the catalyst and the filtrate is evaporated to dryness.

Yield: 825 mg (99% of theory)

Elementary analysis:

Cld: C, 55.02; H, 10.16; N, 26.94.

Fnd: C, 54.87; H, 10.25; N, 29.85.

c) Completely protected benzyloxycarbonyl-24-polyamine based on N,N,N',N',N",N"-hexakis{2-[N,N-bis(2-(N,N-bis-aminoethyl)-amino)ethyl]-aminoethyl}-trimesic acid triamide 800 mg (0.814 mmol) of the title compound of Example 13b is dissolved in 150 ml of acetonitrile and 5.77 g (32.56 mmol) of N-benzyloxycarbonylaziridine (produced according to J. Chem. Soc., Perkin Trans., 1, 21–26, 1993) and refluxed for 5 days (under nitrogen). It is evaporated to dryness in a vacuum and chromatographed on silica gel (mobile solvent: methylene chloride/methanol/triethylamine 20:1:0.1).

Yield: 3.62 g (85% of theory) of a vitreous solid

Elementary analysis:

Cld: C, 65.39; H, 6.99; N, 12.04.

Fnd: C, 65.21; H, 7.10; N, 11.90.

d) Completely protected benzyloxycarbonyl-48-polyamine based on the 24-lysyl derivative of Example 13c 1.05 g (0.2 mmol) of the title compound of Example 13c is dissolved in 30 ml of methanol and 1 g of Pearlman's catalyst (palladium hydroxide on activated carbon) is added. It is hydrogenated for 10 hours at 5 bars (room temperature). It is filtered off from the catalyst, the filtrate is evaporated to dryness and used in the reaction further described above.

Yield: 0.40 g (quantitative).

3.11 g (7.5 mmol) of $N_\alpha,N_\varepsilon$-bis(benzyloxycarbonyl)-lysine (Bachem, Switzerland), 1.2 g (7.5 mmol) of 1-hydroxybenzotriazole and 2.4 g (7.5 mmol) of 2-(1H-benzotriazol-1-yl)-1,1,3,3-tetramethyluronium tetrafluoroborate (TBTU; Peboc Limited, UK) are dissolved in DMF and stirred for 15 minutes. This solution is then mixed with 5.16 ml (30 mmol) of N-ethyldiisopropylamine and with 0.40 g (0.2 mmol) of the above-described 24-polyamine and stirred overnight at room temperature. After completion of the reaction, it is concentrated by evaporation in a vacuum and the residue is chromatographed with ethyl acetate/ethanol/triethylamine (2:1:0.2) on silica gel.

Yield: 1.36 g (59% of theory)

Elementary analysis:

Cld: C, 64.69; H, 6.95; N, 11.30.

Fnd: C, 64.42; H, 7.11; N, 11.19.

e) 48-Gadolinium-DTPA-monoamide based on the unblocked 48-amine of Example 13d 1.15 g (0.1 mmol) of the title compound of Example 13d is dissolved in glacial acetic acid and mixed with stirring with 33% hydrogen bromide in glacial acetic acid. After 3 hours, the incipient precipitation is completed with diethyl ether, the 48-amine-hydrobromide produced is washed with ether and dried in a vacuum.

The residue is then taken up in water and adjusted to pH 9.5 by adding 1 N sodium hydroxide solution. 5.8 g (14.4 mmol) of $N^3$-(2,6-dioxomorpholinoethyl)-$N^6$-(ethoxycarbonylmethyl)-3,6-diazaoctanedioic acid (Example 13a of EP 0 331 616) in solid form is added to this solution, and the pH is kept constant at 9.5 by further addition of sodium hydroxide solution. After completion of the addition, it is adjusted to pH>13 with 5 N sodium hydroxide solution for saponification of the DTPA-ethyl ester, and it is stirred overnight at room temperature. Then, it is adjusted to pH 5 with concentrated hydrochloric acid, mixed with 2.61 g (7.2 mmol) of $Gd_2O_3$, stirred for 30 minutes at 80° C., adjusted to pH 7 after the cooling and desalinated with a YM3 AMICON-ultrafiltration membrane. The retentate is finally membrane-filtered and freeze-dried.

Yield: 3.15 g (92% of theory)

$H_2O$ content (Karl Fischer): 8.9%.

Gd determination (AAS): 21.9%

Elementary analysis (relative to anhydrous substance):

Cld: C, 35.03; H, 4.34; Gd, 24.22; N, 10.65; Na, 2.21.

Fnd: C, 34.84; H, 4.50; Gd, 23.63; N, 10.87; Na, 2.04.

Example 14 a) 48-Thiourea conjugate of the Gd complex of 10-[7-(4-isothiocyanatophenyl)-2-hydroxy-5-oxo-7-(carboxymethyl)-4-aza-heptyl]-1,4,7-tris(carboxymethyl)-1,4,7,10-tetraazacyclododecane with the unblocked 48-amine of Example 13d 1.15 g (0.1 mmol) of the title compound of Example 13d is dissolved in glacial acetic acid and mixed with stirring with 33% hydrogen bromide in glacial acetic acid. After 3 hours, the incipient precipitation is completed with diethyl ether, the 48-amine-hydrobromide produced is washed with ether and dried in a vacuum.

The residue is then taken up in water and adjusted to pH 9.5 by adding 1 N sodium hydroxide solution. 6.08 g (7.2 mmol) of the isothiocyanate, described in Example 2f, in solid form is added in portions to this solution, and the pH is kept constant at 9.5 by further addition of sodium hydroxide solution. After completion of the addition, it is stirred overnight at room temperature and then neutralized with diluted hydrochloric acid. The solution is ultrafiltered (Amicon YM3) and the retentate is freeze-dried.

Yield: 3.91 g (82% of theory)
H$_2$O content (Karl Fischer): 4.5%
Gd determination (AAS): 16.6%
Elementary analysis (relative to anhydrous substance):
Cld: C, 43.33; H, 5.24; Gd, 16.71; N, 11.82; Na, 1.53; S, 3.41.
Fnd: C, 43.04; H, 5.54; Gd, 16.19; N, 12.10; Na, 1.26; S, 3.89.

Example 15 a) 1,4,7,10,13,16-Hexakis[2-(benzyloxycarbonylamino)-ethyl]-1,4,7,10,13,16-hexaazacyclooctadecane 1.29 g (5 mmol) of 1,4,7,10,13,16-hexaazacyclooctadecane (hexacyclene: Fluka) is azeotropically dehydrated with toluene. A solution of 10.63 g (60 mmol) of N-benzyloxycarbonylaziridine (J. Chem. Soc., Perkin Trans. 1, 21–26, 1993) in acetonitrile is added to the solution of hexacyclene in toluene cooled to room temperature and it is refluxed for 3 days under nitrogen. It is evaporated to dryness and the residue is chromatographed in ethyl acetate/methanol/triethylamine (8:2:0.5) on silica gel.

Yield: 5.68 g (86% of theory) of pale yellow, viscous oil
Elementary analysis:
Cld: C, 65.43; H, 7.32; N, 12.72.
Fnd: C, 65.20; H, 7.51; N, 12.49.

b) Completely protected benzyloxycarbonyl-24-polyamine based on the 1,4,7,10,13,16-hexakis-[2-(trilysylamino)-ethyl]-hexacyclene 1.32 g (1 mmol) of the hexa-benzyloxycarbonylamine described in Example 15a is dissolved in glacial acetic acid and mixed with stirring with 33% hydrogen bromide in glacial acetic acid. After 60 minutes, the incipient precipitation is completed with diethyl ether, the hexa-amine-hydrobromide produced is washed with ether, dried in a vacuum and used without further purification in the reaction further described below.

Yield: 1.48 g (quantitative)

7.0 g (7.5 mmol) of the protected "trilysine" described in Example 1c, 1.2 g (7.5 mmol) of 1-hydroxybenzotriazole and 2.4 g (7.5 mmol) of 2-(1H-benzotriazol-1-yl)-1,1,3,3-tetramethyluronium tetrafluoroborate (TBTU; Peboc Limited, UK) are dissolved in DMF and stirred for 15 minutes. This solution is then mixed with 5.16 ml (30 mmol) of N-ethyldiisopropylamine and with 1.48 g (1 mmol) of the above-described hexa-amine-hydrobromide and stirred overnight at room temperature. After completion of the reaction, it is concentrated by evaporation in a vacuum and the residue is chromatographed with dichloromethane/methanol (10:1) on silica gel.

Yield: 5.02 g (83% of theory)
Elementary analysis:
Cld: C, 64.40; H, 7.00; N, 11.13.
Fnd: C, 64.16; H, 6.82; N, 10.88.

c) 24-Gadolinium-DTPA-monoamide based on 1,4,7,10,13,16-hexakis[2-(trilysylamino)ethyl]-hexacyclene 1.21 g (0.2 mmol) of the poly-benzyloxycarbonylamine described in Example 15b is dissolved in glacial acetic acid and mixed with stirring with 33% hydrogen bromide in glacial acetic acid. After 3 hours, the incipient precipitation is completed with diethyl ether, the 24-amine-hydrobromide produced is washed with ether and dried in a vacuum. The residue is then taken up in water and adjusted to pH 9.5 by adding 1 N sodium hydroxide solution. 5.8 g (14.4 mmol) of N$^3$-(2,6-dioxomorpholinoethyl)-N6-(ethoxycarbonylmethyl)-3,6-diazaoctanedioic acid (Example 13a of EP 0331 616) in solid form is added to this solution, and the pH is kept constant at 9.5 by further addition of sodium hydroxide solution. After completion of the addition, it is adjusted to pH>13 with 5 N sodium hydroxide solution for saponification of the DTPA-ethyl ester, and it is stirred overnight at room temperature. Then, it is adjusted to pH 5 with concentrated hydrochloric acid, mixed with 2.61 g (7.2 mmol) of Gd$_2$O$_3$, stirred for 30 minutes at 80° C., adjusted to pH 7 after the cooling and desalinated with a YM3 AMICON-ultrafiltration membrane. The retentate is finally membrane-filtered and freeze-dried.

Yield: 3.17 g (92.5% of theory)
H$_2$O content (Karl Fischer): 8.7%
Gd determination (AAS): 21.9%
Elementary analysis (relative to anhydrous substance):
Cld: C, 35.94; H, 4.45; Gd, 24.13; N, 10.75; Na, 2.65.
Fnd: C, 36.19; H, 4.26; Gd, 24.39; N, 10.48; Na, 2.29.

Example 16 a) 24-Thiourea conjugate of the Gd complex of 10-[7-(4-isothiocyanatophenyl)-2-hydroxy-5-oxo-7-(carboxymethyl)-4-aza-heptyl]-1,4,7-tris(carboxymethyl)-1,4,7,10-tetraazacyclododecane with the 24-amine 1,4,7,10,13,16-hexakis[2-trilysylamino)-ethyl]-hexacyclene 1.21 g (0.2 mmol) of the 16-benzyloxycarbonylamine described in Example 15b is dissolved in glacial acetic acid and mixed with stirring with 33% hydrogen bromide in glacial acetic acid. After 3 hours, the incipient precipitation is completed with diethyl ether, the 24-amine-hydrobromide produced is washed with ether and dried in a vacuum.

The residue is then taken up in water and adjusted to pH 9.5 by adding 1 N sodium hydroxide solution. 6.08 g (7.2 mmol) of the isothiocyanate, described in Example 2f, in solid form is added in portions to this solution, and the pH is kept constant at 9.5 by further addition of sodium hydroxide solution. After completion of the addition, it is stirred overnight at room temperature and then neutralized with diluted hydrochloric acid. The solution is ultrafiltered (Amicon YM3) and the retentate is freeze-dried.

Yield: 4.33 g (89% of theory)
H$_2$O content (Karl Fischer): 7.0%
Gd determination (AAS): 15.7%
Elementary analysis (relative to anhydrous substance):
Cld: C, 43.94; H, 5.32; Gd, 16.67; N, 11.88; Na, 1.83; S, 3.40.
Fnd: C, 43.70; H, 5.16; Gd, 16.21; N, 12.05; Na, 1.49; S, 3.78.

Example 17 a) Gadolinium complex of 10-[6-(4-nitrophenyl)-2-hydroxy-5-oxo-4-azahexyl]-1,4,7-tris(carboxymethyl)-1,4,7,10-tetraazacyclododecane 20 g (34.86 mmol) of the title compound of Example 2c is dissolved in 200 ml of water and the pH is brought to 10 with 2n sodium hydroxide solution. In this connection, a solution of 13.97 g (70 mmol) of 4-nitrophenylacetic acid chloride in 50 ml of dioxane is instilled at 0° C. and the pH is kept at 10 by adding 2 N sodium hydroxide solution. It is allowed to stir for 2 more hours at room temperature. Then, it is adjusted to pH 7 with 10% hydrochloric acid and the aqueous solution is extracted twice with 200 ml of ethyl acetate. The aqueous phase is evaporated to dryness and the residue is purified by chromatography (RP-18/LiChroPrep®/mobile solvent: gradient of tetrahydrofuran/methanol/water). After concentration by evaporation of the main fractions, 22.5 g (81% of theory) of a cream-colored solid is obtained.

Water content: 7.5%
Analysis (relative to anhydrous substance):
Cld: C, 50.75; H, 4.79; Gd, 21.34; N, 11.41.
Fnd: C, 40.61; H, 4.89; Gd, 21.15; N, 11.30.

b) Gadolinium complex of 10-[6-(4-aminophenyl)-2-hydroxy-5-oxa-4-aza-hexyl]-1,4,7-tris(carboxymethyl)-1,4,7,10-tetraazacyclododecane 21 g (28.5 mmol) of the title compound of Example 17a is dissolved in 200 ml of methanol and 4 g of palladium catalyst (10% Pd on C) is added. It is hydrogenated for 6 hours at room temperature. The catalyst is filtered off and the filtrate is evaporated to dryness.

Yield: 20.56 g (99% of theory) of yellowish, vitreous solid
Water content: 13.1%
Analysis (relative to anhydrous substance):
Cld: C, 42.48; H, 5.28; Gd, 22.25; N, 11.89.
Fnd: C, 42.31; H, 5.41; Gd, 22.07; N, 11.67.

c) Gadolinium complex of 10-[6-(4-isothiocyanatophenyl)-2-hydroxy-5-oxo-4-aza-hexyl]-1,4,7-tris(carboxymethyl)-1,4,7,10-tetraazacyclododecane 20 g (28.29 mmol) of the title compound of Example 17b is dissolved in 100 ml of water and 9.76 g (84.9 mmol) of thiophosgene in 50 ml of chloroform is added. It is stirred for 1 hour at 50°0 C. It is cooled off to room temperature, the organic phase is separated and the aqueous phase is shaken out twice with 100 ml of chloroform. The aqueous phase is evaporated to dryness, and the residue is absorptively precipitated in 200 ml of sopropanol at room temperature. The solid is filtered off, the ether is rewashed and dried overnight in a vacuum at 40° C.

Yield: 21.7 g (99% of theory) of a light cream-colored solid
Water content: 3.4%
Analysis (relative to anhydrous substance):
Cld: C, 41.70; H, 4.71; Gd, 21.00; N, 11.22; S, 4.28.
Fnd: C, 41.55; H, 4.85; Gd, 20.85; N, 11.11; S, 4.20.

d) N,N,N',N'-Tetrakis[2-(benzyloxycarbonylamino)-ethyl]-5-nitro-isophthalic acid-diamide 14.86 g (40 mmol) of the bis[2-(benzyloxycarbonylamino)-ethyl]-amine described in Example 1a and 20.24 g (200 mmol) of triethylamine are dissolved in dimethylformamide and mixed with 4.96 g (20 mmol) of 5-nitro-isophthalic acid dichloride (J. Chem. Soc. 1957, 1172–1175) and stirred overnight at room temperature. The solution is concentrated by evaporation in a vacuum and the residue is chromatographed with ethyl acetate on silica gel.

Yield: 11.5 g (62.6%) of a viscous oil
Elementary analysis:
Cld: C, 62.80; H, 5.60; N, 10.68.
Fnd: C, 62.62; H, 5.77; N, 10.41.

e) N,N,N',N'-Tetrakis[2-(benzyloxycarbonylamino)-ethyl]-5-amino-isophthalic acid-diamide 9.18 g (10 mmol) of the nitro compound, described in the example above, in 200 ml of ethanol is added to a solution of 27.8 g (100 mmol) of $FeSO_4 \times 7\ H_2O$ in 200 ml of water and heated to boiling. After adding 50 ml of concentrated ammonia, it is stirred with refluxing for another 90 minutes. The suspension is allowed to cool off, then the ethanol is concentrated by evaporation in a vacuum and the aqueous phase is shaken out with ethyl acetate. After drying on sodium sulfate, 8.61 g (97% of theory) of an almost colorless viscous oil is obtained.

Elementary analysis:
Cld: C, 64.93; H, 6.02; N, 11.04.
Fnd: C, 65.10; H, 5.96; N, 10.89.

f) N,N,N',N'-Tetrakis[2-(benzyloxycarbonylamino)-ethyl]-5-(carboxymethoxyacetylamino)-isophthalic acid-diamide 4.44 g (5 mmol) of the amino compound, described in the example above, in dimethylformamide is mixed in an ice bath with 5.05 g (50 mmol) of triethylamine and 2.9 g (25 mmol) of diglycolic anhydride (Fluka) and stirred for 2 hours at 0° C. It is evaporated to dryness in a vacuum, the residue is dispersed between ethyl acetate and 1 M citric acid, washed neutral with water and the organic phase is dried.

Yield: 4.62 g (92% of theory) of a viscous oil
Elementary analysis:
Cld: C, 62.20; H, 5.72; N, 9.77.
Fnd: C, 62.03; H, 5.60; N, 9.89.

g) Completely protected benzyloxycarbonyl-hexadeca-amine based on N,N',N'',N'''-tetrakis-(trilysylaminomethyl]methane 3.0 g (22.69 mmol) of tetrakis(aminomethyl)methane (produced according to U.S. Pat. No. 4,485,237 A, 1984), 127.85 g (136.15 mmol) of the title compound of Example 1c and 15.67 g (136.15 mmol) of N-hydroxysuccinimide are dissolved in 300 ml of dimethylformamide. At 0° C., 28.09 g (136.15 mmol) of dicyclohexylcarbodiimide is added and stirred for 1 hour at 0° C., then for 2 days at room temperature. 300 ml of ethyl acetate is added, filtered off from precipitated urea and the filtrate is evaporated to dryness in a vacuum. The residue is chromatographed on silica gel (mobile solvent: methylene chloride/isopropanol 20:1).

Yield: 58.02 g (67% of theory) of a colorless viscous oil
Elementary analysis:
Cld: C, 64.52; H, 6.76; N, 10.28.
Fnd: C, 64.41; H, 6.91; N, 10.05.

h) Completely protected benzyloxycarbonyl-64-amine from the 16-amine N,N',N'',N'''-tetrakis-(trilysylaminomethyl)-methane condensed with tetraamine-monocarboxylic acid 17f 1.91 g (0.5 mmol) of the 16-benzyloxycarbonylamine described in Example 17g is dissolved in glacial acetic acid and mixed with stirring with 33% hydrogen bromide in glacial acetic acid. After 3 hours, the incipient precipitation is completed with diethyl ether, the 16-amine-hydrobromide produced is washed with ether, dried in a vacuum and used without further purification in the subsequent reaction.

Yield: 1.48 g (quantitative)

12.05 g (12 mmol) of the tetraamine-monocarboxylic acid described in Example 17f, 1.92 g (12 mmol) of 1-hydroxybenzotriazole (HOBt) and 3.84 g (12 mmol) of 2-(1H-benzotriazol-1-yl)-1,1,3,3-tetramethyl-uronium tetrafluoroborate (TBTU; Peboc Limited, UK) are dissolved in DMF and stirred for 15 minutes. This solution is then mixed with 6.20 ml (36 mmol) of N-ethyldiisopropylamine and with 1.48 g (0.5 mmol) of the above-described 16-amine-hydrobromide, and it is stirred overnight at room temperature. After completion of the reaction, it is concentrated by evaporation in a vacuum and the residue is chromatographed with ethyl acetate/ethanol (2:1) on silica gel.

Yield: 4.54 g (52% of theory) of a light yellow oil

Elementary analysis:

Cld: C, 62.58; H, 6.01; N, 11.24.

Fnd: C, 62.39; H, 6.22; N, 11.00.

i) 64-Thiourea conjugate of the gadolinium complex of 10-[6-(4-isothiocyanatophenyl)-2-hydroxy-5-oxo-4-aza-hexyl]-1,4,7-tris(carboxymethyl)-1,4,7,10-tetraazacyclododecane with the unblocked 64-polyamine of Example 17h 1.74 g (0.1 mmol) of the 64-benzyloxycarbonylamine described in Example 17h is dissolved in glacial acetic acid and mixed with stirring with 33% hydrogen bromide in glacial acetic acid. After 3 hours, the incipient precipitation is completed with diethyl ether, the 64-amine-hydrobromide produced is washed with ether and dried in a vacuum. The residue is then taken up in water and adjusted to pH 9.5 by adding 1 N sodium hydroxide solution. 7.20 g (9.6 mmol) of the isothiocyanate, described in Example 17c, in solid form is added in portions to this solution, and the pH is kept constant at 9.5 by further addition of sodium hydroxide solution. After completion of the addition, it is stirred overnight at room temperature and then neutralized with diluted hydrochloric acid. The solution is ultrafiltered (Amicon YM3) and the retentate is freeze-dried.

Yield: 5.31 g (86% of theory)

$H_2O$ content (Karl Fischer): 8.0%

Gd determination (AAS): 16.2%

Elementary analysis (relative to anhydrous substance):

Cld: C, 43.59; H, 5.14; Gd, 17.72; N, 12.92; S, 3.61.

Fnd: C, 43.36; H, 5.41; Gd, 17.18; N, 13.20; S, 3.04.

Example 18 a) 2-Nitro-5-hydroxy-benzoic acid benzyl ester 40 g (218.4 mmol) of 2-hydroxy-5-nitro-benzoic acid, 236.17 g (2.184 mol) of benzyl alcohol and 1 g of p-toluenesulfonic acid in 1000 ml of toluene are heated for 2 days in a water separator. It is evaporated to dryness and the residue is chromatographed on silica gel (mobile solvent: methylene chloride/hexane/acetone=15:5:1).

Yield: 50.72 g (85% of theory) of a yellow solid

Analysis:

Cld: C, 61.54; H, 4.06; N, 5.13.

Fnd: C, 61.31; H, 4.17; N, 5.05.

b) 2-[4-Nitro-2-(benzyloxycarbonyl)-phenoxy]-acetic acid-tert-butyl ester 42.8 g (220 mmol) of bromoacetic acid-tert-butyl ester is added to 50 g (183 mmol) of the title compound of Example 18a, 20.5 g (366 mmol) of finely powdered potassium hydroxide and 500 mg of tetrabutylammonium hydrogen sulfate in 500 ml of toluene at 0° C., and it is stirred for 3 hours at 0° C. It is mixed with 500 ml of ice water, stirred vigorously for 2 minutes and the organic phase is separated. The organic phase is dried on magnesium sulfate and concentrated by evaporation in a vacuum. The residue is chromatographed on silica gel (mobile solvent: methylene chloride/hexane/acetone=15:10:1).

Yield: 47.5 g (67% of theory) of a yellow viscous oil

Analysis:

Cld: C, 62.01; H, 5.46; N, 3.62.

Fnd: C, 62.13; H, 5.55; N, 3.50.

c) 2-[4-Nitro-2-(benzyloxycarbonyl)-phenoxy]-acetic acid 40 g (103.26 mmol) of the title compound of Example 18b is dissolved in 300 ml of methylene chloride. 100 ml of trifluoroacetic acid is instilled at 0° C. and allowed to come to room temperature. After 4 hours, it is evaporated to dryness. The residue is recrystallized from a little ether/hexane.

Yield: 32.5 g (95% of theory) of a light yellowish solid

Analysis:

Cld: C, 58.01; H, 3.96; N, 4.23.

Fnd: C, 58.17; H, 3.81; N, 4.18.

d) N-Hydroxysuccinimide ester of 2-[4-nitro-2-(benzyloxycarbonyl)-phenoxy]-acetic acid 10 g (30.19 mmol) of the title compound of Example 18c and 4.17 g (36.28 mmol) of N-hydroxysuccinimide are dissolved in 20 ml of chloroform and 7.48 g (36.23 mmol) of dicyclohexylcarbodiimide is added at 0° C. It is stirred for 24 hours at room temperature. It is cooled in an ice bath and filtered off from precipitated urea. The filtrate is evaporated to dryness in a vacuum and the residue is recrystallized from a little isopropanol.

Yield: 12.03 g (93% of theory) of a light yellowish crystalline solid

Analysis:

Cld: C, 56.08; H, 3.76; N, 6.54.

Fnd: C, 56.17; H, 3.84; N, 6.41.

e) Gadolinium complex of 10-[6-(4-nitro-2-(benzyloxycarbonyl)-phenoxy)-2-hydroxy-5-oxo-4-aza-hexyl]-1,4,7-tris(carboxymethyl)-1,4,7,10-tetraazacyclododecane 13.26 g (23.11 mmol) of the title compound of Example 18d is added to 11 g (25.68 mmol) of the title compound of Example 2b in 100 ml of dimethylformamide/20 ml of triethylamine at room temperature and stirred overnight. It is evaporated to dryness in a vacuum and the residue is chromatographed on RP-18 (LiChroPrep®/mobile solvent: water/tetrahydrofuran gradient).

Yield: 19.02 g (81% of theory) of an amorphous solid

Water content: 3.1%

Analysis (relative to anhydrous substance):
Cld: C, 44.69; H, 4.66; Gd, 17.73; N, 9.47.
Fnd: C, 44.48; H, 4.80; Gd, 17.56; N, 9.28.

f) Gadolinium complex of 10-[6-(4-amino-2-carboxy-phenoxy)-2-hydroxy-5-oxo-4-aza-hexyl]-1,4,7-tris(carboxymethyl)-1,4,7,10-tetraazacyclododecane 18 g (20.3 mmol) of the title compound of Example 18e is dissolved in 200 ml of methanol and 15 g of palladium catalyst (10% Pd on C) is added. It is hydrogenated for 8 hours at room temperature. The catalyst is filtered off and the filtrate is evaporated to dryness.

Yield: 15.88 g (98% of theory) of a cream-colored solid
Water content: 4.1%
Analysis (relative to anhydrous substance):
Cld: C, 40.72; H, 4.86; Gd, 20.51; N, 10.96.
Fnd: C, 40.51; H, 4.97; Gd, 20.32; N, 10.73.

g) Gadolinium complex of 10-[6-(4-isothiocyanato-2-carboxy-phenoxy)-2-hydroxy-5-oxo-4-aza-heptyl]-1,4,7-tris(carboxymethyl)-1,4,7,10-tetraazacyclododecane 15 g (19.56 mmol) of the title compound of Example 18f is dissolved in 100 ml of water and 6.75 g (58.7 mmol) of thiophosgene in 50 ml of chloroform is added. It is stirred for 1 hour at 50° C. It is cooled off to room temperature, the organic phase is separated and the aqueous phase is shaken out twice with 100 ml of chloroform. The aqueous phase is evaporated to dryness and the residue is absorptively precipitated in 100 ml of isopropanol at room temperature. The solid is filtered off and washed with ether. After drying overnight in a vacuum (40° C.), 16.5 g (98% of theory) of a cream-colored solid is obtained.

Water content: 5.8%
Analysis (relative to anhydrous substance):
Cld: C, 40.09; H, 4.36; Gd, 19.44; N, 10.39; S, 3.96.
Fnd: C, 40.15; H, 4.45; Gd, 19.23; N, 10.19; S, 3.87.

h) 64-Thiourea conjugate of the gadolinium complex of 10-[6-(4-isothiocyanato-2-carboxy-phenoxy)-2-hydroxy-5-oxo4-aza-hexyl]-1,4,7-tris(carboxymethyl)-1,4,7,10-tetraazacyclododecane with the unblocked 64-polyamine of Example 17h 1.74 g (0.1 mmol) of the 64-benzyloxycarbonylamine described in Example 17h is dissolved in glacial acetic acid and mixed with stirring with 33% hydrogen bromide in glacial acetic acid. After 3 hours, the incipient precipitation is completed with diethyl ether, the 64-amine-hydrobromide produced is washed with ether and dried in a vacuum. The residue is then taken up in water and adjusted to pH 9.5 by adding 1 N sodium hydroxide solution. 7.76 g (9.6 mmol) of the isothiocyanate, described in Example 18g above, in solid form, is added in portions to this solution, and the pH is kept constant at 9.5 by further addition of sodium hydroxide solution. After completion of the addition, it is stirred overnight at room temperature and then neutralized with diluted hydrochloric acid. The solution is ultrafiltered (Amicon YM3) and the retentate is freeze-dried.

Yield: 5.21 g (79% of theory)
$H_2O$ content (Karl Fischer): 6.0%
Gd determination (AAS): 15.1%
Elementary analysis (relative to anhydrous substance):
Cld: C, 41.14; H, 4.60; Gd, 16.22; N, 11.83; Na, 2.37; S, 3.31.
Fnd: C, 40.89; H, 4.70; Gd, 16.65; N, 11.90; Na, 2.08; S, 3.73.

Example 19 a) 3-(4-Isothiocyanatophenyl)-glutaric acid 11.5 g (100 mmol) of thiophosgene is added to 22.12 g (100 mmol) of 3-(4-aminophenyl)-glutaric acid in 300 ml chloroform and heated for 50 minutes at 40° C. It is evaporated to dryness and the residue is crystallized from a little isopropanol/ether.

Yield: 22.5 g (85% of theory) of a cream-colored crystalline solid
Analysis:
Cld: C, 54.33; H, 4.18; N, 5.28; S, 12.09.
Fnd: C, 54.17; H, 4.29; N, 5.14; S, 12.15.

b) Gadolinium complex of 10-{6-[4-(2-carboxy-1-carboxymethyl-ethyl)-phenyl]-2-hydroxy-5-thioxo-4,6-diazahexyl]-1,4,7-tris(carboxymethyl)-1,4,7,10-tetraazacyclododecane 20 g (37.2 mmol) of the title compound of Example 2c is dissolved in 200 ml of dimethylformamide/50 ml of triethylamine and 11.84 g (44.63 mmol) of the title compound of Example 19a is added. It is stirred overnight at room temperature. It is evaporated to dryness in a vacuum, the residue is dissolved in 200 ml of ethanol/30 ml of acetic acid and again concentrated by evaporation. This residue is chromatographed on RP-18 (LiChroPrep®/mobile solvent: gradient of water/tetrahydrofuran).

Yield: 26.22 g (81% of theory) of a cream-colored solid
Water content: 3.6%
Analysis (relative to anhydrous substance):
Cld: C, 41.52; H, 4.93; Gd, 18.74; N, 10.02; S, 3.82.
Fnd: C, 41.33; H, 5.05; Gd, 18.61; N, 10.17; S, 3.75.

c) Gd complex of 10-{6-[4-(2,6-dioxo-3,4,5,6-tetrahydro-2H-pyran-4-yl)-phenyl]-2-hydroxy-5-thioxo-4,6-diazahexyl}-1,4,7-tris(carboxymethyl)-1,4,7,10-tetraazacyclododecane 10 g (11.92 mmol) of the title compound of Example 19b is dissolved in 50 ml of dimethylformamide and 3.7 g (17.88 mmol) of dicyclohexylcarbodiimide is added at 0° C. It is stirred overnight at room temperature. It is cooled off to 0° C. and filtered off from precipitated urea. 500 ml of ether is subsequently instilled in the filtrate with stirring. After drying overnight in a vacuum (50° C.), 9.6 g (95% of theory) of the title compound is obtained as slightly yellowish solid.

Water content: 2.7%
Analysis (relative to anhydrous substance):
Cld: C, 42.43; H, 4.79; Gd, 19.15; N, 10.24; S, 3.91.
Fnd: C, 42.28; H, 4.93; Gd, 19.03; N, 10.05; S, 3.83.

d) 64-Amide conjugate of the gadolinium complex of 10-{6-[4-(2,6-dioxo-3,4,5,6-tetrahydro-2H-pyran-4-yl)-phenyl]-2-hydroxy-5-thioxo-4,6-diazahexyl}-1,4,7-tris(carboxymethyl)-1,4,7,10-tetraazacyclododecane with the unblocked 64-polyamine of Example 17h 1.74 g (0.1 mmol) of the 64-benzyloxycarbonylamine described in Example 17h is dissolved in glacial acetic acid and mixed with stirring with 33% hydrogen bromide in glacial acetic acid. After 3 hours, the incipient precipitate is completed with diethyl ether, the 64-amine-hydrobromide produced is washed with ether and dried in a vacuum. The residue is then taken up in water and adjusted to pH 9.5 by adding 1 N sodium hydroxide solution. 15.76 g (19.2 mmol) of the anhydride, described in Example 19c, in solid form is added in portions to this solution, and the pH is kept constant at 9.5 by further addition of sodium hydroxide solution. After completion of the addition, it is stirred overnight at room temperature and then neutralized with diluted hydrochloric acid. The solution is ultrafiltered (Amicon YM3) and the retentate is freeze-dried.

Yield: 5.64 g (83% of theory)

$H_2O$ content (Karl Fischer): 7.6%

Gd determination (AAS): 14.7%

Elementary analysis (relative to anhydrous substance):

Cld: C 43.08; H, 4.96; Gd, 16.02; N, 11.68; Na, 2.34; S, 3.27.

Fnd: C, 43.03; H, 4.97; Gd, 15.86; N, 11.69; Na, 2.05; S, 3.11.

Example 20 a) 10-[3-(4-Aminophenoxy)-2-hydroxypropyl]-1,4,7-tris(carboxymethyl)-1,4,7,10-tetraazacyclododecane 15 g (27.7 mmol) of 10-[3-(4-nitrophenoxy)-2-hydroxypropyl]-1,4,7-tris(carboxymethyl)-1,4,7,10-tetraazacyclododecane (EP 0485045 (Schering AG), Example 12a), is dissolved in 250 ml of methanol and 5 g of palladium catalyst (10% Pd on activated carbon) is added. It is hydrogenated overnight at room temperature. The catalyst is filtered off and the filtrate is evaporated to dryness in a vacuum.

Yield: 14.43 g (98% of theory) of a cream-colored solid

Water content: 3.8%

Analysis (relative to anhydrous substance):

Cld: C, 54.00; H, 7.29; N, 13.69.

Fnd: C, 53.88; H, 7.41; N, 13.51.

b) 10-[3-{4-Bis(carboxymethyl)-aminophenoxy}-2-hydroxypropyl]-1,4,7-tris(carboxymethyl)-1,4,7,10-tetraazacyclododecane 14 g (27.37 mmol) of the title compound of Example 20a, 15.21 g (109 mmol) of bromoacetic acid and 41.5 g (300 mmol) of potassium carbonate in 200 ml of ethanol are refluxed for 2 days. It is filtered off from the solid, and 50 ml of concentrated hydrochloric acid is added to the filtrate. It is evaporated to dryness in a vacuum. The residue is purified on RP-18 (LiChroPrep®/mobile solvent: tetrahydrofuran/water gradient).

Yield: 7.81 g (43% of theory) of a cream-colored solid

Water content: 5.4%

Analysis (relative to anhydrous substance):

Cld: C, 51.67; H, 6.58; N, 11.16.

Fnd: C, 51.48; H, 6.71; N, 11.03.

c) Gadolinium complex of 10-[3-{4-bis(carboxymethyl)-aminophenoxy}-2-hydroxy-propyl]-1,4,7-tris(carboxymethyl)-1,4,7,10-tetraazacyclododecane 100 ml of water is added to 7.5 g (11.95 mmol) of the title compound of Example 20b and 2.17 g (5.97 mmol) of gadolinium oxide, and it is stirred for 3 hours at 90° C. It is allowed to cool off to room temperature and then stirred for one hour with 3 ml of acid cation exchanger (IR-120/$H^+$ form). The exchanger is filtered off, and the filtrate is freeze-dried.

Yield: 10.18 (97%of theory) of an amorphous powder

Water content: 11.3%

Analysis (relative to anhydrous substance):

Cld: C, 41.48; H, 4.90; Gd, 20.11; N, 8.96.

Fnd: C, 41.27; H, 4.98; Gd, 19.93; N, 8.85.

d) Gadolinium complex of 10-{3-[4-(2,6-dioxomorpholino)-phenoxy]-2-hydroxypropyl}-1,4,7-tris(carboxymethyl)-1,4,7,10-tetraazacyclododecane 10 g (12.79 mmol) of the title compound of Example 20c is dissolved in 50 ml of dimethylformamide and 5.28 g (25.58 mmol) of dicyclohexylcarbodiimide is added at 0° C. It is stirred overnight at room temperature. It is cooled to 0° C. and filtered off from precipitated urea. 500 ml of ether is instilled in the filtrate with stirring, and the title compound crystallizes out. It is filtered off and rewashed with ether. After drying overnight in a vacuum (50° C.), 9.67 g (69% of theory) of the title compound is obtained as slightly yellowish amorphous solid.

Water content: 3.0%

Elementary analysis (relative to anhydrous substance):

Cld: C, 42.46; H, 4.75; Gd, 20.59; N, 9.17.

Fnd: C, 42.27; H, 4.91; Gd, 20.38; N, 9.03.

e) 64-Amide conjugate of the gadolinium complex of 10-{3-[4-(2,6-dioxomorpholino)-phenoxy]-2-hydroxypropyl}-1,4,7-tris(carboxymethyl)-1,4,7,10-tetraazacyclododecane with the unblocked 64-polyamine of Example 17h 1.74 g (0.1 mmol) of the 64-benzyloxycarbonylamine described in Example 17h is dissolved in glacial acetic acid and mixed with stirring with 33% hydrogen bromide in glacial acetic acid. After 3 hours, the incipient precipitation is completed with diethyl ether, the 64-amine-hydrobromide produced is washed with ether and dried in a vacuum. The residue is then taken up in water and adjusted to pH 9.5 by adding 1 N sodium hydroxide solution. 14.68 g (19.2 mmol) of the anhydride, described in Example 20d above, in solid form is added in portions to this solution, and the pH is kept constant at 9.5 by further addition of sodium hydroxide solution. After completion of the addition, it is stirred overnight at room temperature and then neutralized with diluted hydrochloric acid. The solution is ultrafiltered (Amicon YM3) and the retentate is freeze-dried.

Yield: 5.00 g (78% of theory)

$H_2O$ content (Karl Fischer): 7.7%

Gd determination (AAS): 15.7%

Elementary analysis (relative to anhydrous substance):

Cld: C, 43.15; H, 4.93; Gd, 17.01; N, 10.89; Na, 2.49.

Fnd: C, 43.17; H, 4.89; Gd, 16.80; N, 10.54; Na, 2.33.

Example 21 a) Meso-2,3-bis(benzyloxycarbonylamino)succinic acid 14.81 g (100 mmol) of diaminosuccinic acid (meso form) is suspended in 300 ml of tetrahydrofuran and adjusted to pH 9 with 2 N sodium hydroxide solution. 42.65 g (250 mmol) of benzyl chloroformate, dissolved in 50 ml of tetrahydrofuran, is instilled at 0° C. with vigorous stirring and the pH is kept at 9 with simultaneous addition of 2 N sodium hydroxide solution. Then, it is allowed to stir for 5 more hours at pH 9 and room temperature. It is adjusted with 10% hydrochloric acid to pH 2 and 300 ml of saturated common salt solution is added. The organic phase is separated, evaporated to dryness in a vacuum, and the residue is chromatographed on silica gel (mobile solvent: methylene chloride/methanol 10:1 (2% acetic acid).

Yield: 27.07 g (65% of theory) of a colorless solid
Elementary analysis:
Cld: C, 57.69; H, 4.84; N, 6.73.
Fnd: C, 57.59; H, 4.93; N, 6.66.

b) 2,3-Bis(benzyloxycarbonylamino)-succinic anhydride 25 g (60.04 mmol) of the title compound of Example 21a is stirred in 200 ml of acetic anhydride for 12 hours at 50° C. It is cooled in an ice bath to 0° C., and 600 ml of diethyl ether is slowly instilled. The crystals are filtered off, rewashed twice with 100 ml of ether each and dried overnight in a vacuum (50° C.).

Yield: 23.44 g (98% of theory) of colorless flakes
Elementary analysis:
Cld: C, 60.30; H, 4.55; N, 7.03.
Fnd: C, 60.15; H, 4.65; N, 6.94.

c) Completely protected benzyloxycarbonyl-32-amine based on the (diamino)-succinylated N,N', N'',N'''-tetrakis[trilysyl-aminoethyl]-methane 10 g (2.62 mmol) of the title compound of Example 17d is dissolved in 100 ml of glacial acetic acid and 33% hydrogen bromide in glacial acetic acid is added with stirring (100 ml). After 2 hours, the incipient precipitation is completed with diethyl ether, the hexadecabromide produced is filtered off and washed with diethyl ether and used without further purification in the further reaction (quantitative yield). The thus obtained hydrobromide is dissolved in 200 ml of pyridine and 20 ml of triethylamine and 1 g (8.18 mmol) of 4-dimethylaminopyridine is added. 33.40 g (83.84 mmol) of title compound 21b, dissolved in 100 ml of dimethylformamide, is instilled at 0° C. and then stirred overnight at room temperature. It is evaporated to dryness in a vacuum, the residue is taken up in 300 ml of methylene chloride and washed 3 times with 100 ml each of 5% potassium carbonate solution. The organic phase is dried on magnesium sulfate and concentrated by evaporation in a vacuum. The residue is chromatographed on silica gel (mobile solvent: methylene chloride/methanol 20:1).

Yield: 17.07 g (81% of theory) of a colorless solid
Elementary analysis:
Cld: C, 59.28; H, 5.61; N, 10.45.
Fnd: C, 59.13; H, 5.79; N, 10.29.

d) 1-Hydroxy-11-(4-nitrophenoxy)-3,6,9-trioxaundecane 18.16 g (128.7 mmol) of 4-fluoronitrobenzene is added to 100 g (515.0 mmol) of tetraethylene glycol, 73 g (1300 mmol) of finely powdered potassium hydroxide and 500 mg of tetrabutylammonium hydrogen sulfate in 500 ml of toluene at 0° C., and it is stirred overnight at room temperature. 1000 ml of saturated common salt solution is; added, the organic phase is separated and it is dried on magnesium sulfate. It is evaporated to dryness in a vacuum, and the residue is chromatographed in silica gel (mobile solvent: methylene chloride/isopropanol=15:1).

Yield: 27.19 g (67% of theory) of a yellowish oil which solidifies with standing
Analysis:
Cld: C, 53.33; H, 6.71; N, 4.44.
Fnd: C, 53.20; H, 6.85; N, 4.28.

e) 1-tert-Butoxy-13-(4-nitrophenoxy)-2,5,8,11-tetraox-atridecane 18.6 g (95.1 mmol) of bromoacetic acid-tert-butyl ester is added to 25 g (79.28 mmol) of the title compound of Example 21d, 8.9 g (158.6 mmol) of finely powdered potassium hydroxide and 200 mg of tetrabutylammonium hydrogen sulfate in 300 ml of toluene at 0° C., and it is stirred for 3 hours at 0° C. 200 ml of water is added, the organic phase is separated, and it is dried on magnesium sulfate. It is evaporated to dryness in a vacuum, and the residue is chromatographed on silica gel (mobile solvent: methylene chloride/acetone=10:1).

Yield: 29.6 g (87% of theory) of a yellowish, viscous oil
Analysis:
Cld: C, 55.93; H, 7.28; N, 3.26.
Fnd: C, 55.78; H, 7.41; N, 3.15.

f) 1-Carboxy-13-(4-nitrophenoxy)-2,5,8,11-tetraoxa-tridecane 28 g (65.2 mmol) of the title compound of Example 21e is dissolved in 200 ml of methylene chloride. 150 ml of trifluoroacetic acid is instilled at 0° C. and allowed to come to room temperature. After 1 hour, it is evaporated to dryness. The residue is recrystallized from a little ether/hexane.

Yield: 23.4 g (96% of theory) of a light yellowish solid
Analysis:
Cld: C, 51.47; H, 6.21; N, 3.75.
Fnd: C, 51.38; H, 6.31; N, 3.61.

g) N-Hydroxysuccinimide-ester of 1-carboxy-13-(4-nitrophenoxy)-2,5,8,11-tetraoxa-tridecane 10 g (26.78 mmol) of the title compound of Example 21f and 3.7 g (32.14 mmol) of N-hydroxysuccinimide are dissolved in 20 ml of chloroform and 6.63 g (32.14 mmol) of dicyclohexylcarbodiimide is added at 0° C. It is stirred for 24 hours at room temperature. It is cooled in an ice bath and filtered off from precipitated urea. The filtrate is evaporated to dryness in a vacuum, and the residue. is recrystallized from a little isopropanol.

Yield: 11.21 g (89% of theory) of a light yellowish, crystalline solid
Analysis:
Cld: C, 51.06; H, 5.57; N, 5.95.
Fnd: C, 51.17; H, 5.61; N, 5.83.

h) Gadolinium complex of 10-[18-(4-nitrophenoxy)-2-hydroxy-5-oxo-4-aza-7,10,13,16-tetraaza-octadecyl]-1,4,7-tris(carboxymethyl)-1,4,7,10-tetraazacyclododecane 9.84 g (20.92 mmol) of the title compound of Example 21g is added to 10 g (17.43 mmol) of the title compound of Example 2c in 100 ml of dimethylformamide/20 ml of triethylamine at room temperature, and it is stirred overnight. It is evaporated to dryness in a vacuum, and the residue is chromatographed on RP-18 (LiChroPrep®/mobile solvent: water/tetrahydrofuran gradient).

Yield: 14.3 g (83% of theory) of an amorphous solid

Water content: 5.8%

Analysis (relative to anhydrous substance):

Cld: C, 42.66; H, 5.53; Gd, 16.93; N, 9.05.

Fnd: C, 42.51; H, 5.68; Gd, 16.80; N, 9.15.

i) Gadolinium complex of 10-[18-(4-aminophenoxy)-2-hydroxy-5-oxo-4-aza-7,10,13,16-tetraoxa-octadecyl]-1,4,7-tris(carboxymethyl)-1,4,7,10-tetraazacyclododecane 14 g (15.07 mmol) of the title compound of Example 21h is dissolved in 200 ml of methanol and 4 g of palladium catalyst (10% Pd on C) is added. It is hydrogenated for 8 hours at room temperature. The catalyst is filtered off, and the filtrate is evaporated to dryness.

Yield: 13.41 g (99% of theory) of a cream-colored solid

Water content: 6.1%

Analysis (relative to anhydrous substance):

Cld: C, 44.09; H, 5.94; Gd, 17.49; N, 9.35.

Fnd: C, 43.93; H, 6.10; Gd, 17.28; N, 9.22.

k) Gadolinium complex of 10-[18-(4-isothiocyanatophenoxy)-2-hydroxy-5-oxo-4-aza-7,10,13,16-tetraoxaoctadecyl]-1,4,7-tris(carboxymethyl)-1,4,7,10-tetraazacyclododecane 10 g (11.12 mmol) of the title compound of Example 21i is dissolved in 100 ml of water and 3.834 g (33.36 mmol) of thiophosgene in 50 ml of chloroform is added. It is stirred for 1 hour at 50° C. It is cooled to room temperature, the organic phase is separated and the aqueous phase is shaken out twice with 100 ml of chloroform. The aqueous phase is evaporated to dryness, and the residue is absorptively precipitated in 100 ml of acetone at room temperature. The solid is filtered off and washed with ether. After drying overnight in a vacuum (40° C.), 10.47 g 97% of theory) of a cream-colored solid is obtained.

Water content: 3.0%

Analysis (relative to anhydrous substance):

Cld: C, 43.39; H, 5.46; Gd, 16.71; N, 8.93; S, 3.41.

Fnd: C, 43.20; H, 5.60; Gd, 16.53; N, 8.75; S, 3.36.

l) 32-Thiourea conjugate of the gadolinium complex of 10-[18-(4-isothiocyanatophenoxy)-2-hydroxy-5-oxo-4-aza-7,10,13,16-tetraoxaoctadecyl]-1,4,7-tris(carboxymethyl)-1,4,7,10-tetraazacyclododecane with the unblocked 32-amine of Example 21c 1.61 g (0.2 mmol) of the 32-benzyloxycarbonylamine described in Example 21c is dissolved in glacial acetic acid and mixed with stirring with 33% hydrogen bromide in glacial acetic acid. After 3 hours, the incipient precipitation is completed with diethyl ether, the 32-amine-hydrobromide produced is washed with ether and dried in a vacuum. The residue is then taken up in water and adjusted to pH 9.5 by adding 1 N sodium hydroxide solution. 9.03 g (9.6 mmol) of the isothiocyanate, described in Example 21k above, in solid form is added in portions to this solution, and the pH is kept constant at 9.5 by further addition of sodium hydroxide solution. After completion of the addition, it is stirred overnight at room temperature and then neutralized with diluted hydrochloric acid. The solution is ultrafiltered (Amicon YM3) and the retentate is freeze-dried.

Yield: 6.10 g (86% of theory)

$H_2O$ content (Karl Fischer): 3.5%

Gd determination (AAS): 14.0%

Elementary analysis (relative to anhydrous substance):

Cld: C, 43.14; H, 5.51; Gd, 14.70; N, 10.31; Na, 1.07 S, 3.00.

Fnd: C, 42.96; H, 5.72; Gd, 14.50; N, 10.39; Na, 0.94 S, 2.76.

Example 22

32-Thiourea conjugate of the gadolinium complex of 10-[3-(4-isothiocyanatophenoxy)-2-hydroxy-propyl]-1,4,7-tris(carboxymethyl)-1,4,7,10-tetraazacyclododecane with the unblocked 32-amine of Example 21c 1.61 g (0.2 mmol) of the 32-benzyloxycarbonylamine described in Example 21c is dissolved in glacial acetic acid and mixed with stirring with 33% hydrogen bromide in glacial acetic acid. After 3 hours, the incipient precipitation is completed with diethyl ether, the 32-amine-hydrobromide produced is washed with ether and dried in a vacuum.

The residue is then taken up in water and adjusted to pH 9.5 by adding 1 N sodium hydroxide solution. 6.80 g (9.6 mmol) of the isothiocyanate, described in Example 12d of EP-485045 (Nov. 8, 1990), in solid form is added in portions to this solution, and the pH is kept constant at 9.5 by further addition of sodium hydroxide solution. After completion of the addition, it is stirred overnight at room temperature and then neutralized with diluted hydrochloric acid. The solution is ultrafiltered (Amicon YM3) and the retentate is freeze-dried.

Yield: 4.56 g (82% of theory)

$H_2O$ content (Karl Fischer): 4.0%

Gd determination (AAS): 17.9%

Elementary analysis (relative to anhydrous substance):

Cld: C, 40.81; H, 4.76; Gd, 18.81; N, 11.52; Na, 1.37 S, 3.85.

Fnd: C, 40.67; H, 4.98; Gd, 18.60; N, 11.70; Na, 1.21 S, 3.47.

Example 23 a) Hexakis-N-[2-aminoethyl]-[1,3,5]-triazine-2,4,6-triyltriamine 18.41 g (100 mmol) of 2,4,6-trichloro-s-triazine and 92.99 g (315 mmol) of bis-(2-trifluoroacetyl-aminoethyl)amine (produced according to U.S. Pat. No. 4,415,737) are suspended in a mixture of 300 ml of water and 300 ml of dioxane. The temperature is increased to 50° C. with stirring. The pH is kept at 7–8 by instillation of a saturated solution of potassium hydrogen-carbonate. If the pH is no longer changed, it is increased to 9 by adding 1 N potassium hydroxide solution, and the temperature is increased for 30 minutes to 70° C. Then, it is concentrated by evaporation in a vacuum to ¹⁄₁₀ of the original volume, cooled in an ice bath and the precipitate is separated by suction. The residue is recrystallized from isopropyl alcohol. 29 g of the title compound is obtained, flash point 168–172° C.

Elementary analysis (relative to anhydrous substance):
Cld: C, 46.85; H, 9.44; N, 43.71.
Fnd: C, 46.62; H, 9.80; N, 43.92.

b) Completely protected benzyloxycarbonyl-24-polyamine based on hexakis-N-[2-(trilysyl-amino)-ethyl]-[1,3,5]triazine-2,4,6-triyltriamine 7.0 g (7.5 mmol) of the protected "trilysine" described in Example 1c, 1.2 g (7.5 mmol) of 1-hydroxybenzotriazole and 2.4 g (7.5 mmol) of 2-(1H-benzotriazol-1-yl)-1,1,3,3-tetramethyluronium tetrafluoroborate (TBTU) are dissolved in 100 ml of DMF and stirred for 15 minutes. The solution is then mixed with 5.16 ml (30 mmol) of N-ethyldiisopropylamine and 385 mg (1 mmol) of hexakis-N-[2-aminoethyl]-[1,3,5]triazine-2,4,6-triyltriamine (Example 23a) and stirred overnight at room temperature. After completion of the reaction, it is concentrated by evaporation in a vacuum and the residue is chromatographed on silica gel with ethyl acetate/ethanol (3:1).

Yield: 4.02 g (68% of theory)
Elementary analysis:
Cld: C, 63.98; H, 6.80; N, 11.37.
Fnd: C, 64.15; H, 7.19; N, 11.51.

c) 24-Gadolinium-DTPA-monoamide based on hexakis-N-[2-(trilysyl-amino)-ethyl]-[1,3,5]-triazine-2,4,6-triyltriamine 1.18 g (0.2 mmol) of the poly-benzyloxycarbonylamine described in Example 23b is dissolved in glacial acetic acid and mixed with stirring with 33% hydrogen bromide in glacial acetic acid. After 3 hours, the incipient precipitation is completed with diethyl ether, the 24-amine-hydrobromide produced is washed with ether and dried in a vacuum. The residue is then taken up in water and adjusted to pH 9.5 by adding 1 N sodium hydroxide solution. 5.8 g (14.4 mmol) of $N^3$-(2,6-dioxomorpholinoethyl)-$N^6$-(ethoxycarbonylmethyl)-3,6-diazaoctanedioic acid (Example 13a of EP 0331 616) in solid form is added to this solution, and the pH is kept constant at 9.5 by further addition of sodium hydroxide solution. After completion of the addition, it is adjusted to pH>13 with 5 N sodium hydroxide solution for saponification of the DTPA-ethyl ester, and it is stirred overnight at room temperature. Then, it is adjusted to pH 5 with concentrated hydrochloric acid, mixed with 2.61 g (7.2 mmol) of $Gd_2O_3$, stirred for 30 minutes at 80° C., adjusted to pH 7 after the cooling and desalinated on a Ym3 AMICON-ultrafiltration membrane. The retentate is finally membrane-filtered and freeze-dried.

Yield: 3.38 g (88% of theory)
$H_2O$ content (Karl Fischer): 7.3%
Gd determination (AAS): 20.1%
Elementary analysis (relative to anhydrous substance):
Cld: C, 40.78; H, 4.37; Gd, 19.68; N, 8.77; Na, 2.88.
Fnd: C, 41.03; H, 4.61; Gd, 19.82; N, 8.98; Na, 3.01.

The dysprosium complex is obtained analogously with $Dy_2O_3$:
Elementary analysis (relative to anhydrous substance):
Cld: C, 40.51; H, 4.34; Dy, 20.21; N, 8.71; Na, 2.86.
Fnd: C, 40.39; H, 4.60; Dy, 19.90; N, 8.95; Na, 2.62.

Example 24 a) 1,4,7,10,13,16-Hexakis[benzyloxycarbonylglycyl]-1,4,7,10,13,16-hexaazacyclooctadecane 516 mg (2 mmol) of 1,4,7,10,13,16-hexaazacyclooctadecane (hexacyclene; Fluka) is azeotropically dehydrated with toluene. A solution of 3.14 g (15 mmol) of benzyloxycarbonyl-glycine (Fluka) in tetrahydrofuran (THF) as well as 3.71 g (15 mmol) of 2-ethoxy-1-ethoxycarbonyl-1,2-dihydroquinoline (EEDQ; Fluka) are added to the cooled solution of hexacyclene in toluene at room temperature and stirred overnight. After completion of the reaction, the product is precipitated by adding hexane, and the precipitate is chromatographed with dichloromethane/hexane/isopropanol (20:10:1) on silica gel.

Yield: 1.83 g (65%)
Elementary analysis:
Cld: C, 61.53; H, 6.02; N, 11.96.
Fnd: C, 61.40; H, 5.96; N, 12.08.

b) 1,4,7,10,13,16-Hexakis[N,N-bis(benzyloxycarbonylaminoethyl)-glycyl]-1,4,7,10,13,16-hexaazacyclooctadecane 1.41 g (1 mmol) of the hexa-benzyloxycarbonylamine described in the example above is dissolved in glacial acetic acid and mixed with stirring with 33% hydrogen bromide in glacial acetic acid. After 60 minutes, the incipient precipitation is completed with diethyl ether, the hexa-amine-hydrobromide produced is washed with ether, dried in a vacuum and used without further purification in the reaction further described below.

Yield: 1.09 g (quantitative)

1.09 g (1 mmol) of the thus produced hydrobromide is suspended in 50 ml of acetonitrile and 3 ml of triethylamine is added. Then, 3.54 g (20 mmol) of N-benzyloxycarbonylaziridine (produced according to J. Chem. Soc. Perkin Trans., 1, 21–26, 1993) is added and refluxed for 5 days under nitrogen. It is evaporated to dryness, taken up with 100 ml of methylene chloride and washed twice with 100 ml each of 5 potassium carbonate solution. The methylene chloride phase is dried on magnesium sulfate and concentrated by evaporation. The residue is chromatographed on silica gel (mobile solvent: methylene chloride/methanol/triethylamine 20:1:0.1).

Yield: 2.29 g (84% of theory) of a pale yellow viscous oil
Elementary analysis:
Cld: C, 63.42; H, 6.65; N, 12.33.
Fnd: C, 63.29; H, 6.60; N, 12.47.

c) Completely protected benzyloxycarbonyl-24-polyamine from the 12-amine 1,4,7,10,13,16-hexakis[N,N-bis(aminoethyl)glycyl]-1,4,7,10,13,16-hexaazacyclooctadecane alkylated with benzyloxycarbonylaziridine 1.36 g (0.5 mmol) of the title compound of Example 24b is dissolved in 100 ml of methanol and 3 g of Pearlman's catalyst (palladium hydroxide on activated carbon; Fluka) is added. It is hydrogenated for 10 hours at 5 bars (room temperature). It is filtered off from the catalyst, the filtrate is evaporated to dryness and used without further purification in the following reaction.

Yield: 0.56 g (quantitative)

3.54 g (20 mmol) of N-benzyloxycarbonylaziridine (produced according to J. Chem. Soc., Perkin Trans. 1, 21–26, 1993) is added to 0.56 g (0.5 mmol) of the thus produced free 12-amine in 50 ml of acetonitrile, and it is refluxed for 5 days under nitrogen. It is evaporated to dryness, taken up with 100 ml of methylene chloride and washed twice with 100 ml each of 5% potassium carbonate solution. The methylene chloride phase is dried on magnesium sulfate and concentrated by evaporation. The residue is chromatographed on silica gel (mobile solvent: methylene chloride/methanol/triethylamine 20:1:0.1).

Yield: 2.23 g (83% of theory) of a pale yellow viscous oil
Elementary analysis:
Cld: C, 64.41; H, 6.98; N, 12.52.
Fnd: C, 64.20; H, 7.15; N, 12.44.

d) 24-Gadolinium-DTPA-monoamide based on the unblocked 24-amine of Example 24c 1.07 g (0.2 mmol) of the title compound of Example 24c is dissolved in glacial acetic acid and mixed with stirring with 33% hydrogen bromide in glacial acetic acid. After 3 hours, the incipient precipitation is completed with diethyl ether, the 24-amine-hydrobromide produced is washed with ether and dried in a vacuum.

The residue is then taken up in water and adjusted to pH 9.5 by adding 1 N sodium hydroxide solution. 5.8 g (14.4 mmol) of $N^3$-(2,6-dioxomorpholinoethyl)-$N^6$-(ethoxycarbonylmethyl)-3,6-diazaoctanedioic acid (Example 13a of EP 0331 616) in solid form is added to this solution, and the pH is kept constant at 9.5 by further addition of sodium hydroxide solution. After completion of the addition, it is adjusted to pH>13 with 5 N sodium hydroxide solution for saponification of the DTPA-ethyl ester, and it is stirred overnight at room temperature. Then, it is adjusted to pH 5 with concentrated hydrochloric acid, mixed with 2.61 g (7.2 mmol) of $Gd_2O_3$, stirred for 30 minutes at 80° C., adjusted to pH 7 after cooling off and desalinated with a Ym3 AMICON-ultrafiltration membrane. The retentate is finally membrane-filtered and freeze-dried.

Yield: 2.90 g (89% of theory)
$H_2O$ content (Karl Fischer): 8.0%
Gd determination (AAS): 23.4%
Elementary analysis (relative to anhydrous substance):
Cld: C, 34.61; H, 4.40; Gd, 25.17; N, 11.21; Na, 0.92.
Fnd: C, 34.34; H, 4.50; Gd, 24.93; N, 11.06; Na, 1.10.

Example 25

Example for the Form of Administration a) 24-Calcium-DTPA-monoamide based on N,N,N', N',N",N"-hexakis[2-(trilysyl-amino)-ethyl]trimesic acid triamide 1.20 g (0.2 mmol) of the poly-benzyloxycarbonylamine described in Example 1d is dissolved in glacial acetic acid and mixed with stirring with 33% hydrogen bromide in glacial acetic acid. After 3 hours, the incipient precipitation is completed with diethyl ether, the 24-amine-hydrobromide produced is washed with ether and dried in a vacuum. The residue is then taken up in water and adjusted to pH 9.5 by adding 1 N sodium hydroxide solution. 5.8 g (14.4 mmol) of $N^3$-(2,6-dioxomorpholinoethyl)-$N^6$-(ethoxycarbonylmethyl)-3,6-diazaoctanedioic acid (Example 13a of EP 0331 616) in solid form is added to this solution, and the pH is kept constant at 9.5 by further addition of sodium hydroxide solution. After completion of the addition, it is adjusted to pH>13 with 5 N sodium hydroxide solution for saponification of the DTPA-ethyl ester, and it is stirred overnight at room temperature. Then, it is adjusted to pH 4.5 by adding cation exchanger (Amberlite IR 120, $H^+$ form), filtered off from the exchanger, and the filtrate is mixed with 1.07 g of calcium hydroxide (14.4 mmol). The solution is then adjusted to pH 7 with diluted sodium hydroxide solution and ultrafiltered with a YM3 AMICON membrane, the retentate is finally membrane-filtered and freezed-dried.

Yield: 2.76 g (95% of theory)
$H_2O$ content (Karl Fischer): 7.2%
Elementary analysis (relative to anhydrous substance and calculated as 1.5 sodium salt per complex):
Cld: C, 41.42; H, 5.04; Ca, 7.13; N, 12.15; Na, 6.14.
Fnd: C, 41.09; H, 5.33; Ca, 6.97; N, 12.30; Na, 6.52.

b) Production of a solution of the gadolinium-cascade polymer described in Example 1

16.68 g (0.025 mol of gadolinium) of the compound described in Example 1e is dissolved in 60 ml of water pro injectione (p.i.). After adding 702 mg (1.25 mmol of calcium) of the Ca complex, described in the example above, and 121 mg of tris-hydroxymethylaminomethane, it is adjusted to pH 7.0 with diluted hydrochloric acid and filled with water p.i. to 100 ml. The solution is ultrafiltered, bottled and heat-sterilized.

Example 26 a) 4,7,13,16,21,24-Hexakis{8-(benzyloxycarbonylamino)-6-[2-(benzyloxycarbonylaminoethyl]-5-oxo-3-oxaoctanoyl}octaazabicyclo[8.8.8]hexacosane 741 mg (2 mmol) of 1,4,7,10,13,16,21,24-octaazabicyclo [8.8.8]hexacosane [P. H. Smith et al., J. Org. Chem. (1993), 58, 7939] is azeotropically dehydrated with toluene. A solution of 7.32 g (15 mmol) of N,N'-bis (benzyloxycarbonyl)-3-[carboxymethoxyacetyl]-3-azapentane-1,5-diamine (Example 7a) in tetrahydrofuran (THF) as well as 3.71 g (15 mmol) of 2-ethoxy-1-ethoxy-carbonyl-1,2-dihydroquinoline (EEDQ; Fluka) are added to the cooled solution of the bicyclic compound in toluene at room temperature and stirred overnight. After completion of the reaction, the product is precipitated by the addition of hexane, decanted from the solvent and reprecipitated once more from THF/hexane and then from THF/toluene. After drying in a vacuum, 4.53 g (71% of theory) of a pale yellow solid is obtained.

Elementary analysis:
Cld: C, 61.04; H, 6.45; N, 11.42.
Fnd: C, 60.89; H, 6.55; N, 11.61.

b) Completely protected 48-mer benzyloxycarbonyl-polyamine based on the 48-mer amine condensed from 4,7,13,16,21,24-hexakis{8-benzyloxycarbonylamino)-6-[2-(benzyloxycarbonylamino)-ethyl]-5-oxo-3-oxaoctanoyl}octaazabicyclo[8.8.8]hexacosane with $N^\alpha,N^\varepsilon$-bis(lysyl)-lysine ("trilysine")

3.19 g (1 mmol) of the 12-mer-benzyloxycarbonylamine described in Example 26a is dissolved in glacial acetic acid and mixed with stirring with 33% hydrogen bromide in glacial acetic acid. After 90 minutes, the incipient precipitation is completed with diethyl ether, the dodeca-amine-hydrobromide produced is washed with ether, dried in a vacuum and used without further purification in the reaction further described below.

Yield: 2.7 g (quantitative)
14.1 g (5 mmol) of the protected "trilysine" described in Example 1c, 2.25 g (15 mmol) of 1-hydroxybenzotriazole and 4.8 g (15 mmol) of 2-(1-H-benzotriazol-1-yl)-1,1,3,3-tetramethyluronium tetrafluoroborate {TBTU; Peboc Limited, UK) are dissolved in DMF and stirred for 15 minutes. This solution is then mixed with 7.74 ml (45 mmol) of N-ethyldiisopropylamine and with 2.7 g (1 mmol) of the above-described dodeca-amine-hydrobromide and stirred overnight at room temperature. After completion of the reaction, it is concentrated by evaporation in a vacuum and the residue is chromatographed with dichloromethane/methanol (10:1) on silica gel.

Yield: 9.4 g (74.4% of theory)

Elementary analysis:

Cld: C, 63.33; H, 6.80; N, 10.87.

Fnd: C, 63.14; H, 6.72; N, 10.98.

c) 48-mer-Gadolinium-DTPA-monoamide based on the unblocked 48-mer amine of Example 26b 2.53 g (0.2 mmol) of the poly-benzyloxycarbonylamine described in Example 26b is dissolved in glacial acetic acid and mixed with stirring with 33% hydrogen bromide in glacial acetic acid. After 3 hours, the incipient precipitation is completed with diethyl ether, the 48-mer-amine-hydrobromide produced is washed with ether and dried in a vacuum. The residue is then taken up in water and adjusted to pH 9.5 by the addition of 1N sodium hydroxide solution. 11.55 g (28.8 mmol) of $N^3$-(2,6-dioxomorpholinoethyl)-$N^6$-(ethoxycarbonylmethyl)-3,6-diazaoctanedioic acid (Example 13a of EP 0331 616) in solid form is added to this solution, and the pH is kept: constant at 9.5 by further addition of sodium hydroxide solution. After completion of the addition, it is adjusted to pH>13 for saponification of the DTPA-ethyl ester with 5 N sodium hydroxide solution and stirred overnight at room temperature. Then, it is adjusted to pH 5 with concentrated hydrochloric acid, mixed with 5.22 g (14.4 mmol) of $Gd_2O_3$, stirred for 30 minutes at 80° C., adjusted to pH 7 after the cooling and desalinated with a Ym3 AMICON-ultrafiltration membrane. The retentate is finally membrane-filtered and freeze-dried.

Yield: 5.90 g (83% of theory)

$H_2O$ content (Karl Fischer): 8.3%

Gd determination (AAS): 21.6%

Elementary analysis (relative to anhydrous substance):

Cld: C, 35.12; H, 4.27; Gd, 23.14; N, 10.39 Na, 3.24.

Fnd: C, 34.98; H, 4.50; Gd, 22.91; N, 10.54 Na, 3.09.

Example 27 a) 10-(Benzyloxycarbonylmethyl)-1,4,7-tris(tert-butyloxycarbonylmethyl)-1,4,7,10-tetraazacyclododecane (as sodium bromide complex)

20g (38.87 mmol) of 1,4,7-tris(tert-butyloxy-carbonylmethyl)-DO3A-tris-tert-butyl ester, produced according to EP 0 299 795, Example 22a), is dissolved in 100 ml of acetonitrile. Then, 11.45 g (50 mmol) of bromoacetic acid benzyl ester and 10.6 g (100 mmol) of sodium carbonate are added and stirred for 12 hours at 60° C. It is filtered off from the salts, the filtrate is evaporated to dryness in a vacuum and the residue is chromatographed on silica gel (mobile solvent: methylene chloride/methanol=20:1).

Yield: 21.72 g (73% of theory) of a colorless amorphous powder

Elementary analysis:

Cld: C, 54.90; H, 7.63; N, 7.32; Na, 3.00 Br, 10.44.

Fnd: C, 54.80; H, 7.72; N, 7.21; Na, 2.89 Br, 10.27.

b) 10-(Carboxymethyl)-1,4,7-tris(tert-butyloxycarbonylmethyl)-1,4,7,10-tetraazacyclododecane (as sodium bromide complex)

20 g (26.12 mmol) of the title compound of Example 27a is dissolved in 300 ml of isopropanol and 3 g of palladium catalyst (10% Pd/C) is added. It is hydrogenated overnight at room temperature. It is filtered off from the catalyst and the filtrate is evaporated to dryness.

Yield: 17.47 g (99% of theory) of a colorless amorphous powder

Elementary analysis:

Cld: C, 49.78; H, 7.76; N, 8.29; Na, 4.44; Br, 11.83.

Fnd: C, 49.59; H, 7.59; N, 8.17; Na, 4.40; Br, 11.70.

c) 24-mer N-(2-DO3Ayl-acetyl)-cascade polyamide based on the 24-mer amine N,N,N',N',N",N"-hexakis[2-(trilysylamino)-ethyl]-trimesic acid triamide 6.0 g (1 mmol) of the poly-benzyloxycarbonylamine described in Example 1d is dissolved in glacial acetic acid and mixed with stirring with 33% hydrogen bromide in glacial acetic acid. After 3 hours, the incipient precipitation is completed with diethyl ether, the 24-amine-hydrobromide produced is washed with ether and dried in a vacuum.

32.43 g (48 mmol) of the acid described in Example 27b above is dissolved in DMF, mixed with 7.35 g (48 mmol) of 1-hydroxybenzotriazole, with 15.41 g (48 mmol) of TBTU (Peboc Limited, UK) and with 49.3 ml (288 mmol) of N-ethyldiisopropylamine and stirred for 20 minutes at room temperature. This solution is then mixed with the above-described (1 mmol) 24-amine-hydrobromide and stirred for 4 days at room temperature. The solution is concentrated by evaporation in a vacuum, the remaining oil is cooled in an ice bath and mixed with trifluoroacetic acid, stirred overnight: at room temperature and then precipitated with diethyl ether. The precipitate is dried in a vacuum, taken up in water, adjusted to pH 7, purified with a YM3 Amicon®-ultrafiltration membrane of low-molecular portions and the retentate is finally membrane-filtered and freeze-dried.

Yield: 12.5 g (83% of theory)

$H_2O$ content (Karl Fischer): 9.7%

Elementary analysis (relative to anhydrous substance):

Cld: C, 45.21; H, 5.97; N, 14.49; Na, 12.15.

Fnd: C, 45.04; H, 6.15; N, 14.26; Na, 11.97.

d) 24-mer-Gd complex of the N-(DO3ayl-acetyl)-cascade polyamide based on the 24-mer amine N, N,N',N',N",N"-hexakis[2-(trilysylamino)-ethyl]-trimesic acid triamide 6.81 g (0.5 mmol) of the complexing agent acid described in Example 27c) above is adjusted to pH 3 in water with diluted hydrochloric acid, mixed with 2.17 g (6 mmol) of $Gd_2O_3$, stirred for 30 minutes at 80° C., adjusted to pH 7 after the cooling and desalinated with a Ym3 AMICON®-ultrafiltration membrane. The retentate is then provided with an IRA 67 (OH⁻ form) anion exchanger and with an IRC 50

(H⁺ form) cation exchanger for the separation of non-neutral by-products, and the obtained solution is finally membrane-filtered and freeze-dried.

Yield: 5.44 g (63.9% of theory)
H₂O content (Karl Fischer): 7.5%
Gd determination (AAS): 21.95%
Elementary analysis (relative to anhydrous substance):
Cld: C, 39.13; H, 5.16; N, 12.54; Gd, 23.97.
Fnd: C, 38.90; H, 5.29; N, 12.41; Gd, 23.55.

Example 28 a) 10-(4-Carboxy-2-oxo-3-azabutyl)-1,4,7-tris(tert-butoxycarbonylmethyl)-1,4,7,10-tetraazacyclododecane 1.73 g (15 mmol) of N-hydroxysuccinimide is added to 10 g (14.80 mmol) of the title compound of Example 27b) in 100 ml of dimethylformamide and cooled to 0° C. Then, 4.13 g (20 mmol) of dicyclohexylcarbodiimide is added and stirred for 1 hour at 0° C. and then for 2 hours at room temperature. It is cooled off to 0° C and then 5.1 g (50 mmol) of triethylamine and 2.25 g (30 mmol) of glycine are added. It is stirred overnight at room temperature. It is filtered off from precipitated urea and the filtrate is evaporated to dryness in a vacuum. The residue is taken up with water and extracted twice with methylene chloride. The organic phase is dried on magnesium sulfate and concentrated by evaporation in a vacuum. The residue is chromatographed on silica gel (mobile solvent: methylene chloride/methanol=15:1).

Yield: 8.20 g (88% of theory) of a colorless solid
Elementary analysis:
Cld: C, 57.21; H, 8.80; N, 11.12.
Fnd: C, 57.10; H, 8.91; N, 11.03.

b) 24-mer N-(5-DO3Ayl-4-oxo-3-azapentanoyl)-cascade polyamide based on the 24-mer amine N, N,N',N',N'',N''-hexakis[2-(trilysylamino)-ethyl]-trimesic acid triamide 6.0 g (1 mmol) of the poly-benzyloxycarbonylamine described in Example 1 d is dissolved in glacial acetic acid and mixed with stirring with 33% hydrogen bromide in glacial acetic acid. After 3 hours, the incipient precipitation is completed with diethyl ether, the 24-amine-hydrobromide produced is washed with ether and dried in a vacuum.

30.23 g (48 mmol) of the acid described in Example 28a) above is dissolved in DMF, mixed with 7.35 g (48 mmol) of 1-hydroxybenzotriazole, with 15.41 g (48 mmol) of TBTU (Peboc Limited, UK) and with 49.3 ml (288 mmol) of N-ethyldiisopropylamine and stirred for 20 minutes at room temperature. This solution is then mixed with the above-described (1 mmol) 24-amine-hydrobromide and stirred for 4 days at room temperature. The solution is concentrated by evaporation in a vacuum, the remaining oil is cooled in an ice bath and mixed with trifluoroacetic acid, stirred overnight at room temperature and then precipitated with diethyl ether. The precipitate is dried in a vacuum, taken up in water, adjusted to pH 7, purified with a YM3 Amicon®-ultrafiltration membrane of low-molecular portions, and the retentate is finally membrane-filtered and freeze-dried.

Yield: 12.9 g (79.2% of theory)
H₂O content (Karl Fischer): 7.9%
Elementary analysis (relative to anhydrous substance):
Cld: C, 44.93; H, 5.91; N, 15.41; Na, 11.04.
Fnd: C, 44.77; H, 6.15; N, 15.60; Na, 10.86.

c) 24-mer-Gd complex of the N-(5-DO3ayl-4-oxo-3-azapentanoyl)-cascade polyamide based on the 24-mer amine N,N,N',N',N'',N''-hexakis[2-(trilysylamino)-ethyl]-trimesic acid triamide 8.14 g (0.5 mmol) of the complexing agent acid described in Example 28b above is adjusted to pH 3 in water with diluted hydrochloric acid, mixed with 2.17 g (6 mmol) of Gd₂O₃, stirred for 30 minutes at 80° C., adjusted to pH 7 after the cooling and desalinated with a Ym3 AMICON®-ultrafiltration membrane. The retentate is then provided with an IRA 67 (OH⁻ form) anion exchanger and with an IRC 50 (H⁺ form) cation exchanger for the separation of non-neutral by-products, and the obtained solution is finally membrane-filtered and freeze-dried.

Yield: 6.3 g (67.7% of theory)
H₂O content (Karl Fischer): 8.0%
Gd determination (AAS): 19.6%
Elementary analysis (relative to anhydrous substance):
Cld: C, 39.37; H, 5.18; N, 13.50; Gd, 22.05.
Fnd: C, 39.44; H, 5.02; N, 13.73; Gd, 21.79.

Example for an In Vivo Comparison with an Extracellular Contrast Medium

The suitability of the compound described in Example 7d as blood-pool-agent is shown in the following test.

As test animals, five male (Schering-SPF) rats that are 300–350 g in weight are used. Before the test, the abdomen is opened, the intestines are shifted and then the renal vessels (arterial+venous) of both sides are ligated through the rear peritoneum with a surgical needle. Then, the abdominal cavity is closed again. 0.3 ml (respectively 50 mmol/L,) of the following contrast medium solution per animal is then administered intravenously: mixture of 1 part each of the compound of Example 7d, named compound 1 below, and the dysprosium complex of 10-(1-hydroxymethyl-2,3-dihydroxypropyl)-1,4,7-tris(carboxymethyl)-1,4,7,10-tetraazacyclododecane, produced analogously to the instructions in European Patent Application EP 448 191, named compound 2 below. Blood samples are taken with a catheter in the common carotid artery at the following times: 15, 30, 45, 60, 90 seconds, 3, 5, 10, 15 minutes p.i. In the blood samples obtained, the concentrations of gadolinium (Gd) and dysprosium (Dy) are measured with the aid of atomic emission spectrometry (ICP-AES) in each case in a parallel manner. The portion of the injected contrast medium of compound 1 (Gd) and compound 2 (Dy, comparison substance), remaining in the blood space, can be compared in the same animals by the different marking. Since a renal excretion is not possible, the decrease of the blood concentration can be attributed only to a distribution in the blood spaces and to the diffusion in the interstitial tissue.

Results: The diffusion of compound 1 in the interstitium is considerably slowed-down in comparison to an extracellular contrast medium compound 2 (see FIG. 1).

The extracellular contrast medium (compound 2) diffuses quickly into the interstitial spaces of the body, so that as early as after 1 minute p.i., an equilibrium is reached (displayed by constant blood level). In contrast to this, not only are constantly higher blood concentrations measured with the cascade polymer (compound 1) (reference to smaller volume of distribution), in addition no equilibrium is reached over the entire examination period of 15 minutes (reference to diffusion into interstitial tissue proceeding only very slowly). This means that compound 1 behaves as a blood-pool contrast medium.

Figure 1:
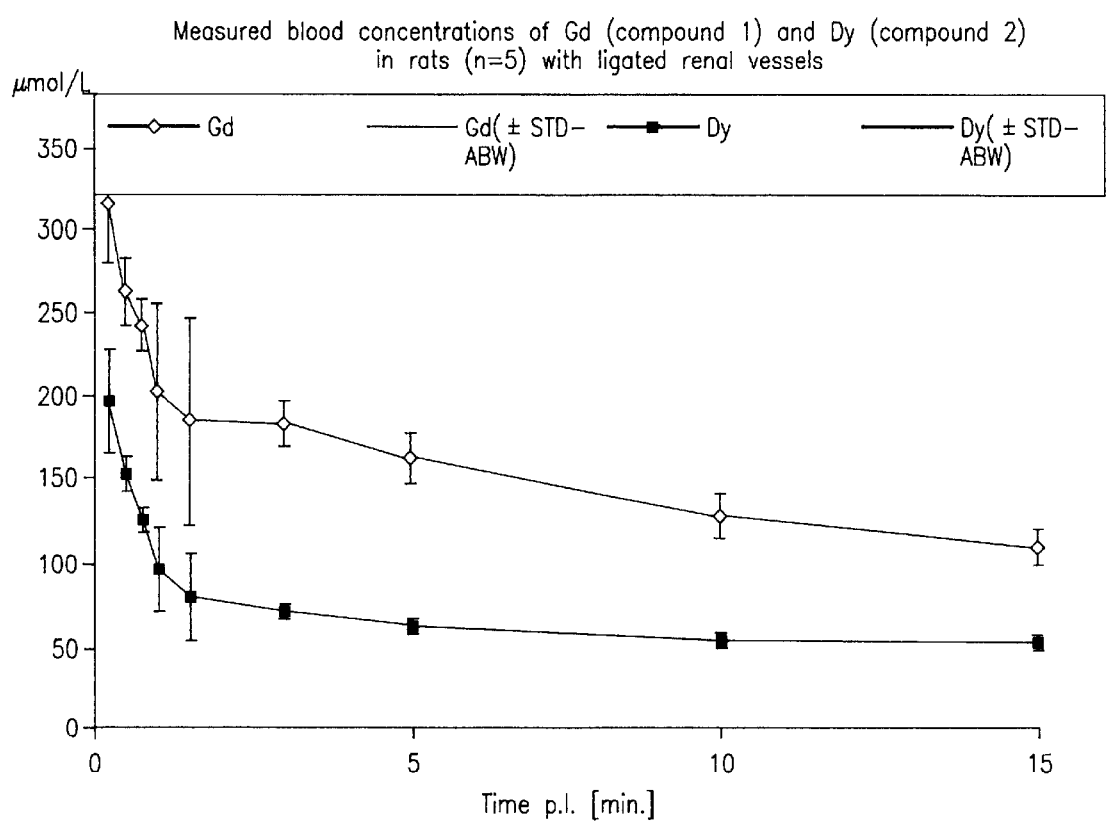
FIG. 1 is a graph of the measured blood concentrations of Gd (compound 1) and Dy (compound 2) in rats (n=5) with ligated renal vessels, as described in the last above Example.

What is claimed is:

1. A cascade polymer complex containing a) a complexing ligand of formula I

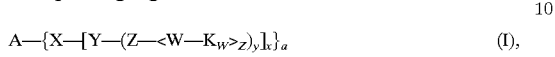

$$A-\{X-[Y-(Z-<W-K_W>_Z)_y]_x\}_a \quad (I),$$

in which

A stands for a nitrogen-containing cascade nucleus of base multiplicity a,

X and Y independently of one another, stand for a direct bond or a cascade reproduction unit of reproduction multiplicity x or y, Z and W, independently of one another, stand for a cascade reproduction unit of reproduction multiplicity z or w, K stands for the radical of a complexing agent, a stands for a number from 2 to 12, x, y, z and w, independently of one another, stand for a number 1 to 4, and terminal amino groups are optionally acylated, provided that at least two reproduction units are different and that $$16 \leq a \cdot x \cdot y \cdot z \cdot w \leq 64,$$

holds true for the product of the multiplicities, b) at least 16 ions of an element of atomic numbers 20 to 29, 39, 42, 44 or 57–83 and, c) optionally cations of inorganic and/or organic bases, amino acids or amino acid amides wherein at least one of cascade reproduction units X, Y, Z and W, independently of one another, is selected from the group consisting of

E,

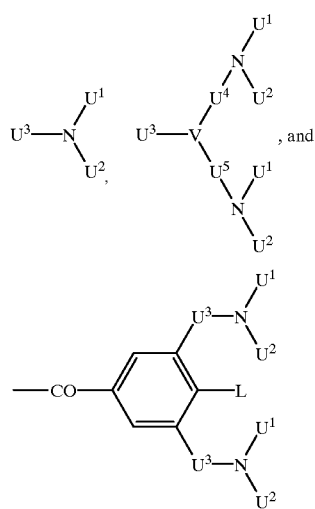

, and

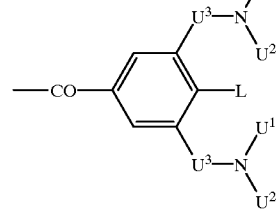

in which $U^1$ stands for $Q^1$ or E, $U^2$ stands for $Q^2$ or E with

E meaning the group

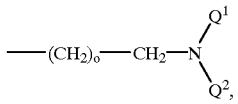

in which o stands for a number from 1 to 6, $Q^1$ stands for a hydrogen atom or $Q^2$, $Q^2$ stands for a direct bond, $U^3$ stands for a $C_1$–$C_{20}$ alkylene chain which optionally is interrupted by 1 to 10 oxygen atoms, 1 to 2 —$NR^2$—(CO)$_q$ radicals, 1 to 2 phenylene radicals, 1 to 2 phenylenoxy radicals or combination thereof, and optionally is substituted by 1 to 2 oxo, thioxo, carboxy, $C_1$–$C_5$ alkylcarboxy, $C_1$–$C_5$ alkoxy, hydroxy or $C_1$–$C_5$ alkyl groups, in which q stands for numbers 0 or 1 and $R^2$ stands for a hydrogen atom, a methyl or an ethyl radical, which optionally is substituted with 1–2 hydroxy or 1 carboxy group(s), L stands for a hydrogen atom or the group

V stands for methine group

in which case $U^4$ means a direct bond or group M and $U^5$ has one of the meanings of $U^3$ or V stands for group

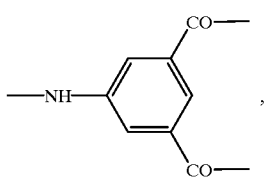

in which case $U^4$ and $U^5$ are identical and mean the direct bond or group M where M stands for a $C_{1-10}$-alkylene chain which optionally is interrupted by 1 to 3 oxygen atoms and optionally is substituted with 1 to 2 oxo groups, wherein complexing agent radical K bound to the terminal nitrogen atoms of the last generation of reproduction unit W stands for a radical of formula IA or IB (IA)

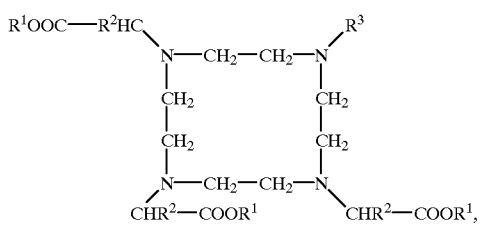

(IB)

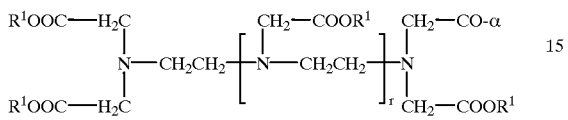

in which

- $R^1$ independently of one another, stand for a hydrogen atom or a metal ion equivalent of atomic numbers 20–29, 39, 42–44 or 57–83,
- $R^2$ stands for a hydrogen atom, a methyl or an ethyl radical which optionally is substituted with 1–2 hydroxy or 1 carboxy group(s),
- $R^3$ stands for a —$CH_2$—$CH(OH)$—$U^6$—T or —$CH_2$—CO—$U^7$ group,
- $U^6$ stands for a straight-chain, branched, saturated or unsaturated $C_1$–$C_{20}$ alkylene group optionally containing 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups, or 1–10 oxygen, 1–5 sulfur or 1–5 nitrogen atom(s); and optionally substituted by 1–5 hydroxy, 1–2 mercapto, 1–5 oxo, 1–5 thioxo, 1–3 carboxy, 1–5 carboxyalkyl, 1–5 ester, 1–3 amino group(s) or combinations thereof, and the phenylene groups that are optionally contained can be substituted by 1–2 carboxy, 1–2 sulfo or 1–2 hydroxy groups,
- $U^7$ stands for a direct bond or radical —$NR^2$—$U^6$—T,
- T stands for a —CO—α, —NHCO—α or —NHCS—α group,
- α stands for the bonding site to the terminal nitrogen atoms of the last generation, of reproduction unit W and
- r stands for numbers 0, 1, 2 or 3, provided that at least two, in the case of divalent metals, or three, in the case of trivalent metals, of substituents $R^1$ stand for a metal ion equivalent of the above-mentioned elements and that optionally other carboxyl groups are present in the form of their salts with inorganic bases, organic bases, amino acids or amino acid amides.

2. A cascade polymer complex according to claim 1, wherein A is selected from the group consisting of a nitrogen atom,

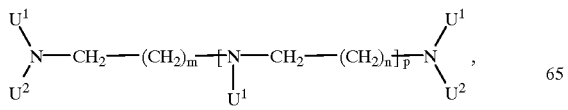

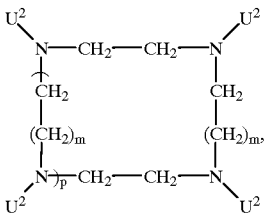

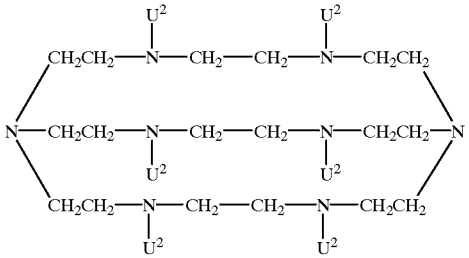

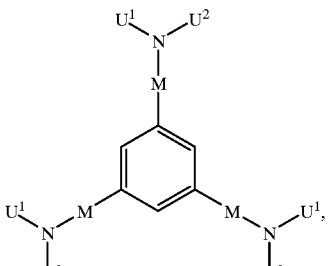

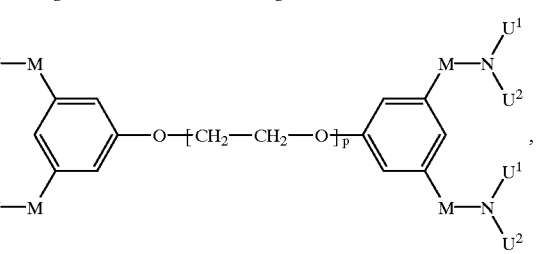

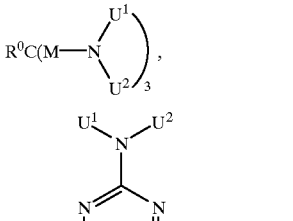

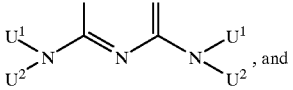
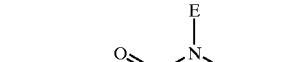
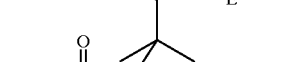, and

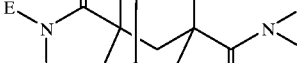
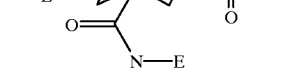

in which
m and n stand for a number from 1 to 10,
p stands for a number from 0 to 10,
$U^1$ stands for $Q^1$ or E,
$U^2$ stands for $Q^2$ or E with
E meaning the group

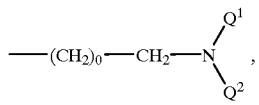

which
o stands for a number from 1 to 6,
$Q^1$ stands for a hydrogen atom or $Q^2$ and
$Q^2$ stands for a direct bond,
M stands for a $C_1$–$C_{10}$ alkylene chain which optionally is interrupted by 1 to 3 oxygen atoms and optionally is substituted with 1 to 2 oxo groups, and
$R^o$ stands for a branched or unbranched $C_1$–$C_{10}$ alkyl radical, a nitro, amino or carboxylic acid group or for

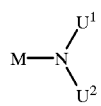

wherein the number of $Q^2$ groups is equal to the base multiplicity a.

3. A cascade polymer complex according to claim 1, wherein the $C_1$–$C_{20}$ alkylene chain that stands for $U^6$ contains a group —$CH_2NHCO$, —$NHCOCH_2O$, —$NHCOCH_2OC_6H_4$, —$N(CH_2CO_2H)$, —$NHCOCH_2C_6H_4$, —$NHCSNHC_6H_4$, —$CH_2OC_6H_4$, or —$CH_2CH_2O$ and is optionally substituted by groups —COOH, —$CH_2COOH$.

4. A cascade polymer complex according to claim 1, wherein $U^6$ stands for a
—$CH_2$—, —$CH_2CH_2$—, —$CH_2CH_2CH_2$—, —$C_6H_4$—, —$C_6H_{10}$—, —$CH_2C_6H_5$—, —$CH_2NHCOCH_2CH(CH_2CO_2H)$—$C_6H_4$—, —$CH_2NHCOCH_2OCH_2$—, —$CH_2NHCOCH_2C_6H_4$—,

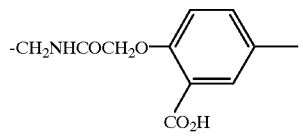

—$CH_2NHCSNH$—$C_6H_4$—$CH(CH_2COOH)CH_2$—, —$CH_2OC_6H_4$—$N(CH_2COOH)CH_2$—, —$CH_2NHCOCH_2O(CH_2CH_2O)_4$—$C_6H_4$—, —$CH_2O$—$C_6H_4$—, —$CH_2CH_2$—O—$CH_2CH_2$—, —$CH_2CH_2$—O—$CH_2CH_2$—O—$CH_2CH_2$—,

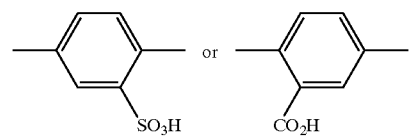

group.

5. A cascade polymer complex according to claim 1, wherein radicals $U^3$, $U^4$ and $U^5$ are contained in a cascade reproduction unit X, Y, Z or W and
radical $U^3$ is —CO—, —$COCH_2OCH_2CO$—, —$COCH_2$—, —$CH_2CH_2$—, —$CONHC_6H_4$—, —$COCH_2CH_2CO$—, —$COCH_2$—$CH_2CH_2CO$—, or —$COCH_2CH_2CH_2CH_2CO$—, radical $U^4$ stands for a direct bond, or —$CH_2CO$—, and radical $U^5$ stands for a direct bond, —$(CH_2)_4$—, —$CH_2CO$—, —CH(COOH)—, $CH_2OCH_2CH_2$—, —$CH_2C_6H_4$—, $CH_2$—$C_6H_4OCH_2CH_2$—.

6. A cascade polymer complex according to claim 1, wherein cascade reproduction units X, Y, Z and W, independently of one another, stand for
—$CH_2CH_2NH$—; —$CH_2CH_2N<$; —$COCH(NH—)(CH_2)_4NH$—; —$COCH(N<)(CH_2)_4N<$; —$COCH_2OCH_2CON(CH_2CH_2NH—)_2$; —$COCH_2OCH_2CON(CH_2CH_2N<)_2$; —$COCH_2N(CH_2CH_2NH—)_2$; —$COCH_2N(CH_2CH_2N<)_2$; —$COCH_2NH$—; —$COCH_2N<$; —$COCH_2CH_2CON(CH_2CH_2NH—)_2$; —$COCH_2CH_2CON(CH_2CH_2N<)_2$; —$COCH_2OCH_2CONH$—$C_6H_4$—$CH[CH_2CON(CH_2CH_2NH—)_2]_2$; —$COCH_2OCH_2CONH$—$C_6H_4$—$CH[CH_2CON(CH_2CH_2N<)_2]_2$; —$COCH_2CH_2CO$—NH—$C_6H_4$—$CH[CH_2CON(CH_2CH_2NH—)_2]_2$; —$COCH_2CH_2CO$—NH—$C_6H_4$—$CH[CH_2CON(CH_2CH_2N<)_2]_2$; —CONH—$C_6H_4$—$CH[CH_2CON(CH_2CH_2NH—)_2]_2$; —CONH—$C_6H_4$—$CH[CH_2CON(CH_2CH_2N<)_2]_2$; —COCH(NH—)CH(COOH)NH—; —COCH(N<)CH(COOH)N<;

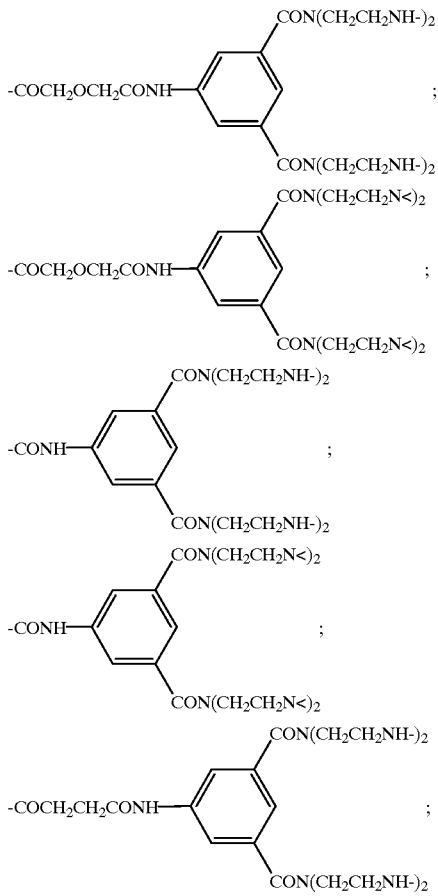

-continued

-COCH₂CH₂CONH—[benzene ring with CON(CH₂CH₂N<)₂ and CON(CH₂CH₂N<)₂ substituents] ;

-CO—[benzene ring with OCH₂CH₂NH- and OCH₂CH₂NH- substituents] ;

-CO—[benzene ring with OCH₂CH₂N< and OCH₂CH₂N< substituents] ;

-CO—[benzene ring with OCH₂CH₂NH-, OCH₂CH₂NH-, OCH₂CH₂NH-, and OCH₂CH₂NH- substituents]

-CO—[benzene ring with OCH₂CH₂N<, OCH₂CH₂N<, OCH₂CH₂N<, OCH₂CH₂N< substituents];

-CO—[benzene ring with O(CH₂CH₂O)₂CH₂CH₂NH-, O(CH₂CH₂O)₂CH₂CH₂NH-, O(CH₂CH₂O)₂CH₂CH₂NH-, O(CH₂CH₂O)₂CH₂CH₂NH- substituents]

-CO—[benzene ring with O(CH₂CH₂O)₂CH₂CH₂N<, O(CH₂CH₂O)₂CH₂CH₂N<, O(CH₂CH₂O)₂CH₂CH₂N<, O(CH₂CH₂O)₂CH₂CH₂N< substituents].

7. A cascade polymer complex according to claim 2, wherein m stands for a number from 1–3, n stands for a number from 1–3, o stands for 1, p stands for a number from 0–3, M stands for a —CH₂, —CO or —CH₂CO group and R° stands for a —CH₂NU¹U², CH₃ or NO₂ group.

8. A pharmaceutical agent containing at least one cascade polymer complex according to claim 1, optionally with the additives usual in galenicals.

9. A process for the production of a cascade polymer complex according to claim 1, wherein a compound of general formula I'

$$A-\{X-[Y-(Z-<W-\beta_{W>z})_y]_x\}a \qquad (I'),$$

in which

A stands for a nitrogen-containing cascade nucleus of base multiplicity a,

X and Y, independently of one another, stand for a direct bond or a cascade reproduction unit of reproduction multiplicity x or y, Z and W, independently of one another, stand for a cascade reproduction unit of reproduction multiplicity z or w, a stands for numbers 2 to 12, x, y, z and w, independently of one another, stand for numbers 1 to 4, and β stands for the bonding site of the terminal NH groups of the last generation, of reproduction unit W provided that at least two reproduction units are different and that $$16 \leq a \cdot x \cdot y \cdot z \cdot w \leq 64$$

holds true for the product of multiplicities, is reacted with a complex or complexing agent K' of general formula I'A or I'B $$R^{1'}OOC-R^2HC\diagdown N-CH_2-CH_2-N\diagup R^{3'} \\ CH_2 \qquad CH_2 \\ CH_2 \qquad CH_2 \\ N-CH_2-CH_2-N \\ CHR^2-COOR^{1'} \qquad CHR^2-COOR^{1'} \qquad (I'A)$$

$$R^{1'}OOC-H_2C \qquad CH_2-COOR^{1'} \quad CH_2-C^*O- \\ \diagdown N-CH_2CH_2-[N-CH_2CH_2]_r-N \\ R^{1'}OOC-H_2C \qquad CH_2-COOR^{1'} \qquad (I'B)$$

in which

R¹', independently of one another, stand for a hydrogen atom, a metal ion equivalent of atomic numbers 20–29, 39, 42–44, or 57–83 or an acid protective group, R² stands for a hydrogen atom, a methyl or an ethyl radical which optionally is substituted with 1–2 hydroxy or 1 carboxy group(s), R³' stands for a —CH₂—H(OH)—U⁶—T' or —CH₂—CO—U⁷' group, U⁶ stands for a straight-chain, branched, saturated or unsaturated C₁—C₂₀ alkylene group optionally containing 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups; 1–10 oxygen, 1–5 sulfur 1–5 nitrogen atom(s) or combination thereof and optionally substituted by 1–5 hydroxy, 1–2 mercapto, 1–5 oxo, 1–5 thioxo, 1–3 carboxy, 1–5 carboxyalkyl, 1–5 ester, 1–3 amino group(s) or combination thereof, and the phenylene groups that are optionally contained can be substituted by 1–2 carboxy, 1–2 sulfo or 1–2 hydroxy groups, $U^{7'}$ stands for a direct bond or radical —$NR^2$—$U^6$—T', T' stands for a —C*O, —COOH, —N=C=O or —N=C=S group, C*O stands for an activated carboxyl group and r stands for numbers 0, 1, 2 or 3 provided that if K' stands for a complex at least two, in the case of divalent metals, or three, in the case of trivalent metals, of substituents R' stand for a metal ion equivalent of the above-mentioned elements and that, optionally, other carboxyl groups are present in the form of their salts with inorganic bases; organic bases, amino acids or amino acid amides, cleaving any optionally present protective groups, the thus obtained cascade polymers—if K' stands for a complexing agent—are reacted with at least one metal oxide or metal salt of an element of atomic numbers 20–29, 39, 42, 44, or 57–83 and optionally then in the cascade polymer complexes thus obtained, acid hydrogen atoms that are still present are completely or partially substituted by cations of inorganic bases, organic bases, amino acids, or amino acid amides.

10. A process for the production of a pharmaceutical agent according to claim 8, wherein the cascade polymer complex, dissolved or suspended in water or physiological salt solution, optionally with the additives usual in galenicals, is brought into a form suitable for enteral or parenteral administration.

11. A cascade polymer complex according to claim 1, wherein a cascade reproduction unit X, Y, Z or W is E which is —$CH_2$—$CH_2$—$N(Q^1Q^2)$.

12. A method for NMR diagnosis or diagnostic radiology which comprises administering a cascade polymer complex according to claim 1 to enhance said diagnosis or diagnostic radiology.

13. A cascade polymer complex of claim 1, wherein at least one reproduction unit X, Y, Z or W is of the following formula:

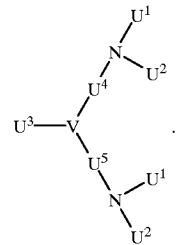

14. A cascade polymer complex of claim 1 which is 24-gadolinium-DTPA-monoamide of N,N,N',N',N'',N''-hexakis[(2-trilysylamino)-ethyl]-trimesic acid triamide.

* * * * *